(12) United States Patent
Becker et al.

(10) Patent No.: US 11,505,535 B2
(45) Date of Patent: *Nov. 22, 2022

(54) TREPROSTINIL DERIVATIVE COMPOUNDS AND METHODS OF USING SAME

(71) Applicant: CORSAIR PHARMA, INC., South San Francisco, CA (US)

(72) Inventors: Cyrus K. Becker, Pleasanton, CA (US); Meenakshi S. Venkatraman, Fremont, CA (US); Xiaoming Zhang, Sunnyvale, CA (US)

(73) Assignee: Corsair Pharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/214,460

(22) Filed: Mar. 26, 2021

(65) Prior Publication Data

US 2022/0112173 A1    Apr. 14, 2022

Related U.S. Application Data

(63) Continuation of application No. 16/569,840, filed on Sep. 13, 2019, now Pat. No. 11,046,666, which is a continuation of application No. 15/811,522, filed on Nov. 13, 2017, now Pat. No. 10,450,290, which is a continuation of application No. 15/296,164, filed on Oct. 18, 2016, now Pat. No. 9,845,305, which is a continuation of application No. 14/333,456, filed on
(Continued)

(51) Int. Cl.
| | |
|---|---|
| C07D 321/00 | (2006.01) |
| C07C 59/72 | (2006.01) |
| C07C 235/20 | (2006.01) |
| A61K 31/165 | (2006.01) |
| C07C 69/734 | (2006.01) |
| A61K 31/216 | (2006.01) |
| A61K 31/365 | (2006.01) |
| C07D 307/20 | (2006.01) |
| A61K 31/341 | (2006.01) |
| A61K 45/06 | (2006.01) |
| A61K 9/00 | (2006.01) |
| C07D 317/34 | (2006.01) |
| C07C 69/712 | (2006.01) |
| C07D 317/40 | (2006.01) |
| C07C 219/16 | (2006.01) |
| C07D 453/02 | (2006.01) |
| C07D 257/06 | (2006.01) |
| C07D 263/24 | (2006.01) |
| C07D 263/26 | (2006.01) |
| C07D 265/30 | (2006.01) |
| C07D 207/08 | (2006.01) |
| C07D 295/088 | (2006.01) |
| C07D 211/60 | (2006.01) |
| C07D 295/145 | (2006.01) |
| C07C 69/74 | (2006.01) |
| C07C 69/96 | (2006.01) |
| A61K 9/70 | (2006.01) |

(52) U.S. Cl.
CPC .......... *C07D 321/00* (2013.01); *A61K 9/0014* (2013.01); *A61K 9/7023* (2013.01); *A61K 31/165* (2013.01); *A61K 31/216* (2013.01); *A61K 31/341* (2013.01); *A61K 31/365* (2013.01); *A61K 45/06* (2013.01); *C07C 59/72* (2013.01); *C07C 69/712* (2013.01); *C07C 69/734* (2013.01); *C07C 69/74* (2013.01); *C07C 69/96* (2013.01); *C07C 219/16* (2013.01); *C07C 235/20* (2013.01); *C07D 207/08* (2013.01); *C07D 211/60* (2013.01); *C07D 257/06* (2013.01); *C07D 263/24* (2013.01); *C07D 263/26* (2013.01); *C07D 265/30* (2013.01); *C07D 295/088* (2013.01); *C07D 295/145* (2013.01); *C07D 307/20* (2013.01); *C07D 317/34* (2013.01); *C07D 317/40* (2013.01); *C07D 453/02* (2013.01); *C07C 2601/02* (2017.05); *C07C 2601/08* (2017.05); *C07C 2601/14* (2017.05); *C07C 2602/42* (2017.05); *C07C 2603/14* (2017.05)

(58) Field of Classification Search
CPC .............................. C07D 321/00; C07C 59/72
See application file for complete search history.

(56) References Cited

U.S. PATENT DOCUMENTS

| | | |
|---|---|---|
| 3,598,122 A | 8/1971 | Zaffaroni |
| 4,144,317 A | 3/1979 | Higuchi et al. |

(Continued)

FOREIGN PATENT DOCUMENTS

| | | |
|---|---|---|
| EP | 0496548 A1 | 7/1992 |
| EP | 1628654 A2 | 3/2006 |

(Continued)

OTHER PUBLICATIONS

Japanese Patent Office, Notice of Reasons for Rejection for Japanese Application No. 2019-134245, dated Jul. 27, 2020.

(Continued)

*Primary Examiner* — Shawquia Jackson
(74) *Attorney, Agent, or Firm* — The Marbury Law Group, PLLC

(57) ABSTRACT

Compounds represented by formulae I, II, III, and IV including pro-drugs for treprostinil and prostacyclin analogs. Uses include treatment of pulmonary hypertension (PH) or pulmonary arterial hypertension (PAH). The structures of the compounds can be adapted to the particular application for a suitable treatment dosage. Transdermal applications can be used.

20 Claims, No Drawings

Related U.S. Application Data

Jul. 16, 2014, now Pat. No. 9,505,737, which is a continuation-in-part of application No. 14/153,498, filed on Jan. 13, 2014, now Pat. No. 9,371,264.

(60) Provisional application No. 61/751,608, filed on Jan. 11, 2013.

(56) References Cited

U.S. PATENT DOCUMENTS

| | | |
|---|---|---|
| 4,201,211 A | 5/1980 | Chandrasekaran et al. |
| 4,262,003 A | 4/1981 | Urquhart et al. |
| 4,306,075 A | 12/1981 | Aristoff |
| 4,306,076 A | 12/1981 | Nelson |
| 4,338,457 A | 7/1982 | Aristoff |
| 4,349,689 A | 9/1982 | Aristoff |
| 4,379,454 A | 4/1983 | Campbell et al. |
| 4,420,632 A | 12/1983 | Aristoff |
| 4,525,586 A | 6/1985 | Aristoff |
| 4,668,814 A | 5/1987 | Aristoff |
| 4,683,330 A | 7/1987 | Aristoff |
| 5,028,628 A | 7/1991 | Tadepalli et al. |
| 5,071,657 A | 12/1991 | Oloff et al. |
| 5,088,977 A | 2/1992 | Sibalis |
| 5,153,222 A | 10/1992 | Tadepalli et al. |
| 5,328,453 A | 7/1994 | Sibalis |
| 5,797,898 A | 8/1998 | Santini, Jr. et al. |
| 5,853,751 A | 12/1998 | Masiz |
| 5,972,974 A | 10/1999 | Keenan |
| 6,242,482 B1 | 6/2001 | Shorr et al. |
| 6,264,990 B1 | 7/2001 | Knepp et al. |
| 6,635,274 B1 | 10/2003 | Masiz et al. |
| 6,638,528 B1 | 10/2003 | Kanios |
| 6,700,025 B2 | 3/2004 | Moriarty et al. |
| 6,809,223 B2 | 10/2004 | Moriarty et al. |
| 7,199,157 B2 | 4/2007 | Wade et al. |
| 7,375,139 B2 | 5/2008 | Aldred |
| 7,384,978 B2 | 6/2008 | Phares et al. |
| 7,417,070 B2 | 8/2008 | Phares et al. |
| 7,537,590 B2 | 5/2009 | Santini, Jr. et al. |
| 7,544,713 B2 | 6/2009 | Phares et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,410,169 B2 | 4/2013 | Phares et al. |
| 8,435,944 B2 | 5/2013 | Dipietro et al. |
| 8,481,782 B2 | 7/2013 | Batra et al. |
| 8,497,393 B2 | 7/2013 | Batra et al. |
| 8,519,178 B2 | 8/2013 | Hogan et al. |
| 8,524,939 B2 | 9/2013 | Wei et al. |
| 8,536,363 B2 | 9/2013 | Phares et al. |
| 8,563,614 B2 | 10/2013 | Wade et al. |
| 8,591,941 B2 | 11/2013 | Kanios et al. |
| 8,609,134 B2 | 12/2013 | Yoneto et al. |
| 8,617,591 B2 | 12/2013 | Schacht et al. |
| 8,658,837 B2 | 2/2014 | Wei et al. |
| 8,747,897 B2 | 6/2014 | Kidane et al. |
| 8,748,657 B2 | 6/2014 | Batra et al. |
| 8,765,813 B2 | 7/2014 | Wade et al. |
| 8,809,334 B2 | 8/2014 | Clozel |
| 8,846,021 B2 | 9/2014 | Charles |
| 8,877,710 B2 | 11/2014 | Johansson |
| 8,940,930 B2 | 1/2015 | Batra et al. |
| 8,957,240 B2 | 2/2015 | Hogan et al. |
| 9,050,311 B2 | 6/2015 | Batra et al. |
| 9,102,660 B2 | 8/2015 | Batra et al. |
| 9,156,786 B2 | 10/2015 | Batra et al. |
| 9,199,908 B2 | 12/2015 | Phares et al. |
| 9,255,064 B2 | 2/2016 | Malinin et al. |
| 9,278,901 B2 | 3/2016 | Phares et al. |
| 9,278,903 B2 | 3/2016 | Tang |
| 9,327,105 B2 | 5/2016 | Ramdas et al. |
| 9,346,738 B2 | 5/2016 | Jain et al. |
| 9,371,264 B2 | 6/2016 | Becker et al. |
| 9,394,227 B1 | 7/2016 | Zhang et al. |
| 9,422,223 B2 | 8/2016 | Phares |
| 9,469,600 B2 | 10/2016 | Malinin et al. |
| 9,505,704 B2 | 11/2016 | Gao et al. |
| 9,505,737 B2 | 11/2016 | Becker et al. |
| 9,643,911 B2 | 5/2017 | Phares et al. |
| 9,701,616 B2 | 7/2017 | Zhang et al. |
| 9,776,982 B2 | 10/2017 | Becker et al. |
| 9,845,305 B2 | 12/2017 | Becker et al. |
| 9,957,220 B2 | 5/2018 | Zhang et al. |
| 10,053,414 B2 | 8/2018 | Zhang et al. |
| 10,344,012 B2 | 7/2019 | Becker et al. |
| 10,246,403 B2 | 8/2019 | Zhang et al. |
| 10,450,290 B2 | 10/2019 | Becker et al. |
| 10,464,877 B2 | 11/2019 | Zhang et al. |
| 10,464,878 B2 | 11/2019 | Zhang et al. |
| 10,703,706 B2 | 7/2020 | Zhang et al. |
| 10,752,605 B2 | 8/2020 | Becker et al. |
| 10,759,733 B2 | 9/2020 | Zhang et al. |
| 11,034,645 B2 | 6/2021 | Zhang et al. |
| 11,046,666 B2 | 6/2021 | Becker et al. |
| 2002/0099034 A1 | 7/2002 | Moriarty et al. |
| 2003/0108512 A1 | 6/2003 | Shorr et al. |
| 2004/0176645 A1 | 9/2004 | Moriarty et al. |
| 2005/0080140 A1 | 4/2005 | Hatae et al. |
| 2005/0085540 A1 | 4/2005 | Phares et al. |
| 2005/0165110 A1 | 7/2005 | Wade et al. |
| 2005/0165111 A1 | 7/2005 | Wade et al. |
| 2005/0282901 A1 | 12/2005 | Phares et al. |
| 2007/0078095 A1 | 4/2007 | Phares et al. |
| 2007/0078182 A1 | 4/2007 | Phares et al. |
| 2007/0082948 A1 | 4/2007 | Phares et al. |
| 2007/0254032 A1 | 11/2007 | Kidane et al. |
| 2008/0200449 A1 | 8/2008 | Oischewski et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0163738 A1 | 6/2009 | Batra et al. |
| 2010/0076083 A1 | 3/2010 | Oischewski et al. |
| 2010/0166700 A1 | 7/2010 | Charles |
| 2010/0282622 A1 | 11/2010 | Phares |
| 2010/0324313 A1 | 12/2010 | Hogan et al. |
| 2011/0092599 A1 | 4/2011 | Wade et al. |
| 2011/0118213 A1 | 5/2011 | Phares et al. |
| 2011/0136818 A1 | 6/2011 | Clozel |
| 2011/0268732 A1 | 11/2011 | Johansson |
| 2011/0294815 A1 | 12/2011 | Harbeson |
| 2011/0319641 A1 | 12/2011 | Batra et al. |
| 2012/0010159 A1 | 1/2012 | Rothblatt et al. |
| 2012/0129941 A1 | 5/2012 | Wade et al. |
| 2012/0184622 A1 | 7/2012 | Freissmuth et al. |
| 2012/0190888 A1 | 7/2012 | Batra et al. |
| 2012/0197041 A1 | 8/2012 | Batra et al. |
| 2012/0216801 A1 | 8/2012 | Olschewski et al. |
| 2012/0283470 A1 | 11/2012 | Batra et al. |
| 2012/0295980 A1 | 11/2012 | Phares et al. |
| 2013/0040898 A1 | 2/2013 | Johansson |
| 2013/0053581 A1 | 2/2013 | Wei et al. |
| 2013/0096200 A1 | 4/2013 | Wade et al. |
| 2013/0165389 A1 | 6/2013 | Sohellenberger |
| 2013/0184295 A1 | 7/2013 | Sprague et al. |
| 2013/0261187 A1 | 10/2013 | Phares et al. |
| 2013/0267734 A1 | 10/2013 | Batra et al. |
| 2013/0274261 A1 | 10/2013 | Sands |
| 2013/0289304 A1 | 10/2013 | Batra et al. |
| 2013/0317245 A1 | 11/2013 | Wei et al. |
| 2013/0317249 A1 | 11/2013 | Hogan et al. |
| 2013/0331593 A1 | 12/2013 | Mcgowan et al. |
| 2013/0337534 A1 | 12/2013 | Charles |
| 2013/0344038 A1 | 12/2013 | Freissmuth et al. |
| 2014/0018430 A1 | 1/2014 | Freissmuth et al. |
| 2014/0018431 A1 | 1/2014 | Wade et al. |
| 2014/0024856 A1 | 1/2014 | Giust |
| 2014/0044797 A1 | 2/2014 | Johansson et al. |
| 2014/0193379 A1 | 7/2014 | Jeffs et al. |
| 2014/0249093 A1 | 9/2014 | Vetter et al. |
| 2014/0256730 A1 | 9/2014 | Becker et al. |
| 2014/0275616 A1 | 9/2014 | Batra et al. |
| 2014/0283314 A1 | 9/2014 | Batra et al. |

(56) References Cited

U.S. PATENT DOCUMENTS

| | | |
|---|---|---|
| 2014/0296150 A1 | 10/2014 | Hersel et al. |
| 2014/0303245 A1 | 10/2014 | Sprogoee et al. |
| 2014/0303252 A1 | 10/2014 | Kidane et al. |
| 2014/0322207 A1 | 10/2014 | Johansson |
| 2014/0323567 A1 | 10/2014 | Laing |
| 2014/0329824 A1 | 11/2014 | Clozel |
| 2015/0005374 A1 | 1/2015 | Phares et al. |
| 2015/0050714 A1 | 2/2015 | Charles |
| 2015/0057325 A1 | 2/2015 | Johansson et al. |
| 2015/0087688 A1 | 3/2015 | Hersel et al. |
| 2015/0105582 A1 | 4/2015 | Batra et al. |
| 2015/0126761 A1 | 5/2015 | Jain et al. |
| 2015/0126764 A1 | 5/2015 | Hogan et al. |
| 2015/0148414 A1 | 5/2015 | Malinin et al. |
| 2015/0166503 A1 | 6/2015 | Becker et al. |
| 2015/0175529 A1 | 6/2015 | Malinin et al. |
| 2015/0259274 A1 | 9/2015 | Batra et al. |
| 2015/0299091 A1 | 10/2015 | Batra et al. |
| 2015/0376106 A1 | 12/2015 | Batra et al. |
| 2016/0030371 A1 | 2/2016 | Batra et al. |
| 2016/0051505 A1 | 2/2016 | Batra et al. |
| 2016/0152548 A1 | 6/2016 | Gao et al. |
| 2016/0243064 A1 | 8/2016 | Trehan et al. |
| 2016/0256425 A1 | 9/2016 | Malinin et al. |
| 2016/0289158 A1 | 10/2016 | Chambournier et al. |
| 2016/0318844 A1 | 11/2016 | Malinin et al. |
| 2016/0355455 A1 | 12/2016 | Batra et al. |
| 2016/0368854 A1 | 12/2016 | Zhang et al. |
| 2016/0368855 A1 | 12/2016 | Zhang et al. |
| 2016/0368889 A1 | 12/2016 | Becker et al. |

FOREIGN PATENT DOCUMENTS

| | | |
|---|---|---|
| EP | 2252570 A1 | 11/2010 |
| EP | 2427054 A1 | 3/2012 |
| EP | 2674413 A1 | 12/2013 |
| EP | 2792353 A2 | 10/2014 |
| EP | 2792353 A3 | 10/2014 |
| EP | 2841109 A1 | 3/2015 |
| EP | 2861554 A2 | 4/2015 |
| EP | 2978313 A1 | 2/2016 |
| EP | 3060041 A2 | 8/2016 |
| EP | 3068752 A1 | 9/2016 |
| JP | 2003535132 A | 11/2003 |
| JP | 2004131499 A | 4/2004 |
| JP | 2007501281 A | 1/2007 |
| JP | 2010-527987 A | 8/2010 |
| JP | 2013528621 A | 7/2013 |
| JP | S54-20129 B2 | 2/2014 |
| JP | 2010531293 A | 9/2020 |
| WO | 2000057701 A1 | 10/2000 |
| WO | 2001093862 A1 | 12/2001 |
| WO | 2002053517 A2 | 7/2002 |
| WO | 2002053517 A3 | 7/2002 |
| WO | 2003049676 A2 | 6/2003 |
| WO | 2003049676 A3 | 6/2003 |
| WO | 2005007081 | 1/2005 |
| WO | 2005007081 A3 | 1/2005 |
| WO | 2005058303 A1 | 6/2005 |
| WO | 2005058329 A1 | 6/2005 |
| WO | 2007100902 A2 | 9/2007 |
| WO | 2007100902 A3 | 9/2007 |
| WO | 2007127216 A2 | 11/2007 |
| WO | 2007127216 A3 | 11/2007 |
| WO | 2007134292 A2 | 11/2007 |
| WO | 2007134292 A3 | 11/2007 |
| WO | 2008002929 A2 | 1/2008 |
| WO | 2008002929 A3 | 1/2008 |
| WO | 2008049000 A2 | 4/2008 |
| WO | 2008049000 A3 | 4/2008 |
| WO | 2008098196 A1 | 8/2008 |
| WO | 2009001968 A1 | 12/2008 |
| WO | 2009078965 A1 | 6/2009 |
| WO | 2009152160 | 12/2009 |
| WO | 2009158010 A1 | 12/2009 |
| WO | 2010018549 A2 | 2/2010 |
| WO | 2010018549 A3 | 2/2010 |
| WO | 2010075861 A2 | 7/2010 |
| WO | 2010075861 A3 | 7/2010 |
| WO | 2010129757 A1 | 11/2010 |
| WO | 2011005505 A2 | 1/2011 |
| WO | 2011005505 A3 | 1/2011 |
| WO | 2011015630 A1 | 2/2011 |
| WO | 2011123813 A2 | 10/2011 |
| WO | 2011123813 A3 | 11/2011 |
| WO | 2011134478 A2 | 11/2011 |
| WO | 2011134478 A3 | 11/2011 |
| WO | 2011153363 A1 | 12/2011 |
| WO | 2012006273 A1 | 1/2012 |
| WO | 2012009816 | 1/2012 |
| WO | 2012088607 A1 | 7/2012 |
| WO | 2012095511 A1 | 7/2012 |
| WO | 2012107363 A1 | 8/2012 |
| WO | 2012107364 A1 | 8/2012 |
| WO | 2012143012 A1 | 10/2012 |
| WO | 2013022846 A3 | 2/2013 |
| WO | 2013024051 | 2/2013 |
| WO | 2013024052 | 2/2013 |
| WO | 2013024053 A1 | 2/2013 |
| WO | 2013143548 A1 | 10/2013 |
| WO | 2013160340 A1 | 10/2013 |
| WO | 2013174848 A2 | 11/2013 |
| WO | 2013174848 A3 | 11/2013 |
| WO | 2014022373 A1 | 2/2014 |
| WO | 2014089385 A2 | 6/2014 |
| WO | 2014089385 A3 | 6/2014 |
| WO | 2014110094 A1 | 7/2014 |
| WO | 2014110491 A1 | 7/2014 |
| WO | 2014150203 A1 | 9/2014 |
| WO | 2014160638 A1 | 10/2014 |
| WO | 2014179295 A1 | 11/2014 |
| WO | 2014203278 A2 | 12/2014 |
| WO | 2014203278 A3 | 12/2014 |
| WO | 2015061720 A2 | 4/2015 |
| WO | 2015073314 A1 | 5/2015 |
| WO | 2015061720 A3 | 6/2015 |
| WO | 2015138423 A1 | 9/2015 |
| WO | 2015138423 A9 | 9/2015 |
| WO | 2016010538 A1 | 1/2016 |
| WO | 2016055819 A1 | 4/2016 |
| WO | 2016081658 A1 | 5/2016 |
| WO | 2016120311 A1 | 8/2016 |
| WO | 2016176555 A1 | 11/2016 |
| WO | 2016205202 A1 | 12/2016 |

OTHER PUBLICATIONS

Findlay, et al., Prostaglandins, Leukotrienes and Essential Fatty Acids, vol. 48, Issue No. 2, 1993, pp. 167-174 (8 pages).

Geiger, et al., Biomaterials, vol. 31, Issue No. 10, 2010, p. 2903-2911 (9 pages).

Thayer, Chemical & Engineering News, Jun. 18, 2007, vol. 85, Issue 25, pp. 17-30 (14 pages).

Cochrane, et al., "A Macrolactonization Approach to the Total Synthesis of the Antimicrobial Cyclic Depsipeptide Li-F04a and Diastereosiomeric Analogues," Beilstein Journal of Organic Chemistry, vol. 8, 1344-1351 (2012) (7 pages).

Gannes, L. Z., et al., "Natural Abundance Variations in Stable isotopes and Their Potential Uses in Animal Physiological Ecology," Comp Biochem Physiol Mol Integr Physiol, 119:725-737 (1998).

Handbook of Reagents of Organic Synthesis: Activating Agents and Protecting Groups, Pearson and Rousch (Ed.), John Wiley & Sons (199).

Shiina, Isamu, "Total Synthesis of Natural 8- and 9-Membered Lactones; Recent Advancements in Medium-Sized Ring Formations," Chemical Reviews 107, pp. 239-273 (2007) (35 pages).

Smith, Michael B., et al., "March's Advanced Organic Chemistry: Reactions, Mechanisms and Structure," 6th Ed., Wiley & Sons (2007).

(56) References Cited

OTHER PUBLICATIONS

Wada, E, et al., "Natural Abundance of Carbon, Nitrogen, and Hydrogen Isotope Ratios in Biogenic Substances: Present and Future," Seikagaku, 66:15-29 (English portions included) (1994) (15 pages).

Wuts, Peter G. and Greene, Theodora W., "Greene's Protective Groups in Organic Synthesis," 4th Ed., John Wiley & Sons (2007).

Schanz, et al., "Topical Treatment of Erectile Dysfunction with Prostaglandin E1 Ethylester," J. Dtsch Dermatol. Ges., 7:1055-59 (2009).

Rautio, et al., "Prodrugs: Design and Clinical Applications," Nature Reviews: Drug Discovery 2008, 7, 2008, pp. 255-270 (16 pages).

Paudel, et al., "Challenges and Opportunities in Dermal/Transdermal Delivery," Ther Deliv., 2010, 1, pp. 109-131 (33 pages).

USPTO, International Search Report and Written Opinion received in connection with International Patent Application No. PCT/US2014/011260, dated May 6, 2014.

Invitation to Pay Additional Fees with Partial International Search Report received in connection with International Patent Application No. PCT/US014/046920, dated Sep. 11, 2014.

Zhang, et al., "Treprostinil Derivatives and Compositions and Uses Thereof," U.S. Appl. No. 14/829,180, filed Aug. 18, 2015.

Doh, Hea-Jeong, et al., "Synthesis and Evaluation of Ketorolac Ester Prodrugs for Transdermal Delivery," J. of Pharmaceutical Sciences, vol. 92, No. 5, May 2003.

European Patent Office, Extended European Search Report issued in International Application No. 20202064.0-1110, dated Apr. 21, 2021 (14 pages).

Dupuis J., et al., "Endothelin Receptor Antagonists in Pulmonary Arterial Hypertension," European Respiratory Journal, Respiratory Society, GB, vol. 31, No. 2, Jan. 31, 2008, pp. 407-415 (9 pages).

Buckley M., et al., "Phosphodiesterase-5 Inhibitors in Management of Pulmonary Hypertension: Safety, Tolerability, and Efficacy," Drug, Healthcare and Patient Safety, Dove Medical Press Ltd., GB, vol. 2, Jan. 1, 2010. pp. 151-161 (11 pages).

Japanese Patent Office, Notice of Reasons for Rejection issued in Japanese Patent Application No. 2020-178704 and English-language Translation dated Sep. 1, 2021 (11 pages).

Guarino, V. R., "The Molecular Design of Prodrugs by Functional Group," edited by Jarkko Rautio, Products and Targeted Delivery: Towards Better ADME Properties, vol. 47, Dec. 15, 2010, p. 3 (3 pages).

TREPROSTINIL DERIVATIVE COMPOUNDS AND METHODS OF USING SAME

CROSS REFERENCE TO RELATED APPLICATIONS

This application is a continuation-in-part application of U.S. application Ser. No. 14/153,498 filed on Jan. 13, 2014, which claims priority to U.S. Provisional Application No. 61/751,608 filed on Jan. 11, 2013, each of which is incorporated herein by reference in its entirety for all purposes.

BACKGROUND

Pulmonary hypertension (PH) or pulmonary arterial hypertension (PAH) is a disease which can result in death and is characterized by increased pulmonary artery pressure and pulmonary vascular resistance. A need exists for better compounds and methods for treating PH and PAH. See, for example, US Patent Publication No. 2013/0274261. Many valuable pharmacologically active compounds, including some of interest with respect to PH and PAH, cannot be effectively administered orally for various reasons and are generally administered via intravenous or intramuscular routes. These routes of administration generally require intervention by a physician or other health care professional, and can entail considerable discomfort as well as potential local trauma to the patient. One example of such a compound is treprostinil and derivatives thereof, which has been used in the treatment of PH and PAH. See, for example, WO 2005/007081. Treprostinil (herein also called Compound A) has the following structure:

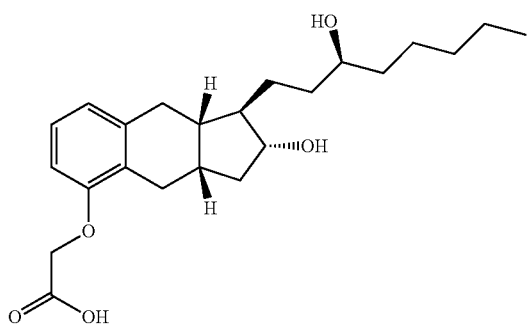 [SMILES: CCCCC[C@H](O)CC[C@@H]1[C@H]2Cc3cccc(OCC(=O)O)c3C[C@H]2C[C@H]1O]

Treprostinil can exist as a salt, such as a sodium salt.

Accordingly, there is a clinical need in providing treprostinil by improved formulations and methods, e.g., either orally or transdermally. More particularly, there is a need for a safe and effective method for increasing the systemic availability of treprostinil via administration of treprostinil or derivatives (including prodrugs) or analogs thereof.

The application of transdermal drug delivery technology to the administration of a wide variety of drugs has been proposed and various systems for accomplishing this are disclosed in numerous technical journals and patents. U.S. Pat. Nos. 3,598,122; 4,144,317; 4,201,211; 4,262,003; and 4,379,454, all of which are incorporated herein by reference, are representative of various transdermal drug delivery systems of the prior art, which systems have the ability of delivering controlled amounts of drugs to patients for extended periods of time ranging in duration from several hours to several days. None of the above patents describes a transdermal delivery system which is intended to deliver treprostinil or its derivatives.

SUMMARY

Embodiments described herein include compounds, compositions, and devices, as well as methods of making and methods of using the same.

One embodiment provides a compound represented by Formula (I)

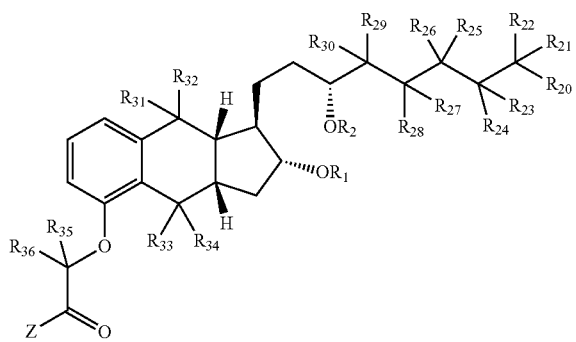

wherein, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —OH, —OR$_{11}$, —N(R$_{11}$)R$_{12}$, —SR$_{11}$, or P$_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

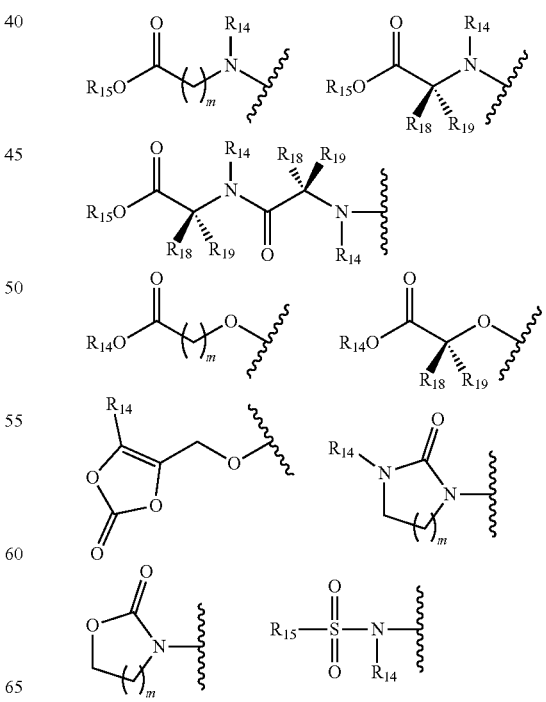

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the group consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein at least one of $R_1$ and $R_2$ is $P_2$, wherein $P_2$ is selected from the group consisting of:

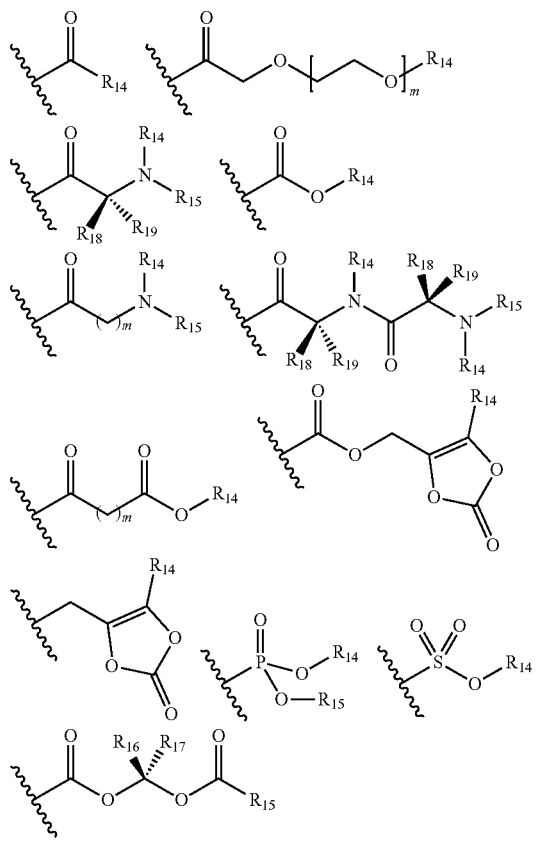

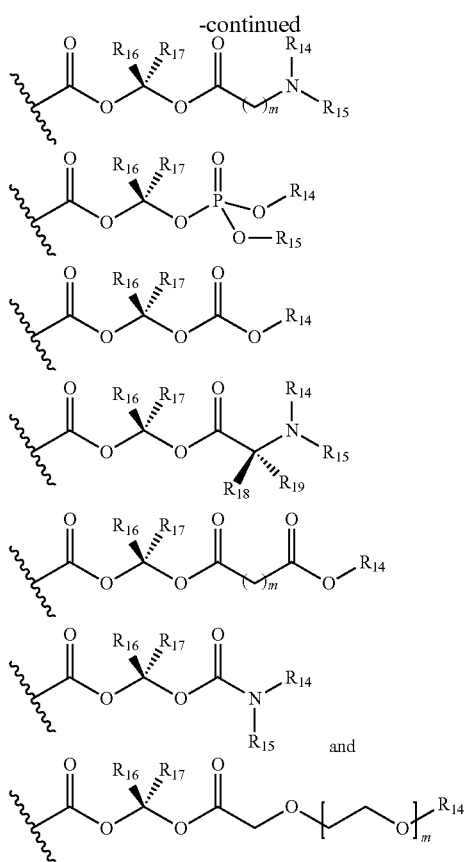

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, solvates and polymorphs of the compounds of Formula I.

In another embodiment, the parameters of Formula I are defined as follows:

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —OR$_{11}$, —N(R$_{11}$)R$_{12}$, —SR$_{11}$, or P$_1$;

$R_{11}$ is branched alkyl, haloalkyl, halocycloalkyl, heteroalkyl, substituted heteroalkyl, cycloheteroalkyl, substituted cycloheteroalkyl, bicycloalkyl, alkylcycloalkyl, substituted alkylcycloalkyl, alkylcycloheteroalkyl, substituted alkylcycloheteroalkyl, alkylaryl, substituted alkylaryl, heteroaryl, substituted heteroaryl, alkylheteroaryl, or substituted alkylheteroaryl;

$R_{12}$ is H, branched alkyl, haloalkyl, heteroalkyl, cycloheteroalkyl, alkylcycloalkyl, alkylcycloheteroalkyl, aryl, or heteroaryl;

$P_1$ is selected from the group consisting of:

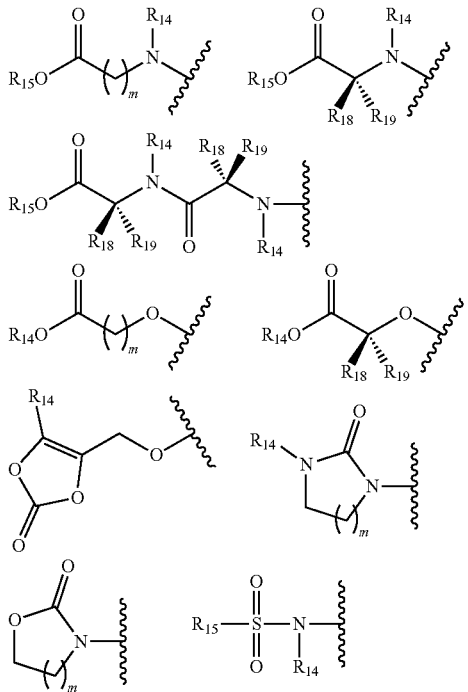
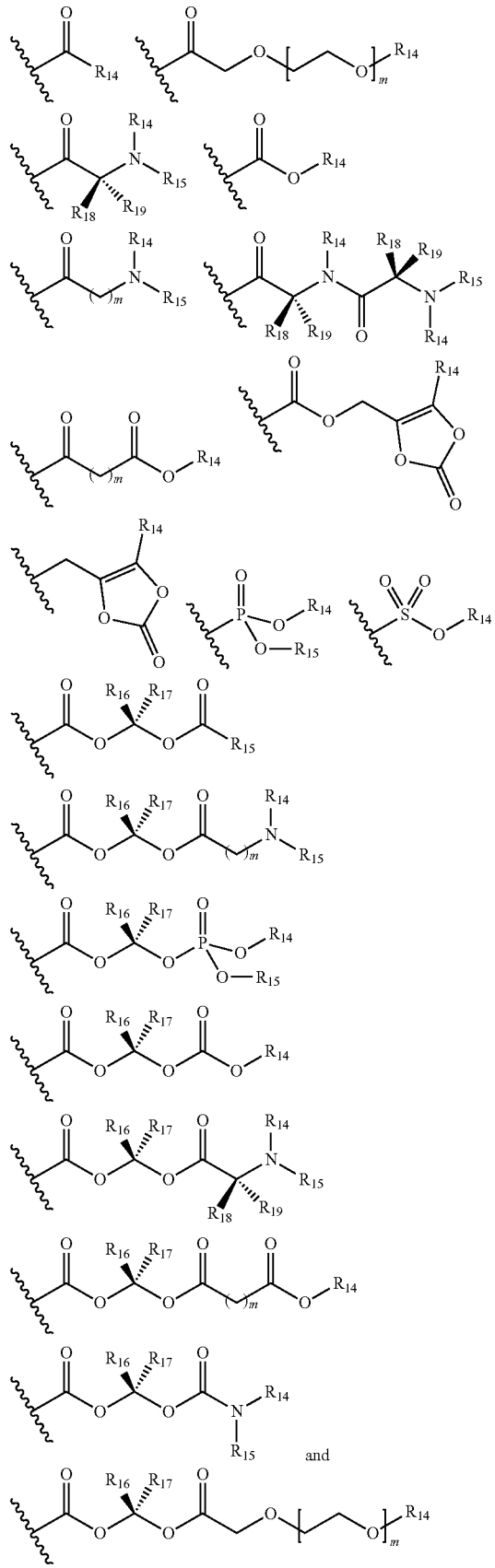

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the group consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein $P_2$ is selected from the group consisting of:

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, solvates and polymorphs of the compounds of Formula I.

In another embodiment, provided is a compound represented by Formula II:

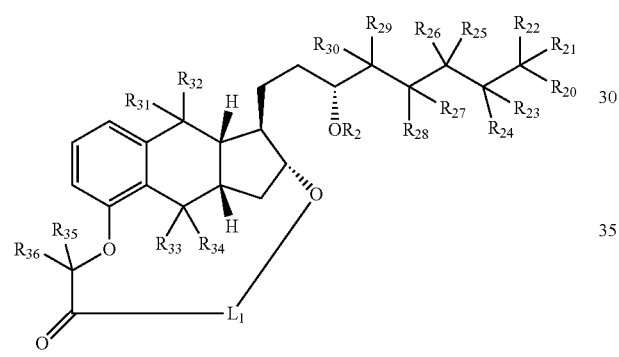

wherein, $R_2$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

$L_1$ is selected from the group consisting of —O-alkylene-C(O)—, —O-alkylene-OC(O)—, or a bond; wherein $P_2$ is selected from the group consisting of:

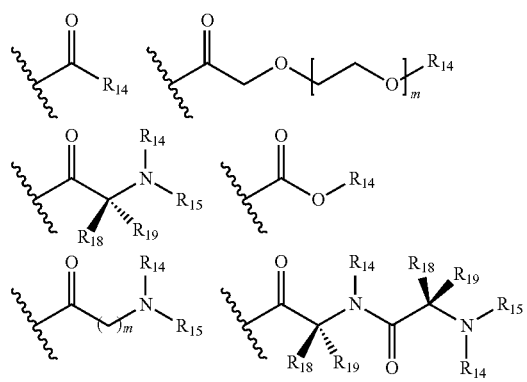

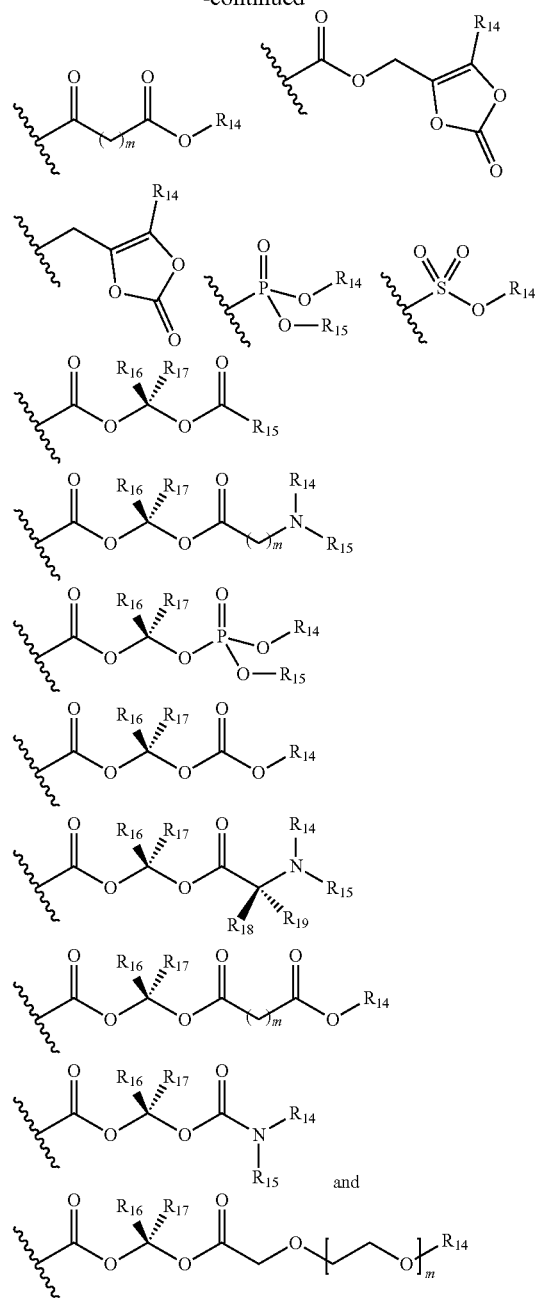

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula H includes enantiomers, pharmaceutically acceptable salts, solvates and polymorphs of the compounds of Formula II.

In another embodiment, a compound is represented by Formula III:

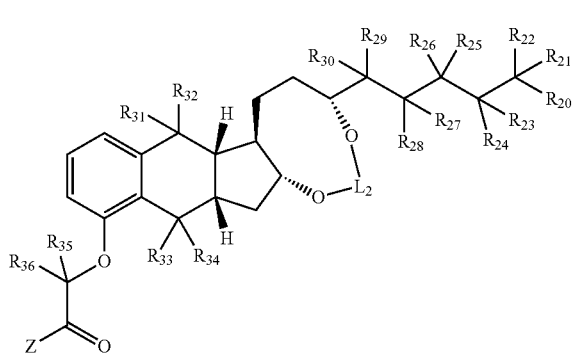

wherein $L_2$ is selected from the group consisting of —$CH_2$—, —CHMe-, —$C(Me)_2$- and the following:

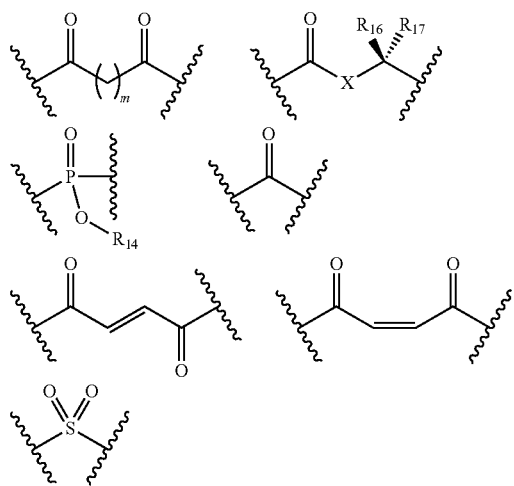

wherein, m is 1, 2, 3, or 4;

X is $NR_{14}$ or O;

$R_{14}$ is selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{16}$ and $R_{17}$ are independently in each occurrence H or alkyl; $R_{16}$ and $R_{17}$ taken together with the atoms to which they attach optionally form a 3- to 6-membered ring; and $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

wherein Z is —OH, —$OR_{11}$, —$N(R_{11})R_{12}$, —$SR_{11}$, or $P_1$; $R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

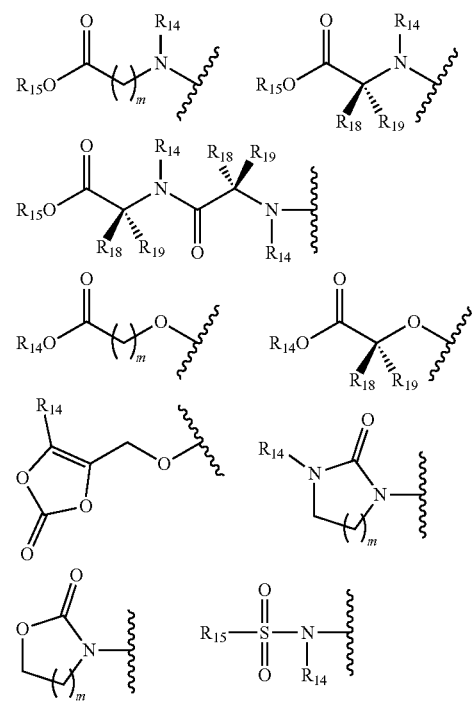

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the group consisting of halo, hydroxy, alkoxy, amino, thio, methylthio, —C(O)OH, —C(O)O-(alkyl), —$CONH_2$, aryl, and heteroaryl, wherein the aryl or heteroaryl is unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

wherein Formula III includes enantiomers, pharmaceutically acceptable salts, solvates and polymorphs of the compounds of Formula III.

Another embodiment provides a compound represented by Formula IV:

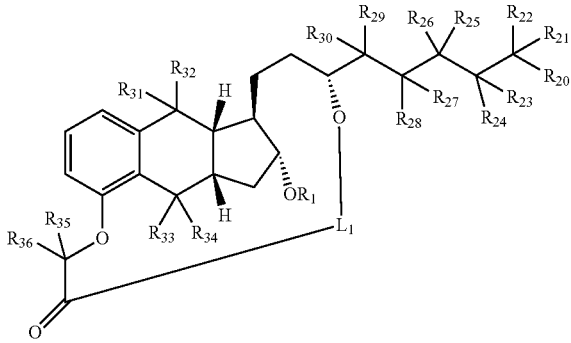

wherein, $R_1$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

$L_1$ is selected from the group consisting of —O-alkylene-C(O)—, —O-alkylene-OC(O)—, or a bond;

wherein $P_2$ is selected from the group consisting of:

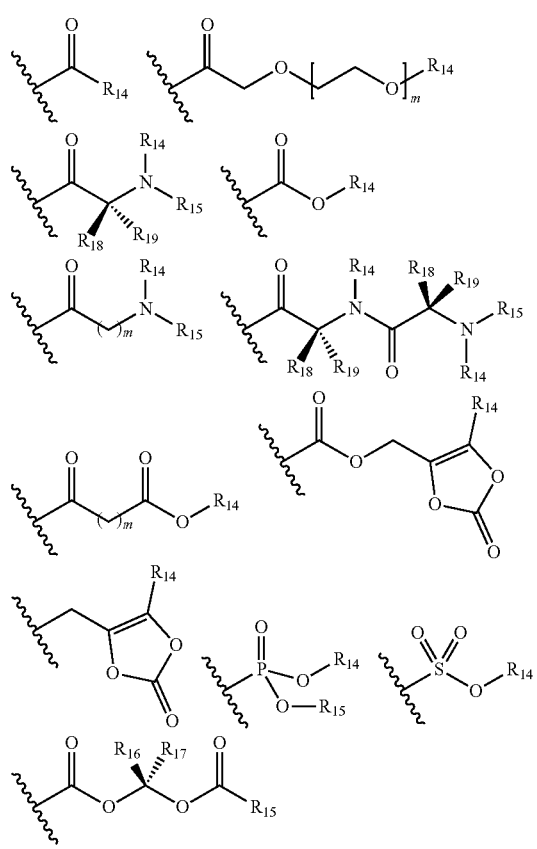

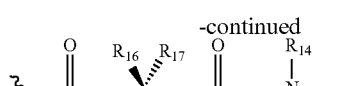
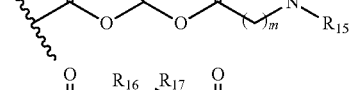
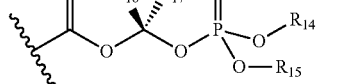
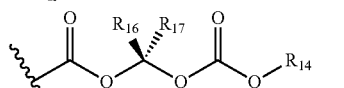
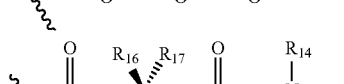
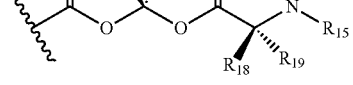
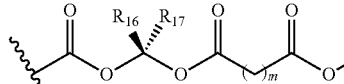

and

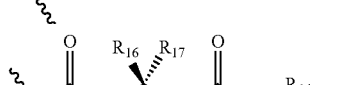

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are independently in each occurrence selected from the group consisting of hydrogen and alkyl, wherein the alkyl is unsubstituted or substituted with 1 substituent selected from the group consisting of halo, hydroxy, alkoxy, amino, thio, methylthio, —C(O)OH, —C(O)O-(alkyl), —CONH$_2$, aryl, and heteroaryl, wherein the aryl or heteroaryl is unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula IV includes enantiomers, pharmaceutically acceptable salts, solvates and polymorphs of the compounds of Formula IV.

Compositions are also provided including compositions comprising at least one compound according to Formula I, II, III or IV and at least one other component. In one embodiment, the composition is formulated for transdermal delivery. In another embodiment, the composition is formulated for transdermal delivery with a patch. In one embodiment, the composition can further comprise at least one solvent. In one embodiment, the amount of the compound according to Formula I, II, III or IV is adapted to provide a useful delivery profile for treatment of a human. In one embodiment, the treatment is carried out on a subject, such as a mammal, but the subject is not a human.

At least one advantage for at least one embodiment includes ability to tailor the chemical structure of a pharmaceutically useful motif for particular uses including treatment and prophylactic use against, for example, PH and PAH. For example, the drug delivery profile can be adapted for a particular application.

At least one additional advantage for at least one embodiment includes ability to use the compounds to provide better bioavailability including use in transdermal drug delivery applications.

DETAILED DESCRIPTION

Introduction

Priority U.S. provisional application 61/751,608 filed Jan. 11, 2013 is incorporated herein by reference in its entirety for all purposes including the chemical formulae and claims, including Formula I, Formula II, and Formula III, as well as Schemes 1-4, examples, and the tables of structures on pages 14-16.

Various prostacyclin analogs, including treprostinil, and methods for their use are known. For example, they can be used in promoting vasodilation, inhibiting platelet aggregation and thrombus formation, stimulating thrombolysis, inhibiting cell proliferation (including vascular remodeling), providing cytoprotection, and preventing atherogenesis and inducing angiogenesis. Through these prostacyclin-mimetic mechanisms, these compounds may be used in the treatment of/for: pulmonary hypertension, ischemic diseases (e.g., peripheral vascular disease, Raynaud's phenomenon, scleroderma, myocardial ischemia, ischemic stroke, renal insufficiency), heart failure (including congestive heart failure), conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation, and other emerging therapeutic areas where prostacyclin treatment appears to have a beneficial role. These compounds may also demonstrate additive or synergistic benefit in combination with other cardiovascular agents (e.g., calcium channel blockers, phosphodiesterase inhibitors, endothelial antagonists, and antiplatelet agents).

Treprostinil is a chemically stable analog of prostacyclin. Although treprostinil sodium (Remodulin®) is approved by the Food and Drug Administration (FDA) for subcutaneous administration, treprostinil as the free acid has an absolute oral bioavailability of less than 10% and a very short systemic half life due to significant metabolism.

Definitions

Herein, listings of chemical groups represented by multiple chemical formulae are provided (e.g., $P_1$, $P_2$, $L_1$, and $L_2$). As used herein, these group listings also describe any combination of subgroups of the chemical formulae in the group listing as well as any single formula in the group listing.

The term "alkyl" refers to a monovalent saturated hydrocarbon group. $C_1$-$C_8$ alkyl is an alkyl having from 1 to 8 carbon atoms and includes, for example, $C_1$-$C_3$ alkyl, $C_1$-$C_5$ alkyl, and $C_1$-$C_7$ alkyl. An alkyl may be linear or branched. Examples of alkyl groups include methyl, ethyl, n-propyl, isopropyl, n-butyl, isobutyl, sec-butyl, t-butyl, n-pentyl, isopentyl, neopentyl and n-hexyl.

The term "haloalkyl" refers to a monovalent saturated hydrocarbon group attached to a one or more halogen atoms selected from Cl and F. Specific examples include 2-fluoroethyl, 2,2-difluoroethyl, 2-fluoropropyl, and 2,2-difluoropropyl.

The term "heteroalkyl" refers to a monovalent saturated hydrocarbon group attached to one or more heteroatoms selected from O, N, and S. $C_1$-$C_8$ heteroalkyl is an alkyl having from 1 to 8 carbon atoms and one or more heteroatoms selected from O, N and S, and includes, for example, $C_1$-$C_3$—OH, $C_1$-$C_5$—SH, and $C_1$-$C_7$—NH$_2$. It also includes C1-C2-O—C3-C4-OH, and C1-C2-NH—C3-C4-OH.

The term "cycloalkyl" refers to a monocyclic, bicyclic, or tricyclic monovalent saturated hydrocarbon ring system. The term "$C_3$-$C_{14}$ cycloalkyl" refers to a cycloalkyl wherein the number of ring carbon atoms is from 3 to 14. Examples of $C_3$-$C_{14}$ cycloalkyl include $C_3$-$C_{10}$ cycloalkyl and $C_3$-$C_6$ cycloalkyl. Bicyclic and tricyclic ring systems include fused, bridged and spirocyclic ring systems. More particular examples of cycloalkyl groups include cyclopropyl, cyclobutyl, cyclopentyl, cyclohexyl, cycloheptyl, cis- and trans-decalynil, norbornyl, adamantyl, and spiro[4.5]decanyl.

The term "cycloheteroalkyl" or "heterocycloalkyl" refers to a monocyclic, bicyclic, or tricyclic monovalent saturated ring system wherein from 1 to 4 ring atoms are heteroatoms independently selected from the group consisting of O, N and S. The term "3- to 14-membered cycloheteroalkyl" refers to a cycloheteroalkyl wherein the number of ring atoms is from 3 to 14. Examples of 3- to 14-membered cycloheteroalkyl include 3- to 10-membered cycloheteroalkyl and 3- to 6-membered cycloheteroalkyl. Bicyclic and tricyclic ring systems include fused, bridged and spirocyclic ring systems. More particular examples of cycloheteroalkyl groups include azepanyl, azetidinyl, aziridinyl, imidazolidinyl, morpholinyl, oxazolidinyl, piperazinyl, piperidinyl, pyrazolidinyl, pyrrolidinyl, quinuclidinyl, tetrahydrofuranyl, thiomorpholinyl, and alpha-methyl-1,3-dioxol-2-onyl.

The term "alkylcycloalkyl" refers to a monocyclic, bicyclic, or tricyclic monovalent saturated hydrocarbon ring system linked to an alkyl group. Particular examples include cyclopropylmethyl, cyclopropylethyl, and cyclohexylethyl.

The term "alkylheterocycloalkyl" or "alkylcycloheteroalkyl" refers to a cycloheteroalkyl group attached to an alkyl group. Specific examples include N-ethylmorpholine. N-ethylpiperidine, 4-ethylpiperidine, 1-methyl-4-ethylpiperidine, and N-ethylpiperazine.

The term "aryl" refers to a monovalent aromatic carbocyclic ring system, which may be a monocyclic, fused bicyclic, or fused tricyclic ring system. The term "$C_6$-$C_{14}$ aryl" refers to an aryl having from 6 to 14 ring carbon atoms. An example of $C_6$-$C_{14}$ aryl is $C_6$-$C_{10}$ aryl. More particular examples of aryl groups include phenyl, naphthyl, anthracyl, and phenanthryl.

The term "heteroaryl" refers to an unsaturated aromatic heterocyclyl radical. Examples of heteroaryl radicals include unsaturated 3- to 6-membered heteromonocyclic groups containing 1 to 4 nitrogen atoms, for example, pyrrolyl, pyrrolinyl, imidazolyl, tetrazolyl, etc.; unsaturated condensed heterocyclyl groups containing 1 to 5 nitrogen atoms, for example, indolyl, isoindolyl, benzimidazolyl, quinolyl, benzotrazolyl, tetrazolopyridazinyl, etc.; unsaturated 3- to 6-membered heteromonocyclic groups containing 1 to 2 oxygen atoms and 1 to 3 nitrogen atoms, for example, oxazolyl, oxadiazolyl, etc.; unsaturated condensed heterocyclyl groups containing 1 to 2 oxygen atoms and 1 to 3 nitrogen atoms; unsaturated 3- to 6-membered heteromonocyclic groups containing 1 to 2 sulfur atoms and 1 to 3 nitrogen atoms, for example, thiazolyl, thiadiazolyl, etc.; and unsaturated condensed heterocyclyl groups containing 1 to 2 sulfur atoms and 1 to 3 nitrogen atoms.

The term "alkylaryl" refers to an aryl-substituted alkyl radical such as benzyl, diphenylmethyl or phenylethyl.

The term "alkylheteroaryl" refers to a heteroaryl-substituted alkyl radical such as imidazoylmethyl, thiazoylmethyl or pyridylethyl.

The terms described herein such as alkyl, haloalkyl, heteroalkyl, cycloalkyl, cycloheteroalkyl, alkylcycloalkyl, alkylheterocycloalkyl, aryl, heteroaryl, alkylaryl, and alkylheteroary, are understood to cover optionally embodiments wherein they form rings. For example, optionally groups such as $R_{14}$, $R_{15}$, $R_{16}$, $R_{17}$, $R_{18}$, and $R_{19}$ can form rings with other $R_{14}$, $R_{15}$, $R_{16}$, $R_{17}$, $R_{18}$, and $R_{19}$ groups.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, alkylsulfonyl, alkylsulfonylalkyl, alkoxy, alkoxy, aryloxy, aminocarbonyl, alkylaminocarbonyl, arylaminocarbonyl, alkoxycarbonyl, aryloxycarbonyl, alkylhalo, amino, trifluoromethyl, cyano, nitro, alkylamino, arylamino, alkylaminoalkyl, arylaminoalkyl, hydroxyl, alkyloxyalkyl, carboxyalkyl, alkoxycarbonylalkyl, aminocarbonylalkyl, acyl, carbonyl, carboxylic acid, sulfonic acid, phosphonic acid, aryl, heteroaryl, heterocyclic, and aliphatic. It is understood that the substituent may be further substituted within the normal limits of the skilled artisan. A moiety or group may be optionally substituted which means the group may or may not have one or more substituents.

The term "compound" as used herein is also intended to include salts, solvates, hydrates and polymorphs thereof. The specific recitation of "salt", "solvate", "hydrate" or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable base addition salt or acid addition salt.

The term "pharmaceutically acceptable" refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide and hydrochloric, hydrobromic, hydroiodic, sulfuric and phosphoric acids, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acids, and related inorganic and organic acids. Pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of a solvent such as water, acetone, ethanol, methanol, dichloromethane, 2-propanol, or the like, bound by non-covalent intermolecular forces.

Isotopes and Isotopic Abundance

It will be recognized that some variation of natural isotopic abundance occurs in a synthesized compound depending upon the origin of chemical materials used in the synthesis. Thus, a preparation of treprostinil will inherently contain small amounts of deuterated isotopologues. The concentration of naturally abundant stable hydrogen and carbon isotopes, notwithstanding this variation, is small and immaterial with respect to the degree of stable isotopic substitution of compounds of this invention. See, for instance, Wada E et al, *Seikagaku* 1994, 66:15; Ganes L Z et al, *Comp Biochem Physiol Mol Integr Physiol* 1998, 119: 725. In a compound of this invention, when a particular position is designated as having deuterium, it is understood that the abundance of deuterium at that position is substantially greater than the natural abundance of deuterium, which is about 0.015%. A position designated as having deuterium typically has a minimum isotopic enrichment factor of at least about 3000 (about 45% deuterium incorporation) at each atom designated as deuterium in said compound.

The term "isotopic enrichment factor" as used herein means the ratio between the isotopic abundance and the natural abundance of a specified isotope.

In some embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

In other embodiment, a compound of the invention contains less than 10%, preferably less than 6%, and more preferably less than 3% of all other isotopologues combined, including a form that lacks any deuterium. In certain aspects, the compound contains less than "X"% of all other isotopologues combined, including a form that lacks any deuterium; where X is any number between 0 and 10 (e.g., 1, 0.5, 0.001), inclusive. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen present in the active, free base form of the compound of Formula I or II, and do not include the isotopic composition of hydrolysable portions of prodrugs, or of counterions.

The term "isotopologue" refers to species that differ from a specific compound of this invention only in the isotopic composition of their molecules or ions.

Stereoisomers

It is understood that the present invention encompasses all possible stereoisomers, including all possible diastereomers and enantiomers, of the compounds described herein, and not only the specific stereoisomers as indicated by drawn structure or nomenclature. Some embodiments of the invention relate to the specific stereoisomers indicated by drawn structure or nomenclature.

Core Structure Formula I

In one embodiment, the invention provides a compound represented by Formula I:

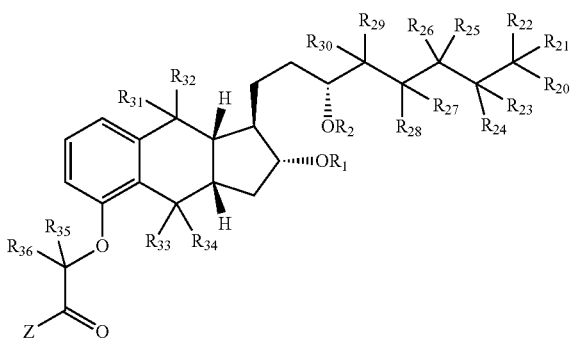

At least two sub-embodiments are provided to define further Formula I.

In a first sub-embodiment of Formula I, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —OH, —OR$_{11}$, —N(R$_{11}$)R$_{12}$, —SR$_{11}$, or P$_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from the group consisting of:

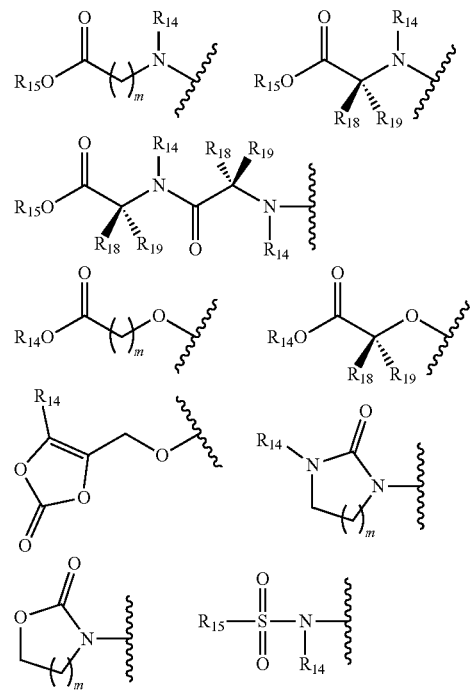

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the group consisting of halo, hydroxy, alkoxy, amino, thio, methylthio, —C(O)OH, —C(O)O-(alkyl), —CONH$_2$, aryl, and heteroaryl, wherein the aryl or heteroaryl are unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein at least one of $R_1$ and $R_2$ is $P_2$, wherein $P_2$ is selected from the group consisting of:

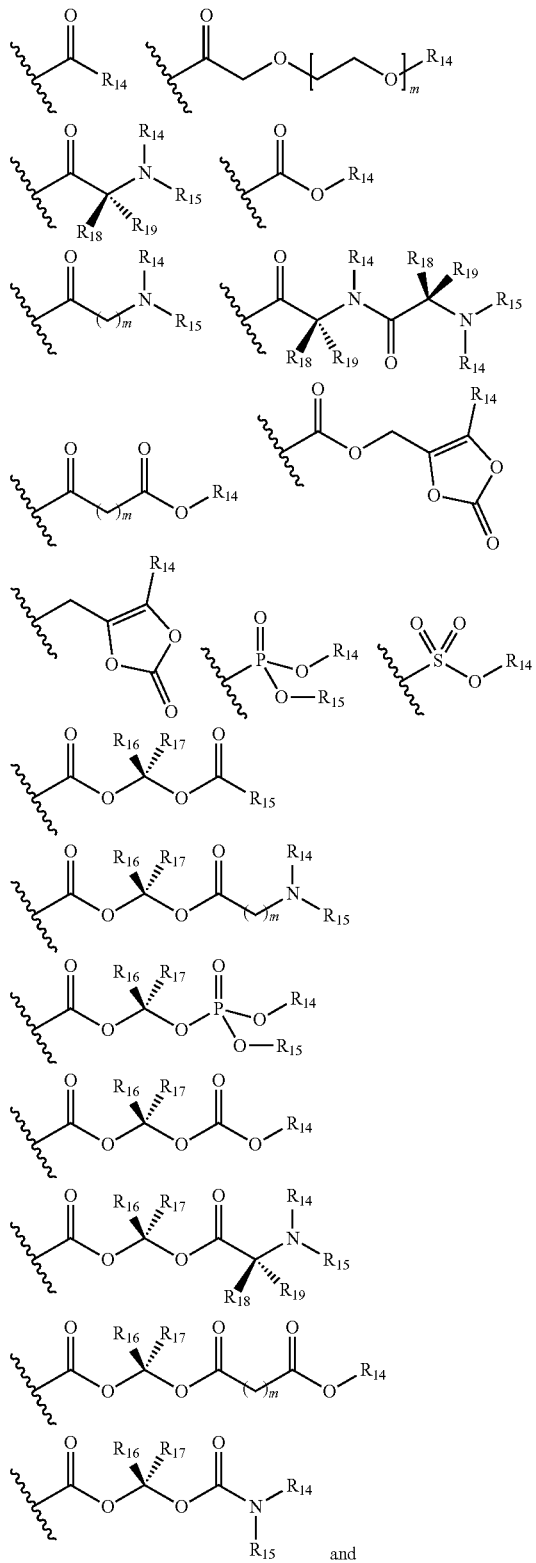

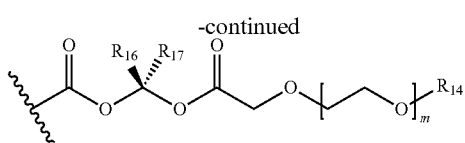
-continued wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, solvates and polymorphs of the compounds of Formula I. In this Formula I, the Z, $R_1$, and $R_2$ groups are not linked to each other, in contrast to Formulae II, III, and IV described herein.

In one embodiment, $R_1$ is $P_2$ and $R_2$ is H. In another embodiment, $R_1$ is H and $R_2$ is $P_2$. In another embodiment, $R_1$ is $P_2$ and $R_2$ is $P_2$.

The group $P_2$ can be more particularly described. In one embodiment, $P_2$ is selected from the group consisting of:

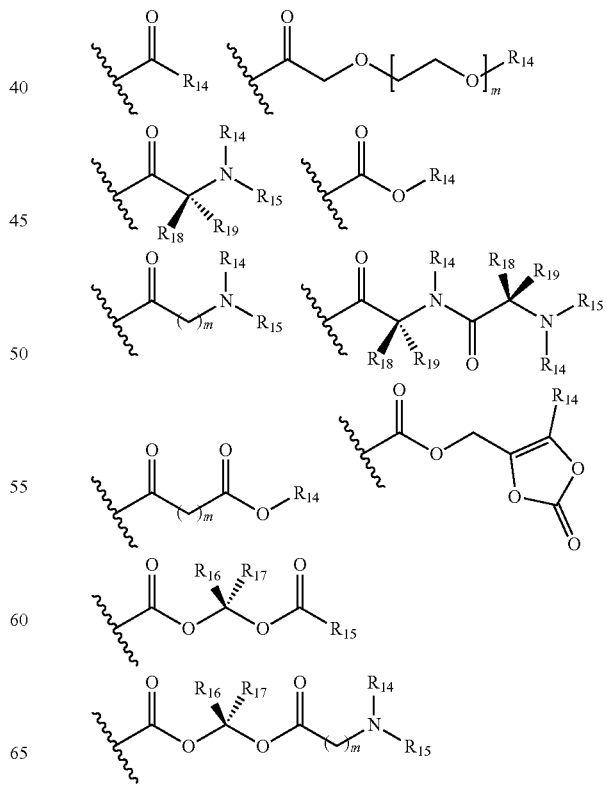

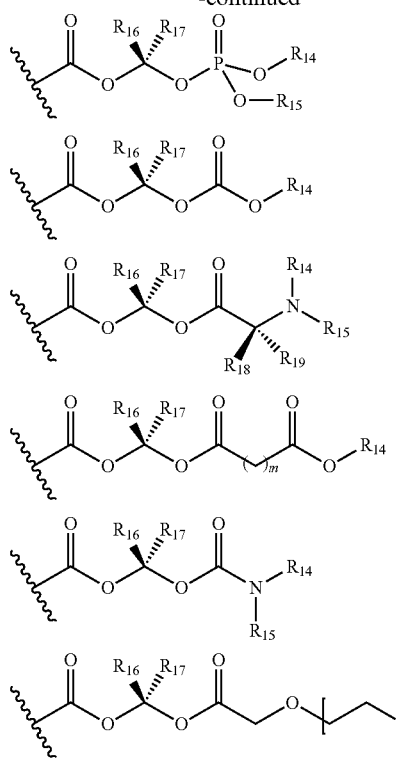
In another embodiment, P$_2$ is selected from the group consisting of:
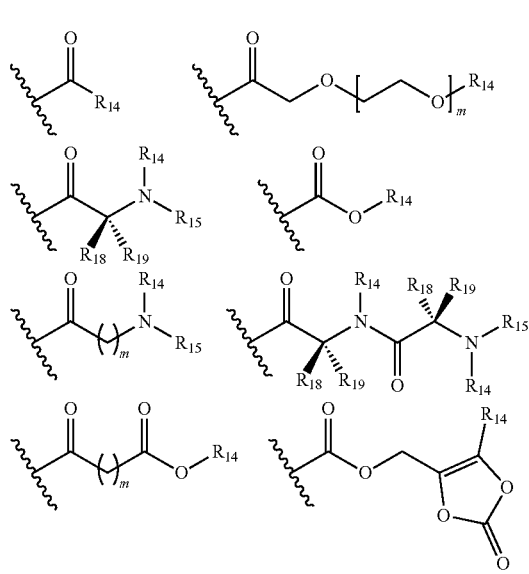
In another embodiment, P$_2$ is selected from the group consisting of:
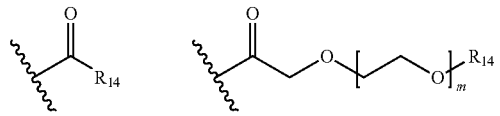
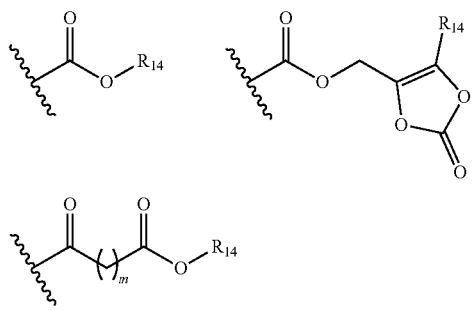
In another embodiment, P$_2$ is selected from the group consisting of:
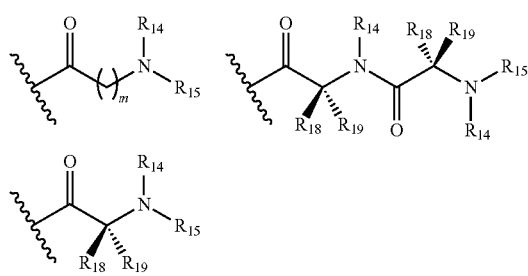
In another embodiment, P$_2$ is selected from the group consisting of:
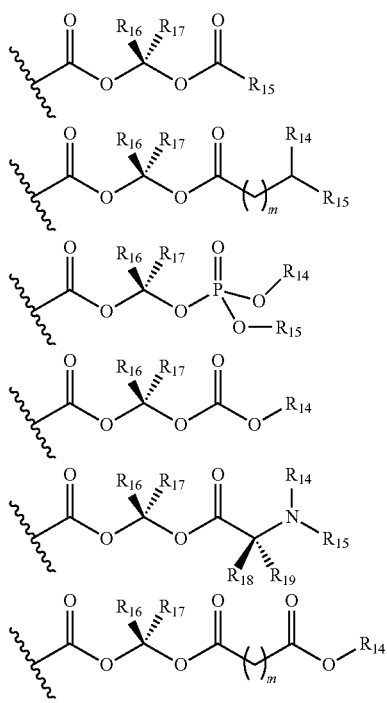
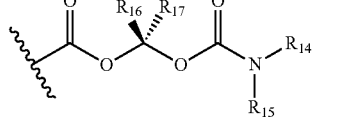

-continued

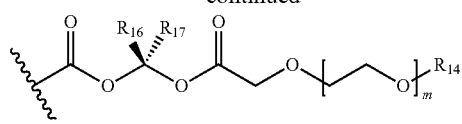

In another embodiment, $P_2$ is selected from the group consisting of:

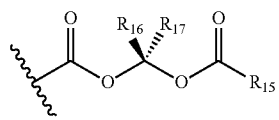

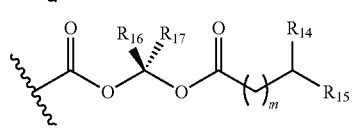

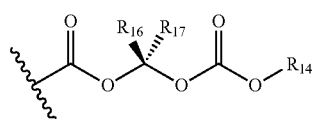

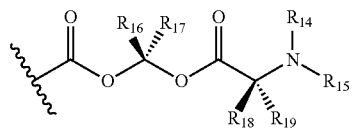

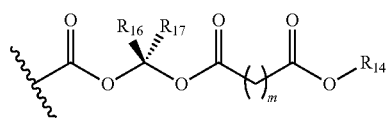

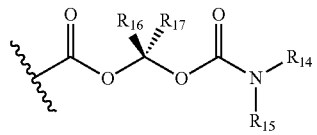

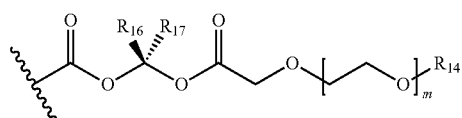

In another embodiment, $P_2$ is selected from the group consisting of:

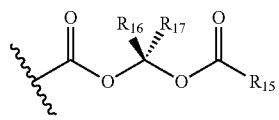

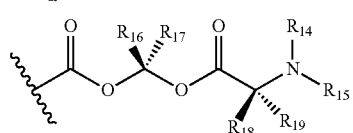

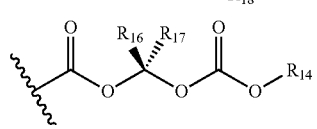

-continued

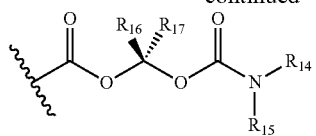

In another embodiment, $P_2$ is selected from the group consisting of:

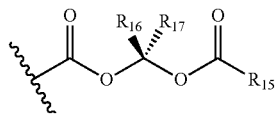

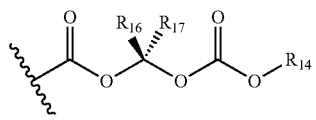

In another embodiment, $P_2$ is selected from the group consisting of:

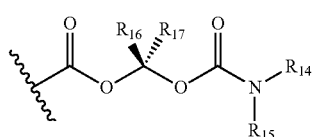

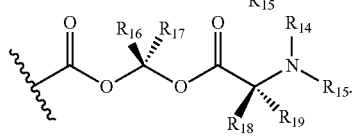

In another embodiment, $P_2$ is selected from the group consisting of:

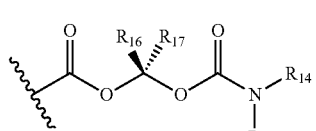

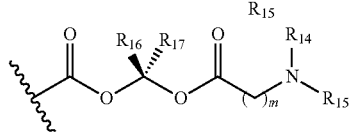

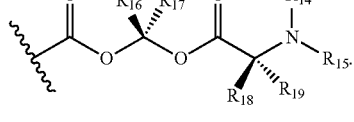

In another embodiment, $P_2$ is selected from the group consisting of:

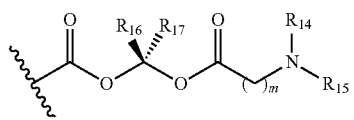

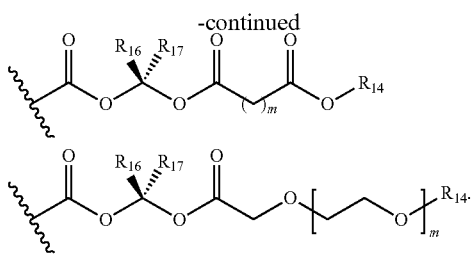

In one embodiment, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are H.

In one embodiment, Z is —$OR_{11}$, —$N(R_{11})R_{12}$, or $P_1$. In another embodiment, Z is $P_1$. In another embodiment, Z is —OH, —$OR_{11}$, —$N(R_{11})R_{12}$, or $P_1$. In another embodiment, Z is —OH.

In one embodiment, Z is not —OH and $R_{11}$ is not unsubstituted or substituted benzyl.

In a second sub-embodiment of Formula I, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently H or deuterium;

Z is —$OR_{11}$, —$N(R_{11})R_{12}$, —$SR_{11}$; or $P_1$;

$R_{11}$ is branched alkyl, haloalkyl, halocycloalkyl, heteroalkyl, substituted heteroalkyl, cycloheteroalkyl, substituted cycloheteroalkyl, bicycloalkyl, alkylcycloalkyl, substituted alkylcycloalkyl, alkylcycloheteroalkyl, substituted alkylcycloheteroalkyl, alkylaryl, substituted alkylaryl, heteroaryl, substituted heteroaryl, alkylheteroaryl, or substituted alkylheteroaryl;

$R_{12}$ is H, branched alkyl, haloalkyl, heteroalkyl, cycloheteroalkyl, alkylcycloalkyl, alkylcycloheteroalkyl, aryl, or heteroaryl;

$P_1$ is selected from the group consisting of:

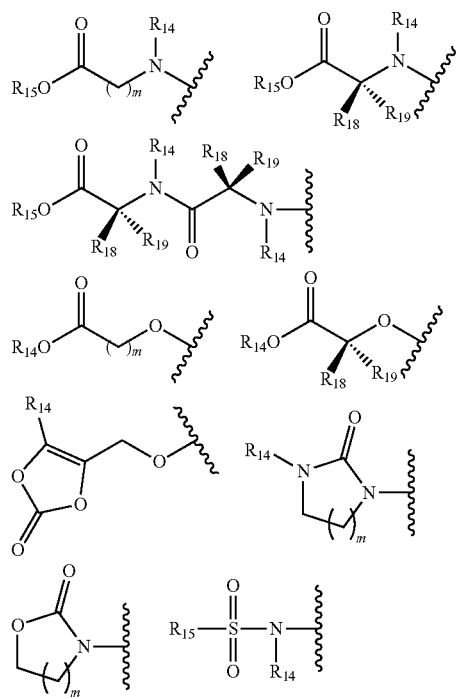

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the group consisting of halo, methyl, and methoxy;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —$CONH_2$, aryl, and heteroaryl, wherein the aryl or heteroaryl is unsubstituted or substituted from the group consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

$R_{15}$ and $R_{18}$ taken together with the atoms to which they attach optionally form a 5- to 7-membered ring;

$R_{15}$ and $R_{19}$ taken together with the atoms to which they attach optionally form a 5- to 7-membered ring;

and, $R_1$ and $R_2$ are independently H or $P_2$, wherein $P_2$ is selected from the group consisting of:

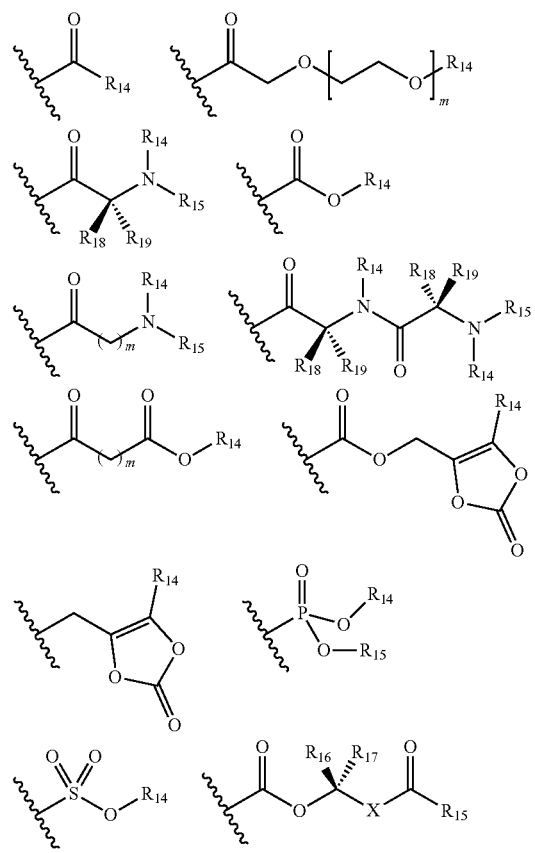

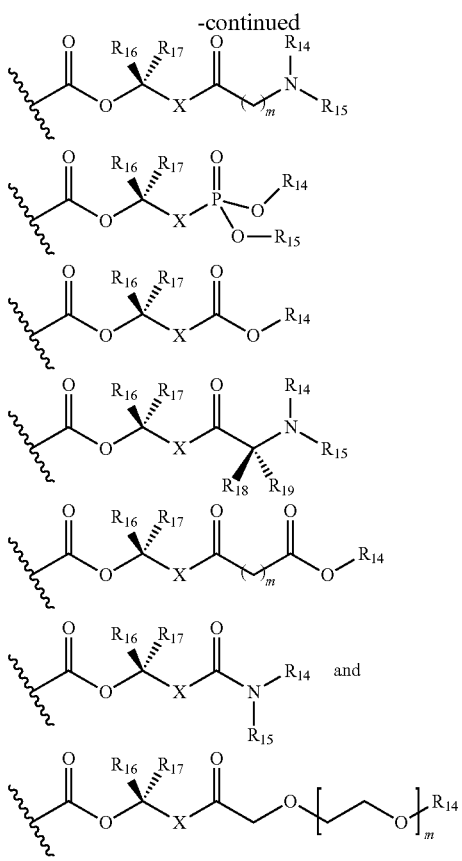

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O, or S, which is unsubstituted or substituted with 1, 2, or 3 substituents independently selected from the list consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula I includes enantiomers, pharmaceutically acceptable salts, solvates and polymorphs of the compounds of Formula I.

In one embodiment, Z is —$OR_{11}$. In one embodiment, Z is —$N(R_{11})R_{12}$. In one embodiment, Z is —$SR_{11}$. In one embodiment, Z is $P_1$. In one embodiment, Z is $OR_{11}$ and $R_{11}$ is bicycloalkyl, alkylcycloalkyl, or alkylcycloheteroalkyl. In one embodiment, Z is $P_1$.

In one embodiment, $R_{11}$ is haloalkyl, or more particularly, fluoroalkyl.

In one embodiment, $R_1$ is hydrogen or $R_2$ is hydrogen. In one embodiment, $R_1$ is hydrogen and $R_2$ is $P_2$. In one embodiment, $R_1$ is $P_2$ and $R_2$ is hydrogen. In one embodiment, $R_1$ and $R_2$ are hydrogen. In one embodiment, $R_1$ and $R_2$ are $P_2$.

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ is deuterium.

In one embodiment, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are hydrogen.

Formula IA

A sub-embodiment of formula I is a compound represented by Formula (IA):

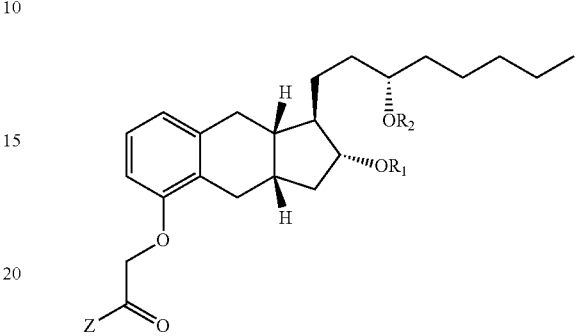

wherein,

Z is —OH, —$OR_{11}$, or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, or substituted alkylcycloheteroalkyl;

$P_1$ is selected from the group consisting of:

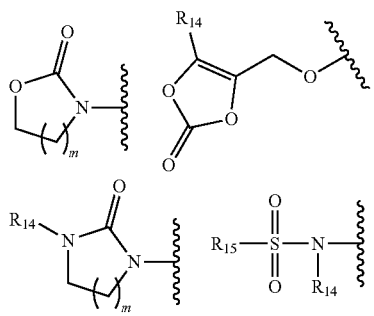

wherein, m is 1, 2, 3, or 4;

$R_{14}$ is selected from the group consisting of H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl;

and, $R_1$ and $R_2$ are independently H or $P_2$, wherein at least one of $R_1$ and $R_2$ is $P_2$, wherein $P_2$ is selected from the group consisting of:

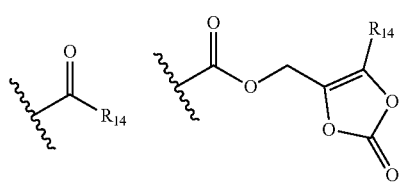

-continued

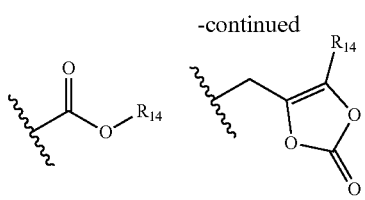

wherein,

R$_{14}$ and R$_{15}$ are independently in each occurrence selected from the group consisting of H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl;

R$_{14}$ and R$_{15}$ taken together with the atoms to which they attach optionally form a 5- to 7-membered ring;

wherein Formula IA includes enantiomers, pharmaceutically acceptable salts, solvates and polymorphs of the compounds of Formula IA.

Examples of Compounds of Formula I

The following are specific compounds of Formula I (noting Compound A is treprostinil):

Compound A

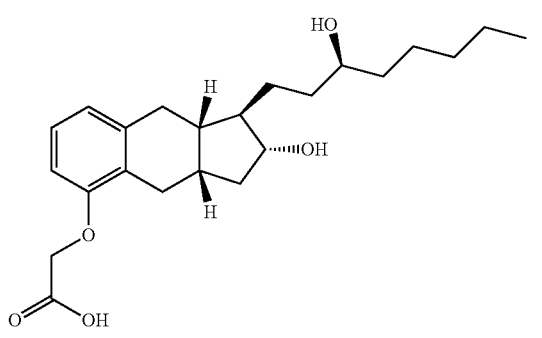

[2-Hydroxy-1-(3-hydroxy-octyl)-2,3,3a,4,9,9a-hexahydro-1H-cyclopenta[b]naphthalen-5-yloxy]-acetic acid Compound 1

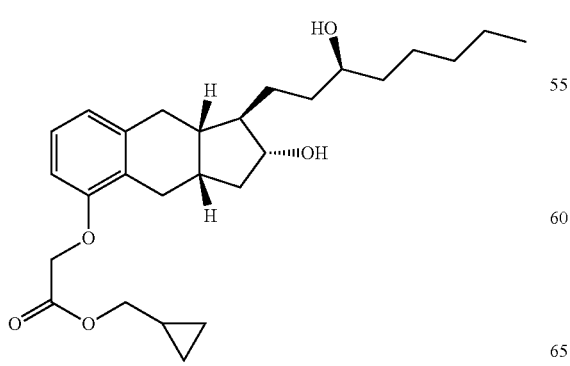

[2-Hydroxy-1-(3-hydroxy-octyl)-2,3,3a,4,9,9a-hexahydro-1H-cyclopenta[b]naphthalen-5-yloxy]-acetic acid cyclopropylmethyl ester (all Possible Stereoisomers, Including Compound 1)

Compound 2

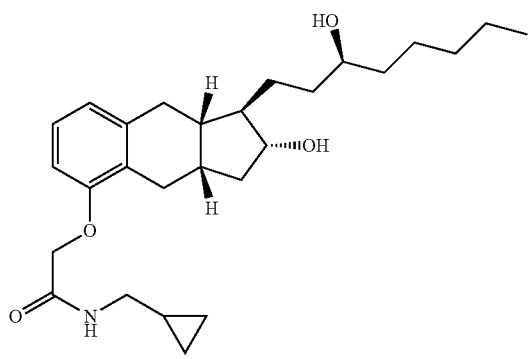

N-Cyclopropylmethyl-2-[2-hydroxy-1-(3-hydroxy-octyl)-2,3,3a,4,9,9a-hexahydro-1H-cyclopenta[b]naphthalen-5-yloxy]-acetamide (all Possible Stereoisomers, Including Compound 2)

Compound 3

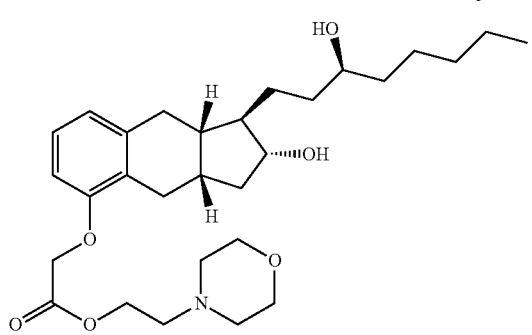

[2-Hydroxy-1-(3-hydroxy-octyl)-2,3,3a,4,9,9a-hexahydro-1H-cyclopenta[b]naphthalen-5-yloxy]-acetic acid 2-morpholin-4-yl-ethyl ester (all Possible Stereoisomers, Including Compound 3)

Compound 4

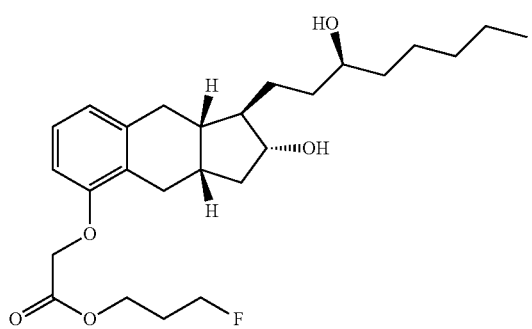

[2-Hydroxy-1-(3-hydroxy-octyl)-2,3,3a,4,9,9a-hexa-hydro-1H-cyclopenta[b]naphthalen-5-yloxy]-acetic acid 3-fluoro-propyl ester (all Possible Stereoisomers, Including Compound 4)

N-(2-Hydroxy-ethyl)-2-[2-hydroxy-1-(3-hydroxy-octyl)-2,3,3a,4,9,9a-hexahydro-1H-cyclopenta[b]naphthalen-5-yloxy]-acetamide (all Possible Stereoisomers, Including Compound 7)

Compound 5

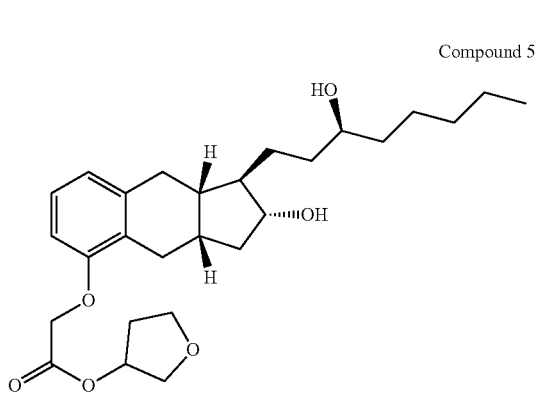 [SMILES: CCCCC[C@H](O)CC[C@@H]1[C@H]2Cc3cccc(OCC(=O)OC4CCOC4)c3C[C@H]2C[C@H]1O]

Compound 8

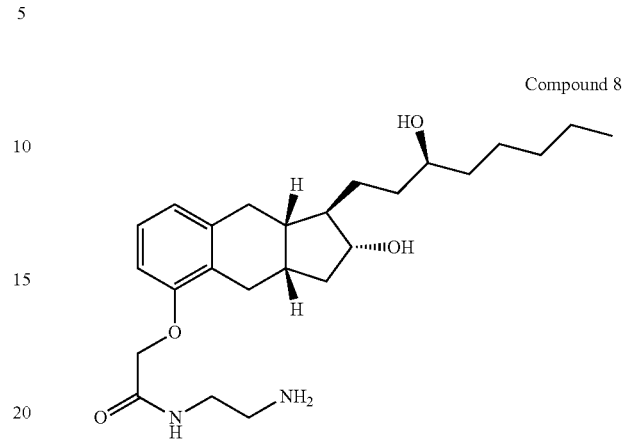

[2-Hydroxy-1-(3-hydroxy-octyl)-2,3,3a,4,9,9a-hexa-hydro-1H-cyclopenta[b]naphthalen-5-yloxy]-acetic acid tetrahydro-furan-3-yl ester (all Possible Stereoisomers, Including Compound 5)

N-(2-Amino-ethyl)-2-[2-hydroxy-1-(3-hydroxy-octyl)-2,3,3a,4,9,9a-hexahydro-1H-cyclopenta[b]naphthalen-5-yloxy]-acetamide (all Possible Stereoisomers, Including Compound 8)

Compound 6

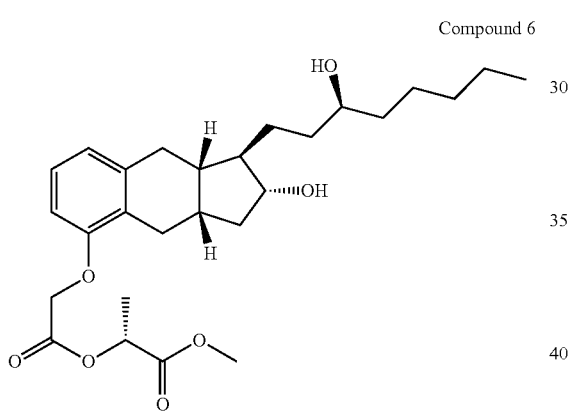

Compound 9

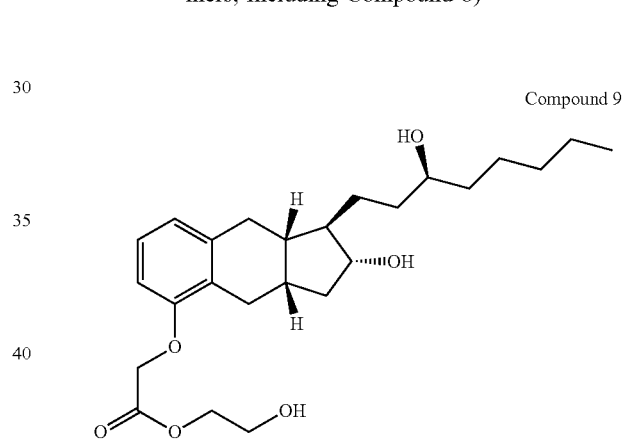

2-{2-[2-Hydroxy-1-(3-hydroxy-octyl)-2,3,3a,4,9,9a-hexahydro-1H-cyclopenta[b]naphthalen-5-yloxy]-acetoxy}-propionic acid methyl ester (all Possible Stereoisomers, Including Compound 6)

[2-Hydroxy-1-(3-hydroxy-octyl)-2,3,3a,4,9,9a-hexa-hydro-1H-cyclopenta[b]naphthalen-5-yloxy]-acetic acid 2-hydroxy-ethyl ester (all Possible Stereoisomers, Including Compound 9)

Compound 7

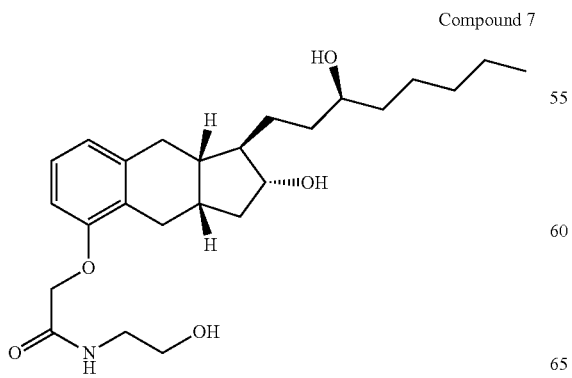

Compound 10

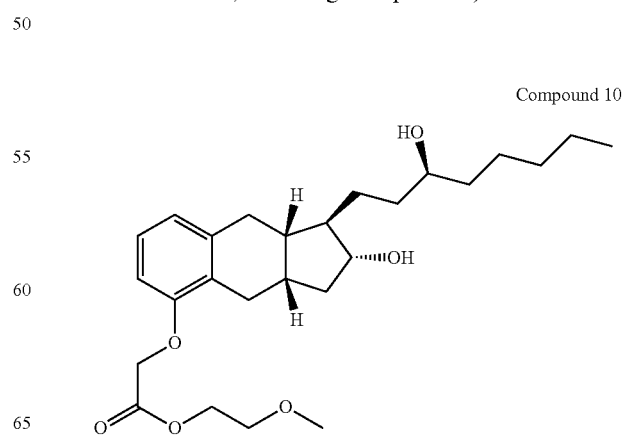

33

[2-Hydroxy-1-(3-hydroxy-octyl)-2,3,3a,4,9,9a-hexa-hydro-1H-cyclopenta[b]naphthalen-5-yloxy]-acetic acid 2-methoxy-ethyl ester (all Possible Stereoisomers, Including Compound 10)

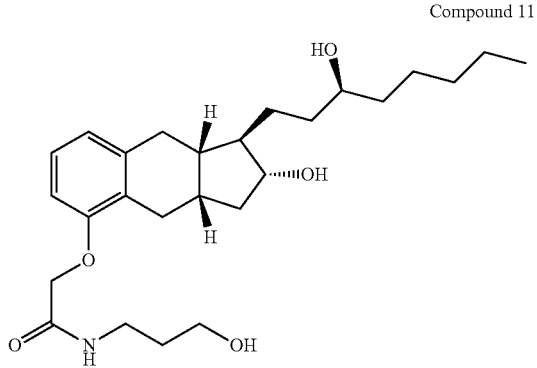 [SMILES: CCCCC[C@H](O)CC[C@@H]1[C@H]2Cc3cccc(OCC(=O)NCCCO)c3C[C@H]2C[C@H]1O]

Compound 11

2-[2-Hydroxy-1-(3-hydroxy-octyl)-2,3,3a,4,9,9a-hexahydro-1H-cyclopenta[b]naphthalen-5-yloxy]-N-(3-hydroxy-propyl)-acetamide (all Possible Stereoisomers, Including Compound 11)

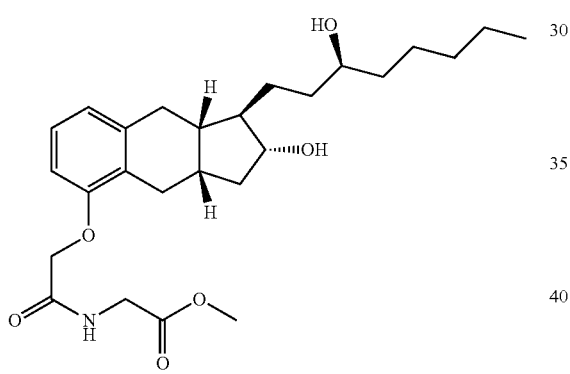

Compound 12

{2-[2-Hydroxy-1-(3-hydroxy-octyl)-2,3,3a,4,9,9a-hexahydro-1H-cyclopenta[b]naphthalen-5-yloxy]-acetylamino}-acetic acid methyl ester (all Possible Stereoisomers, Including Compound 12)

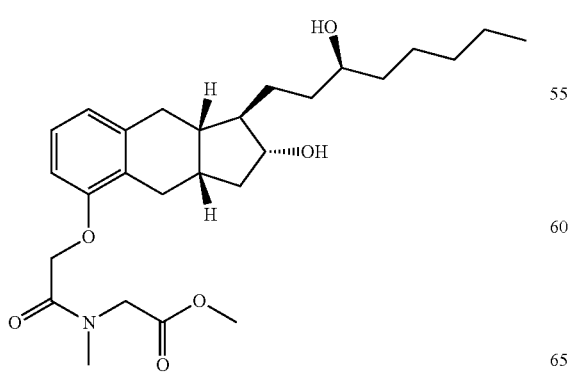

Compound 13

34

({2-[2-Hydroxy-1-(3-hydroxy-octyl)-2,3,3a,4,9,9a-hexahydro-1H-cyclopenta[b]naphthalen-5-yloxy]-acetyl}-methyl-amino)-acetic acid methyl ester (all Possible Stereoisomers, Including Compound 13)

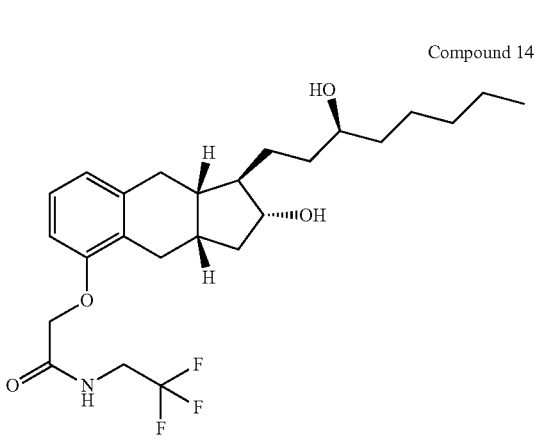 [SMILES: CCCCC[C@H](O)CC[C@@H]1[C@H]2Cc3cccc(OCC(=O)NCC(F)(F)F)c3C[C@H]2C[C@H]1O]

Compound 14

2-[2-Hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide (all Possible Stereoisomers, Including Compound 14)

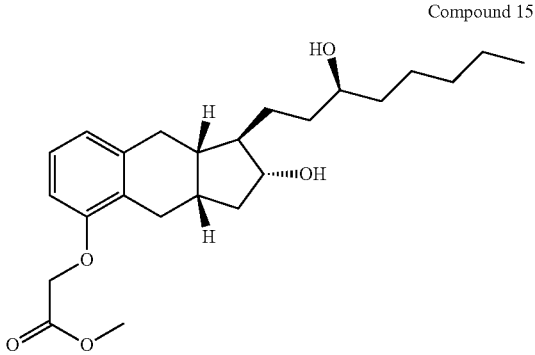 [SMILES: CCCCC[C@H](O)CC[C@@H]1[C@H]2Cc3cccc(OCC(=O)OC)c3C[C@H]2C[C@H]1O]

Compound 15

[2-Hydroxy-1-(3-hydroxy-octyl)-2,3,3a,4,9,9a-hexahydro-1H-cyclopenta[b]naphthalen-5-yloxy]-acetic acid methyl ester (all Possible Stereoisomers, Including Compound 15)

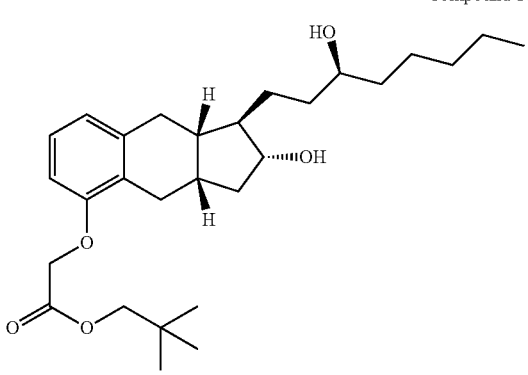

Compound 16

35

[2-Hydroxy-1-(3-hydroxy-octyl)-2,3,3a,4,9,9a-hexahydro-1H-cyclopenta[b]naphthalen-5-yloxy]-acetic acid 2,2-dimethyl-propyl ester (all Possible Stereoisomers, Including Compound 16)

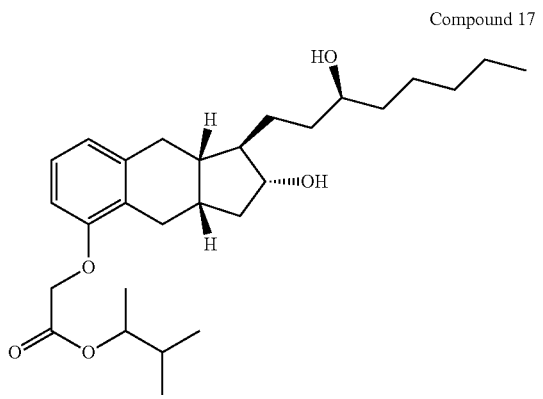 [SMILES: CCCCC[C@H](O)CC[C@@H]1[C@H]2Cc3cccc(OCC(=O)OC(C)C(C)C)c3C[C@H]2C[C@H]1O]

Compound 17

[2-Hydroxy-1-(3-hydroxy-octyl)-2,3,3a,4,9,9a-hexahydro-1H-cyclopenta[b]naphthalen-5-yloxy]-acetic acid 1,2-dimethyl-propyl ester (all Possible Stereoisomers, Including Compound 17)

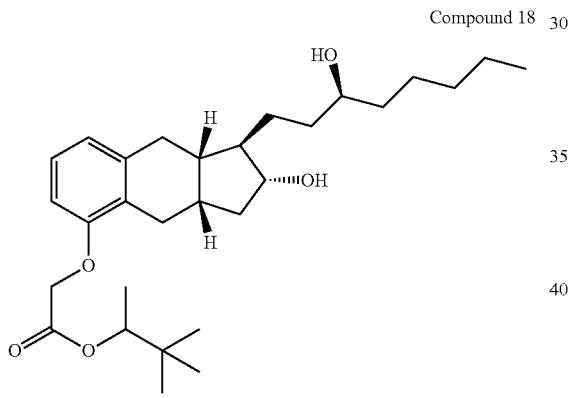

Compound 18

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester (all Possible Stereoisomers, Including Compound 18)

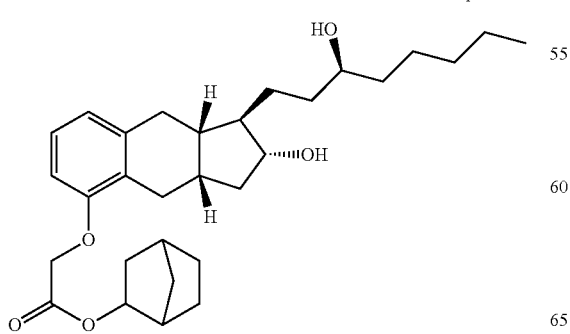

Compound 19

36

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester (all Possible Stereoisomers, Including Compound 19)

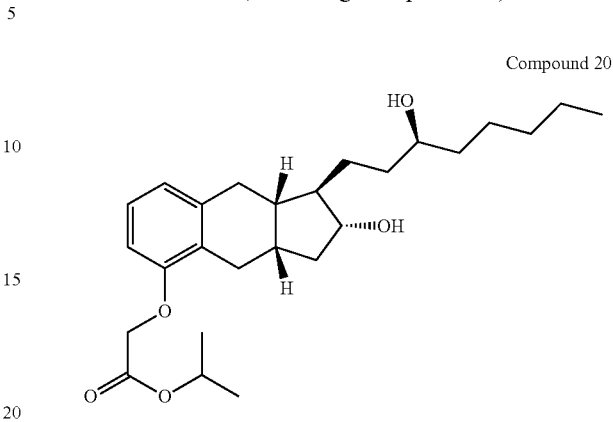

Compound 20

[2-Hydroxy-1-(3-hydroxy-octyl)-2,3,3a,4,9,9a-hexahydro-1H-cyclopenta[b]naphthalen-5-yloxy]-acetic acid isopropyl ester (all Possible Stereoisomers, Including Compound 20)

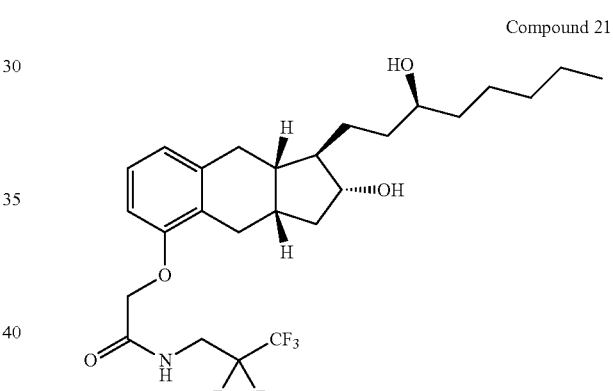

Compound 21

2-[2-Hydroxy-1-(3-hydroxy-octyl)-2,3,3a,4,9,9a-hexahydro-1H-cyclopenta[b]naphthalen-5-yloxy]-N-(2,2,3,3,3-pentafluoro-propyl)-acetamide (all Possible Stereoisomers, Including Compound 21)

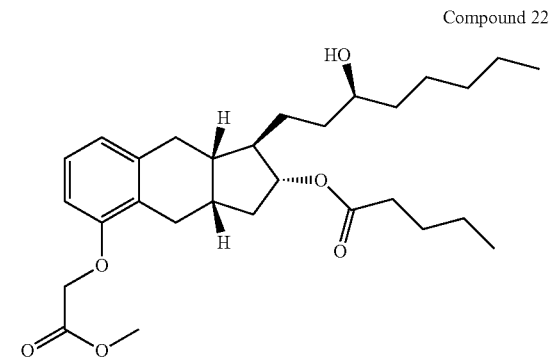 [SMILES: CCCCC[C@H](O)CC[C@@H]1[C@H]2Cc3cccc(OCC(=O)OC)c3C[C@H]2C[C@H]1OC(=O)CCCC]

Compound 22

37

Pentanoic acid 1-(3-hydroxy-octyl)-5-methoxycarbonylmethoxy-2,3,3a,4,9,9a-hexahydro-1H-cyclopenta[b]naphthalen-2-yl ester (all Possible Stereoisomers, Including Compound 22)

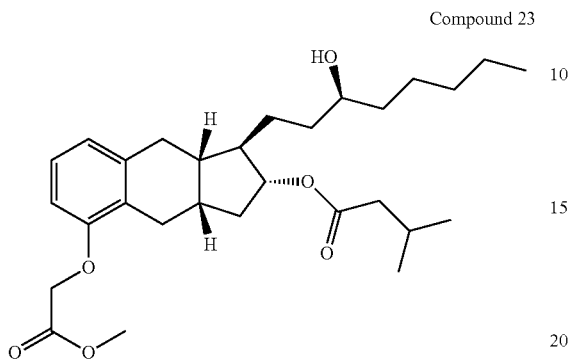

Compound 23

3-Methyl-butyric acid 1-(3-hydroxy-octyl)-5-methoxycarbonylmethoxy-2,3,3a,4,9,9a-hexahydro-1H-cyclopenta[b]naphthalen-2-yl ester (all Possible Stereoisomers, Including Compound 23)

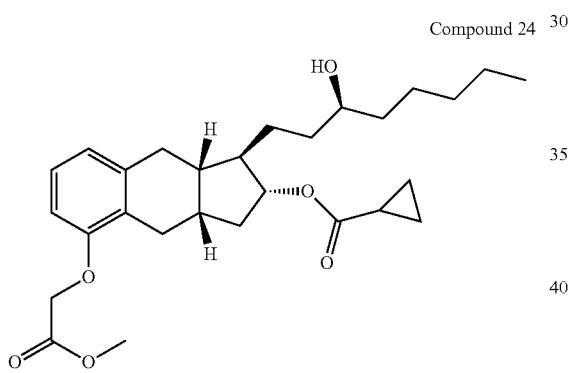

Compound 24

Cyclopropanecarboxylic acid 1-(3-hydroxy-octyl)-5-methoxycarbonylmethoxy-2,3,3a,4,9,9a-hexahydro-1H-cyclopenta[b]naphthalen-2-yl ester (all Possible Stereoisomers, Including Compound 24)

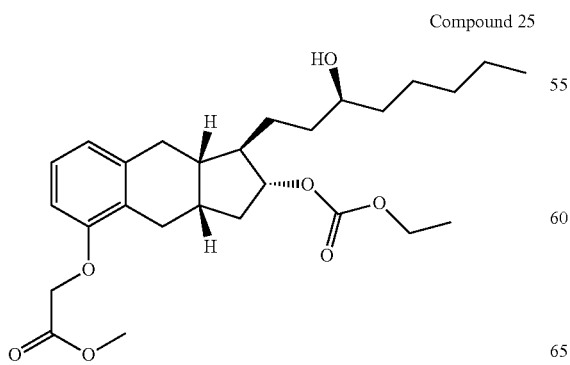

Compound 25

38

[2-Ethoxycarbonyloxy-1-(3-hydroxy-octyl)-2,3,3a,4,9,9a-hexahydro-1H-cyclopenta[b]naphthalen-5-yloxy]-acetic acid methyl ester (all Possible Stereoisomers, Including Compound 25)

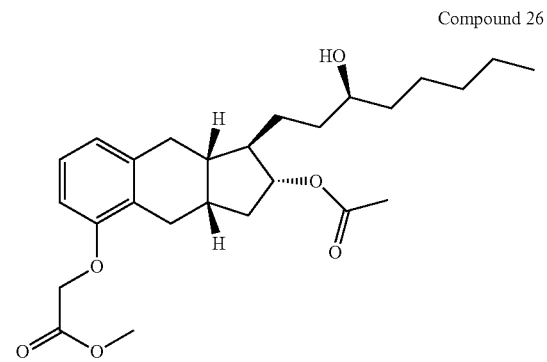 [SMILES: CCCCC[C@H](O)CC[C@@H]1[C@H]2Cc3cccc(OCC(=O)OC)c3C[C@H]2C[C@H]1OC(C)=O]

Compound 26

[2-Acetoxy-1-(3-hydroxy-octyl)-2,3,3a,4,9,9a-hexahydro-1H-cyclopenta[b]naphthalen-5-yloxy]-acetic acid methyl ester (all Possible Stereoisomers, Including Compound 26)

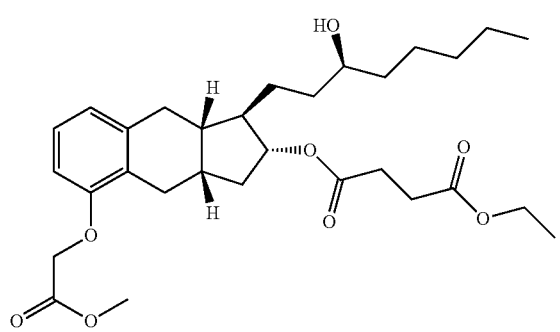

Compound 27

Succinic acid ethyl ester 1-(3-hydroxy-octyl)-5-methoxycarbonylmethoxy-2,3,3a,4,9,9a-hexahydro-1H-cyclopenta[b]naphthalen-2-yl ester (all Possible Stereoisomers, Including Compound 27)

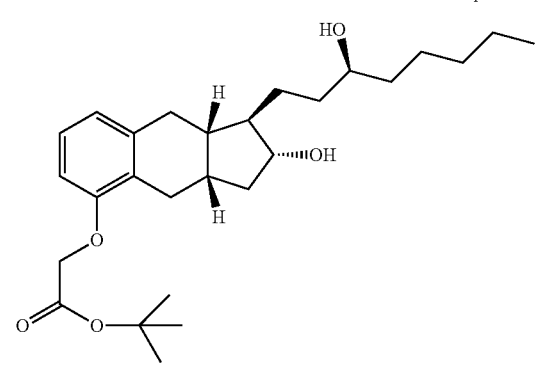

Compound 28

39

[2-Hydroxy-1-(3-hydroxy-octyl)-2,3,3a,4,9,9a-hexahydro-1H-cyclopenta[b]naphthalen-5-yloxy]-acetic acid tert-butyl ester (all Possible Stereoisomers, Including Compound 28)

Compound 29

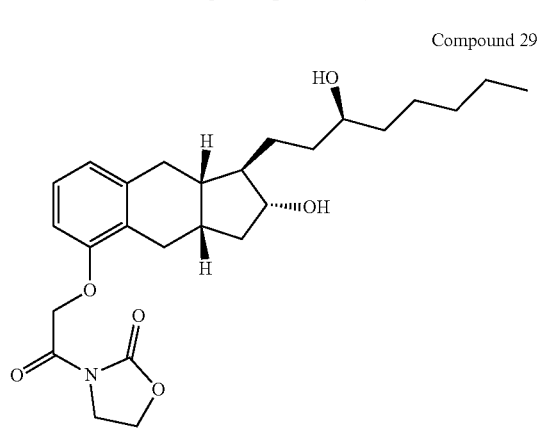 [SMILES: CCCCC[C@H](O)CC[C@@H]1[C@H]2Cc3cccc(OCC(=O)N4CCOC4=O)c3C[C@H]2C[C@H]1O]

3-{2-[2-Hydroxy-1-(3-hydroxy-octyl)-2,3,3a,4,9,9a-hexahydro-1H-cyclopenta[b]naphthalen-5-yloxy]-acetyl}-oxazolidin-2-one (all Possible Stereoisomers, Including Compound 29)

Compound 30

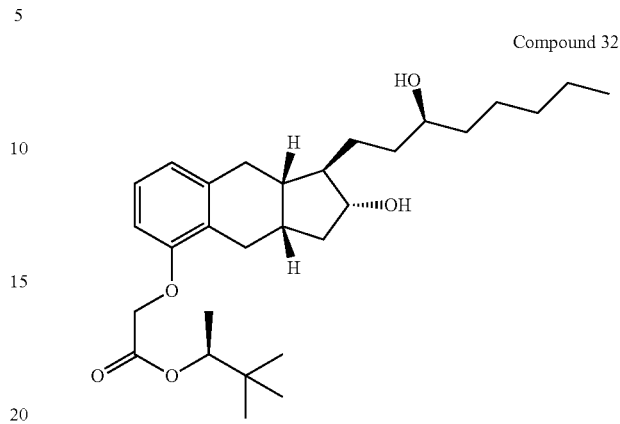

2-[2-Hydroxy-1-(3-hydroxy-octyl)-2,3,3a,4,9,9a-hexahydro-1H-cyclopenta[b]naphthalen-5-yloxy]-N-(1H-tetrazol-5-yl)-acetamide (all Possible Stereoisomers, Including Compound 30)

Compound 31

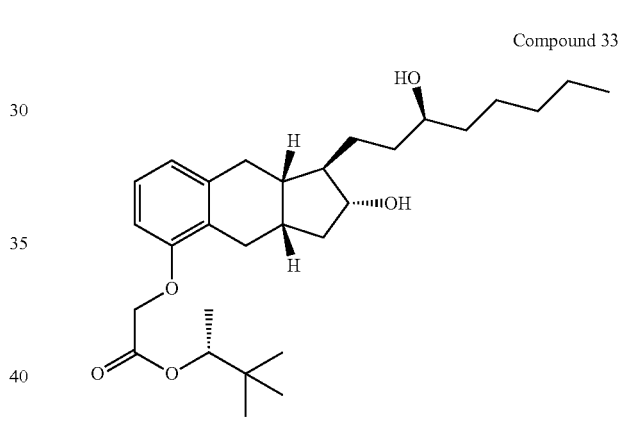

40

[2-Hydroxy-1-(3-hydroxy-octyl)-2,3,3a,4,9,9a-hexahydro-1H-cyclopenta[b]naphthalen-5-yloxy]-acetic acid 2,2,2-trifluoro-1,1-dimethyl-ethyl ester (all Possible Stereoisomers, Including Compound 31)

Compound 32

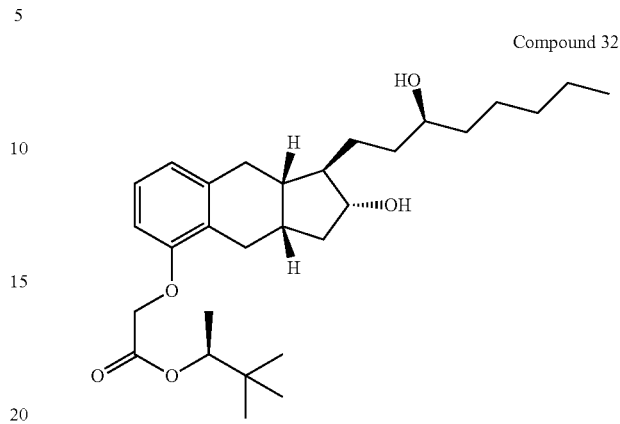

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester (all Possible Stereoisomers, Including Compound 32)

Compound 33

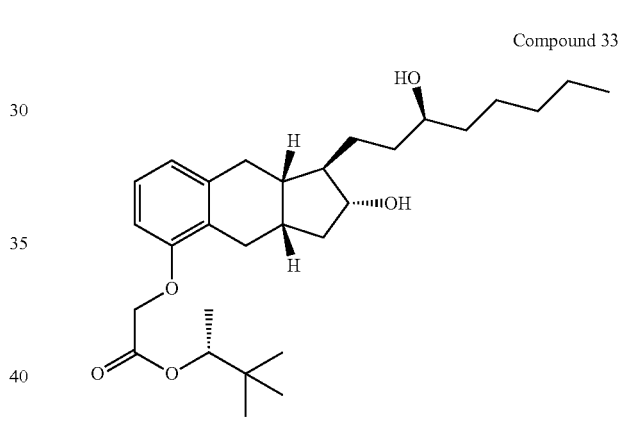

[2-Hydroxy-1-(3-hydroxy-octyl)-2,3,3a,4,9,9a-hexahydro-1H-cyclopenta[b]naphthalen-5-yloxy]-acetic acid 1,2,2-trimethyl-propyl ester (all Possible Stereoisomers, Including Compound 33)

Compound 34

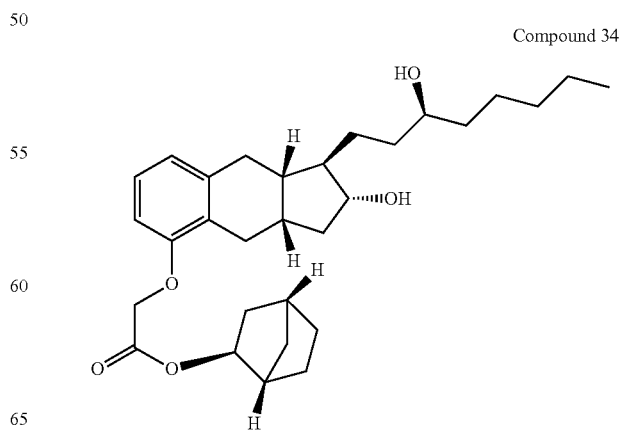

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester (all Possible Stereoisomers, Including Compound 34)

Compound 35

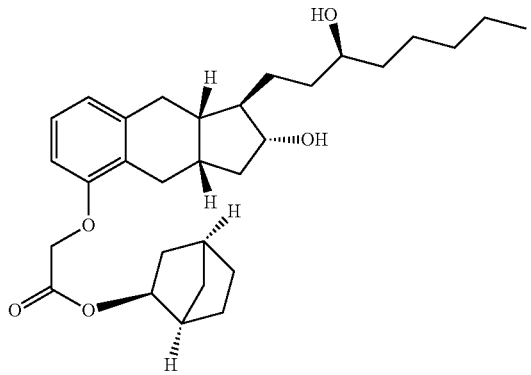

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester (all Possible Stereoisomers, Including Compound 35)

Compound 36

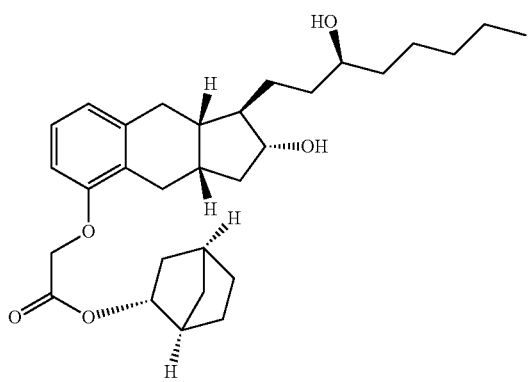

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester (all Possible Stereoisomers, Including Compound 36)

Compound 37

[2-Hydroxy-1-(3-hydroxy-octyl)-2,3,3a,4,9,9a-hexahydro-1H-cyclopenta[b]naphthalen-5-yloxy]-acetic acid bicyclo[2.2.1]hept-2-yl ester (all Possible Stereoisomers, Including Compound 37)

Compound 38

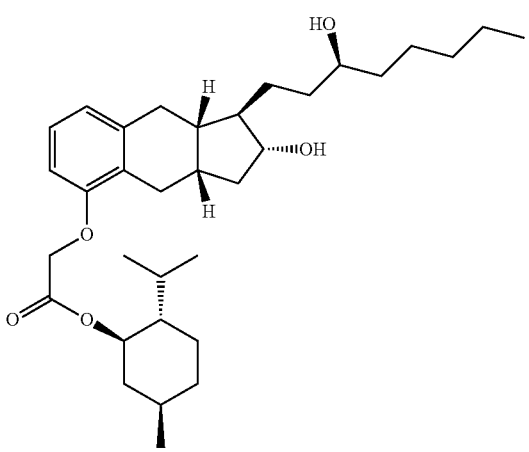

[2-Hydroxy-1-(3-hydroxy-octyl)-2,3,3a,4,9,9a-hexahydro-1H-cyclopenta[b]naphthalen-5-yloxy]-acetic acid 2-isopropyl-5-methyl-cyclohexyl ester (all Possible Stereoisomers, Including Compound 38)

Compound 39

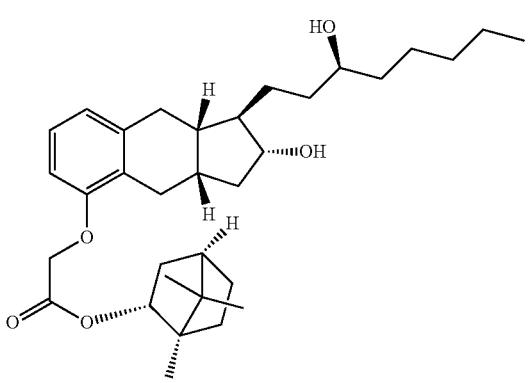

43

[2-Hydroxy-1-(3-hydroxy-octyl)-2,3,3a,4,9,9a-hexa-hydro-1H-cyclopenta[b]naphthalen-5-yloxy]-acetic acid 1,7,7-trimethyl-bicyclo[2.2.1]hept-2-yl ester (all Possible Stereoisomers, Including Compound 39)

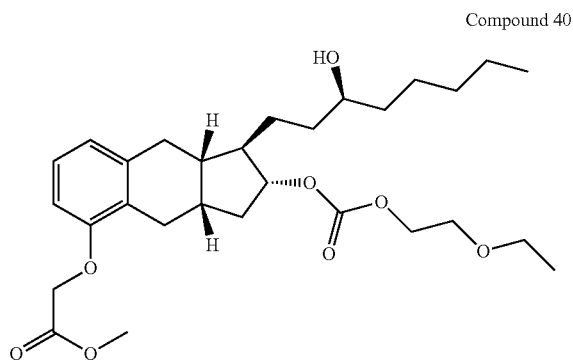 [SMILES: CCCCC[C@H](O)CC[C@@H]1[C@H]2Cc3cccc(OCC(=O)OC)c3C[C@H]2C[C@H]1OC(=O)OCCOCC]

Compound 40

[2-(2-Ethoxy-ethoxycarbonyloxy)-1-(3-hydroxy-octyl)-2,3,3a,4,9,9a-hexahydro-1H-cyclopenta[b]naphthalen-5-yloxy]-acetic acid methyl ester (all Possible Stereoisomers, Including Compound 40)

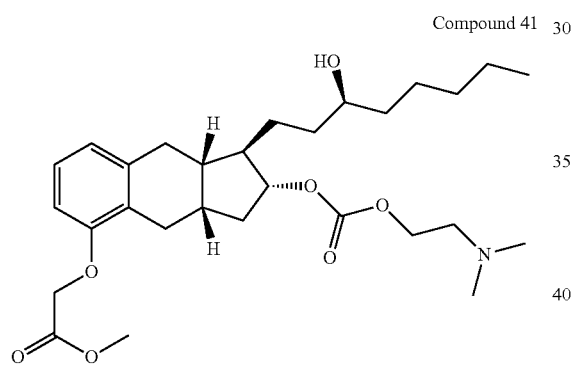

Compound 41

[2-(2-Dimethylamino-ethoxycarbonyloxy)-1-(3-hydroxy-octyl)-2,3,3a,4,9,9a-hexahydro-1H-cyclopenta[b]naphthalen-5-yloxy]-acetic acid methyl ester (all Possible Stereoisomers, Including Compound 41)

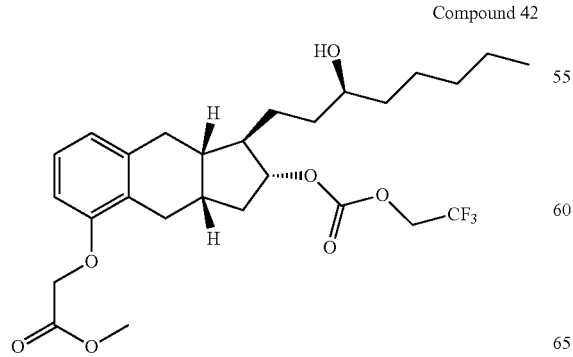

Compound 42

44

[1-(3-Hydroxy-octyl)-2-(2,2,2-trifluoro-ethoxycarbonyloxy)-2,3,3a,4,9,9a-hexahydro-1H-cyclopenta[b]naphthalen-5-yloxy]-acetic acid methyl ester (all Possible Stereoisomers, Including Compound 42)

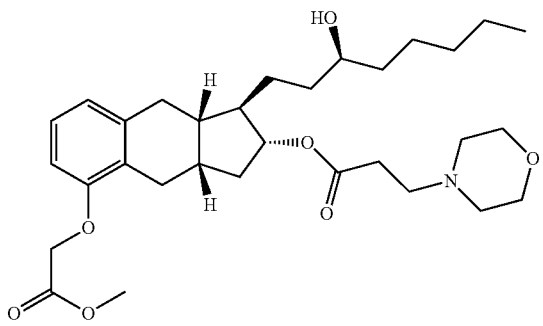

Compound 43

3-Morpholin-4-yl-propionic acid 1-(3-hydroxy-octyl)-5-methoxycarbonylmethoxy-2,3,3a,4,9,9a-hexahydro-1H-cyclopenta[b]naphthalen-2-yl ester (all Possible Stereoisomers, Including Compound 43)

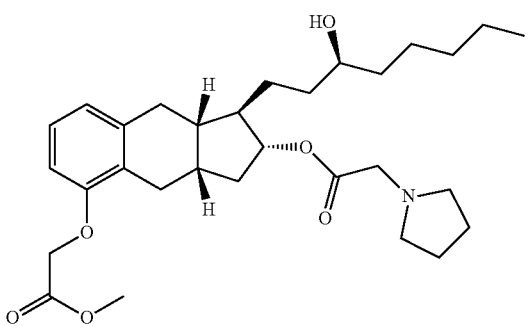

Compound 44

[1-(3-Hydroxy-octyl)-2-(2-pyrrolidin-1-yl-acetoxy)-2,3,3a,4,9,9a-hexahydro-1H-cyclopenta[b]naphthalen-5-yloxy]-acetic acid methyl ester (all Possible Stereoisomers, Including Compound 44)

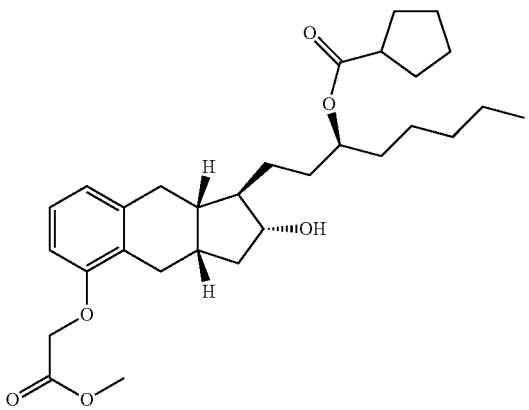

Compound 45

45

Cyclopentanecarboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester (all Possible Stereoisomers, including Compound 45)

46

4-Methyl-morpholine-2-carboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester (all Possible stereoisomers, including Compound 47)

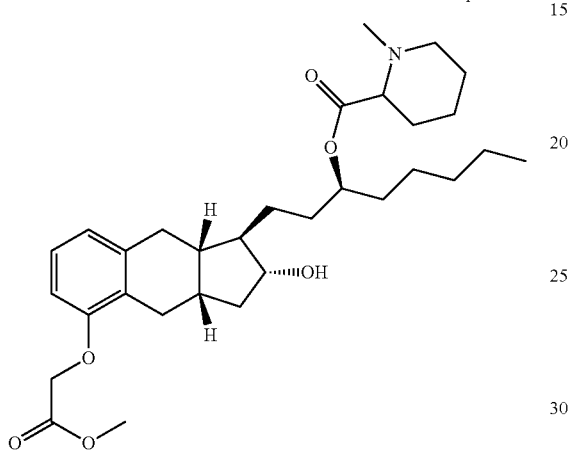

Compound 46

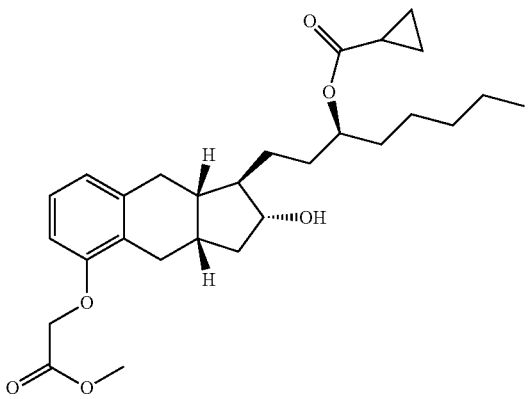

Compound 48

1-Methyl-piperidine-2-carboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester (all Possible stereoisomers, including Compound 46)

Cyclopropanecarboxylic acid 1-[2-(2-hydroxy-5-methoxycarbonylmethoxy-2,3,3a,4,9,9a-hexahydro-1H-cyclopenta[b]naphthalen-1-yl)-ethyl]-hexyl ester (all Possible Stereoisomers, including Compound 48)

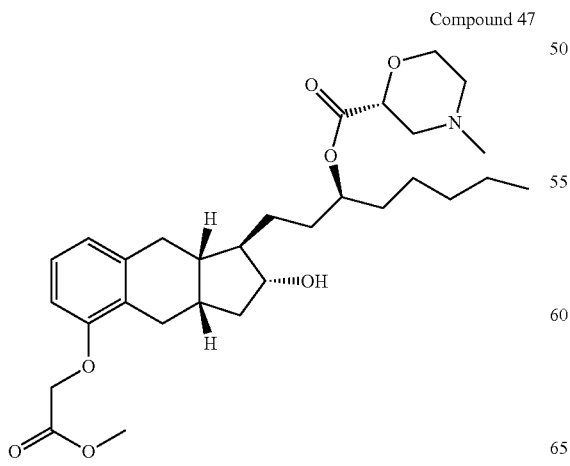

Compound 47

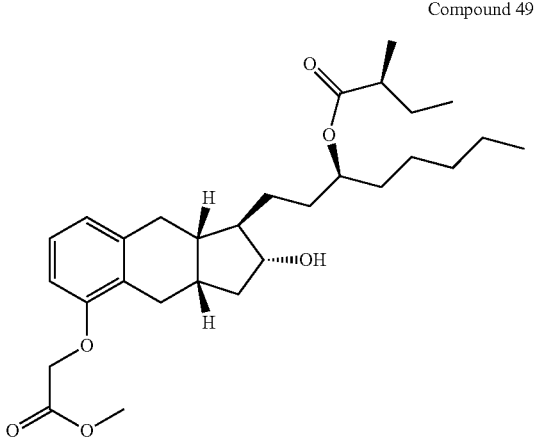 [SMILES: CCCCC[C@@H](CC[C@@H]1[C@H]2Cc3cccc(OCC(=O)OC)c3C[C@H]2C[C@H]1O)OC(=O)[C@@H](C)CC]

Compound 49

47

2-Methyl-butyric acid 1-[2-(2-hydroxy-5-methoxy-carbonylmethoxy-2,3,3a,4,9,9a-hexahydro-1H-cyclopenta[b]naphthalen-1-yl)-ethyl]-hexyl ester (all Possible Stereoisomers, Including Compound 49)

48

{1-[3-(1-Aza-bicyclo[2.2.2]oct-3-yloxycarbonyloxy)-octyl]-2-hydroxy-2,3,3a,4,9,9a-hexahydro-1H-cyclopenta[b]naphthalen-5-yloxy}-acetic acid methyl ester (all Possible Stereoisomers, including Compound 51)

Compound 50

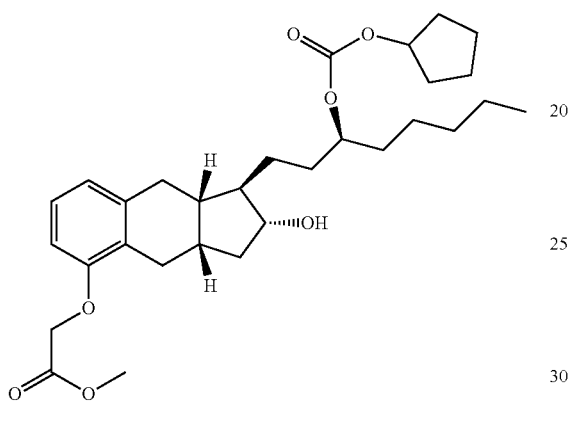

Compound 52

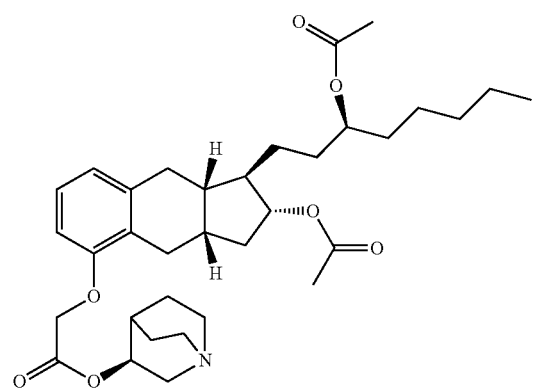

[1-(3-Cyclopentyloxycarbonyloxy-octyl)-2-hydroxy-2,3,3a,4,9,9a-hexahydro-1H-cyclopenta[b]naphthalen-5-yloxy]-acetic acid methyl ester (all Possible Stereoisomers, Including Compound 50)

[2-Acetoxy-1-(3-acetoxy-octyl)-2,3,3a,4,9,9a-hexahydro-1H-cyclopenta[b]naphthalen-5-yloxy]-acetic acid 1-aza-bicyclo[2.2.2]oct-3-yl ester (all Possible Stereoisomers, Including Compound 52)

Compound 51

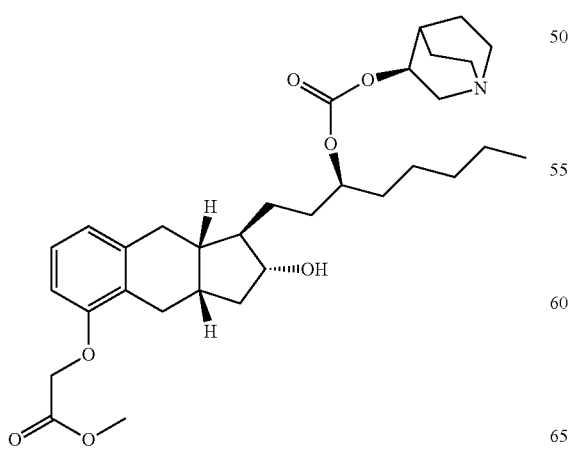

Compound 53

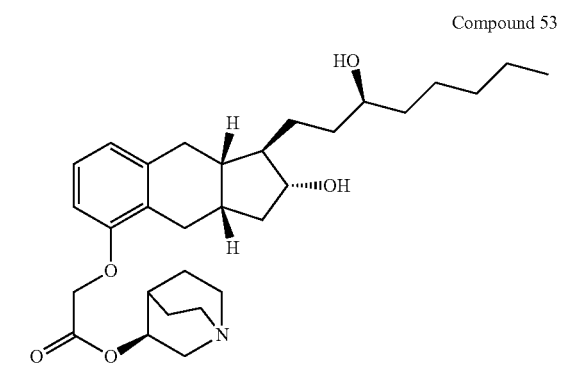 [SMILES: CCCCC[C@H](O)CC[C@@H]1[C@H]2Cc3cccc(OCC(=O)O[C@@H]4CN5CCC4CC5)c3C[C@H]2C[C@H]1O]

49

[2-Hydroxy-1-(3-hydroxy-octyl)-2,3,3a,4,9,9a-hexa-hydro-1H-cyclopenta[b]naphthalen-5-yloxy]-acetic acid 1-aza-bicyclo[2.2.2]oct-3-yl ester (all Possible Stereoisomers, Including Compound 53)

50

[2-Hydroxy-1-(3-hydroxy-octyl)-2,3,3a,4,9,9a-hexa-hydro-1H-cyclopenta[b]naphthalen-5-yloxy]-acetic acid 1,2-dimethyl-propyl ester (all Possible Stereoisomers, Including Compound 55)

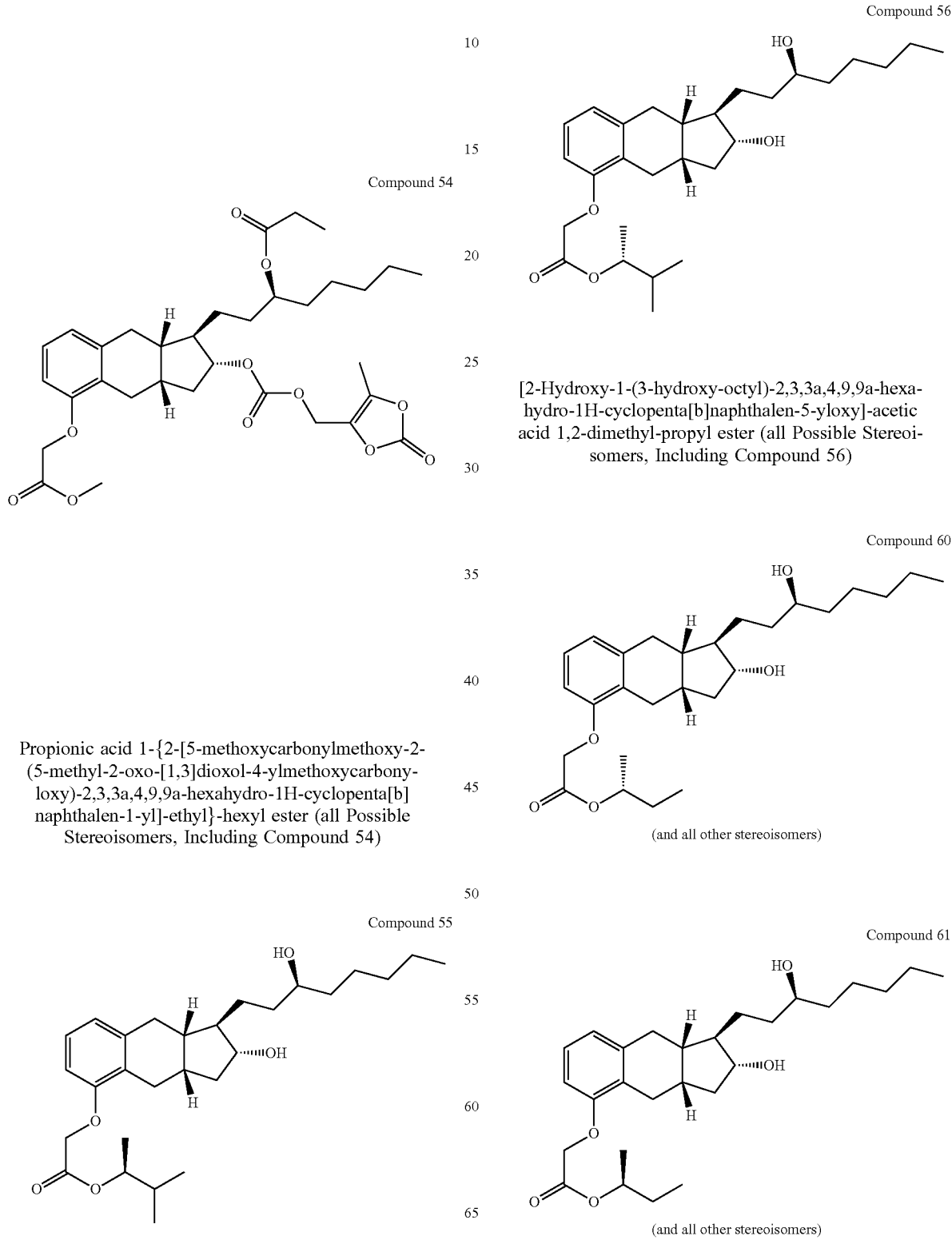

Propionic acid 1-{2-[5-methoxycarbonylmethoxy-2-(5-methyl-2-oxo-[1,3]dioxol-4-ylmethoxycarbony-loxy)-2,3,3a,4,9,9a-hexahydro-1H-cyclopenta[b]naphthalen-1-yl]-ethyl}-hexyl ester (all Possible Stereoisomers, Including Compound 54)

[2-Hydroxy-1-(3-hydroxy-octyl)-2,3,3a,4,9,9a-hexa-hydro-1H-cyclopenta[b]naphthalen-5-yloxy]-acetic acid 1,2-dimethyl-propyl ester (all Possible Stereoisomers, Including Compound 56)

51
-continued

Compound 62

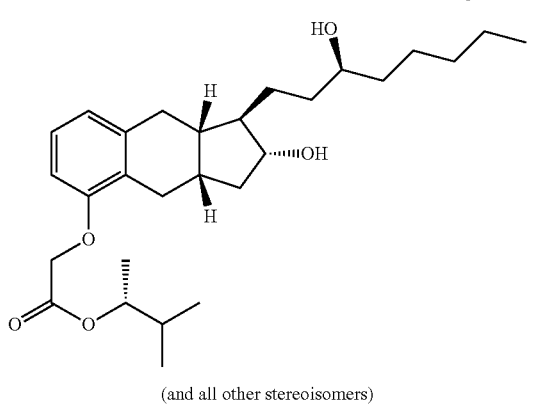

(and all other stereoisomers)

Compound 63

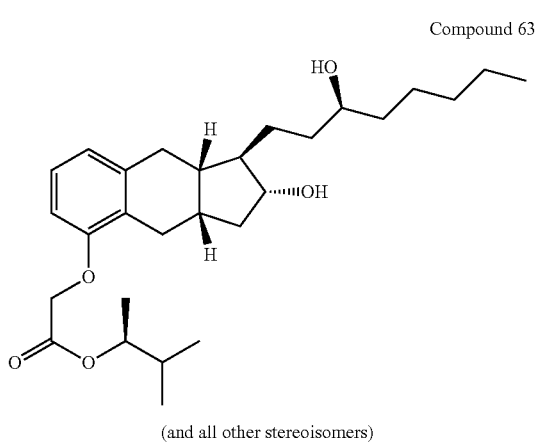

(and all other stereoisomers)

Compound 64

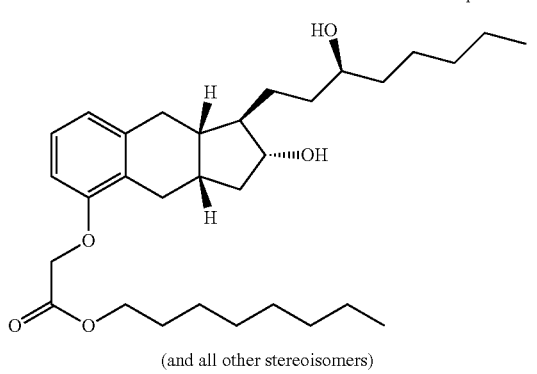

(and all other stereoisomers)

52

Core Structure Formulae II and IIA

In another embodiment, the invention provides a compound represented by Formula II:

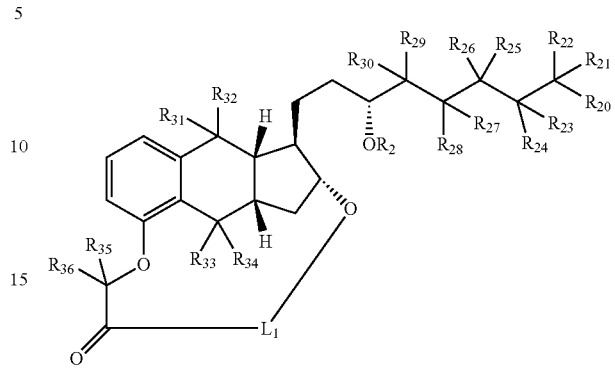

wherein, $R_2$ is selected from the group consisting of H and $P_2$;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;

$L_1$ is selected from the group consisting of —O-alkylene-C(O)—, —O-alkylene-OC(O)—, or a bond; wherein $P_2$ is selected from the group consisting of:

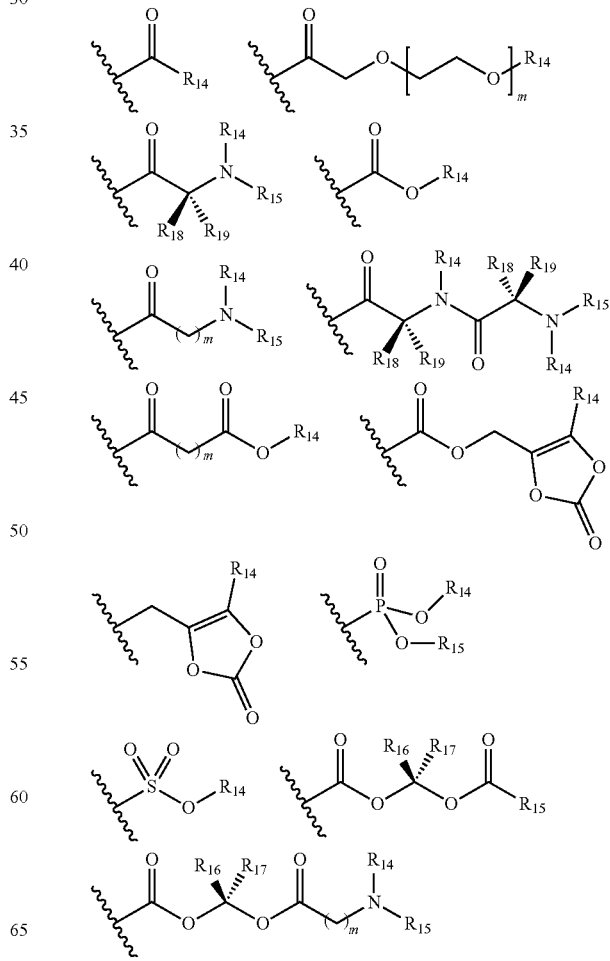

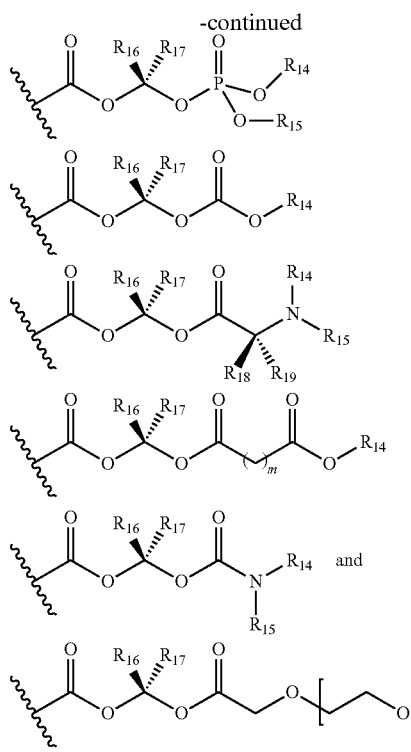

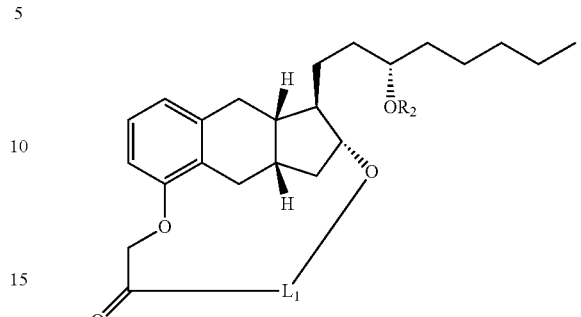

wherein $L_1$ and $R_2$ are defined as in Formula II.

Examples of Compounds of Formula II

The following represent specific compounds of Formula II:

wherein, m is 1, 2, 3, or 4;

$R_{14}$ and $R_{15}$ are as defined above;

$R_{14}$ and $R_{15}$ taken together with the atoms to which they attach optionally form a 5- to 7-membered ring optionally incorporating one or two ring heteroatoms chosen from N, O and S, which is unsubstituted or substituted with 1, 2, or 3 substituents independently selected from the group consisting of halo, methyl and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are as defined above;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula H includes enantiomers, pharmaceutically acceptable salts, solvates and polymorphs of the compounds of Formula II.

In one embodiment, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are H. In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ is deuterium.

In one embodiment, $L_1$ is selected from the group consisting of —O-alkyl-C(O)— and —O— alkyl-OC(O)—. In one embodiment, $L_1$ is —O-alkylene-C(O)—. In one embodiment, $L_1$ is —O— alkylene-OC(O)—. In one embodiment, the alkylene group of claim 41 is a $C_1$-$C_5$ alkylene group. In one embodiment, the alkylene group of claim 41 is a $C_1$ alkylene group.

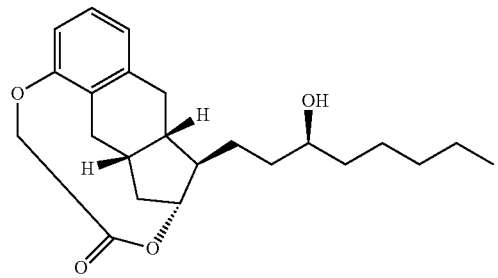

Compound 57

Treprostinil 2-hydroxy lactone (all Possible Stereoisomers, Including Compound 57)

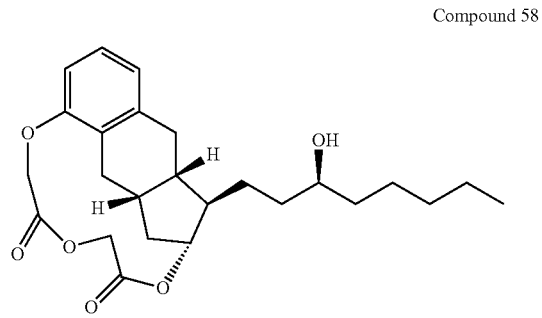 [SMILES: CCCCC[C@H](O)CC[C@@H]1[C@H]2Cc3cccc4c3C[C@H]2C[C@H]1OC(=O)COC(=O)CO4]

Compound 58

[2-Hydroxy-1-(3-hydroxy-octyl)-2,3,3a,4,9,9a-hexa-hydro-1H-cyclopenta[b]naphthalen-5-yloxy]-acetic acid carboxymethyl lactone (all Possible Stereoisomers, Including Compound 58)

Core Structure Formula III

In one embodiment, the invention provides a compound represented by Formula III:

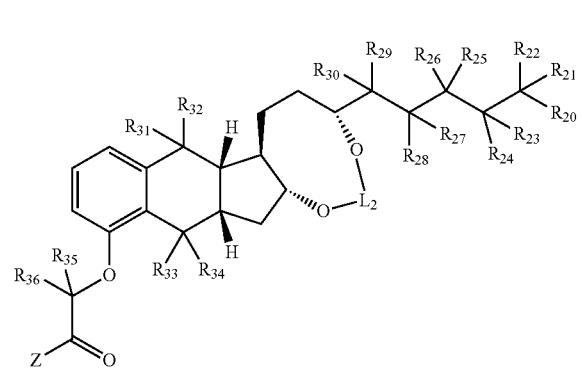

wherein $L_2$ is selected from the group consisting of —$CH_2$—, —CHMe-, —C(Me)$_2$- and the following:

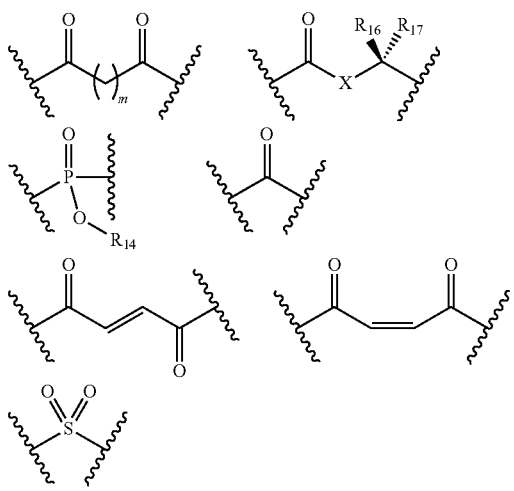

wherein,
m is 1, 2, 3, or 4;
X is $NR_{14}$ or O;
$R_{14}$ is selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;
$R_{16}$ and $R_{17}$ are independently in each occurrence H or alkyl;
$R_{16}$ and $R_{17}$ taken together with the atoms to which they attach optionally form a 3- to 6-membered ring; and
$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;
wherein Z is —OH, —$OR_{11}$, —$N(R_{11})R_{12}$, —$SR_{11}$, or $P_1$;
$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkyl heteroaryl;
$R_{12}$ is H, haloalkyl, heteroalkyl, cycloheteroalkyl, alkylcycloalkyl, alkylcycloheteroalkyl, aryl, or heteroaryl;
$P_1$ is selected from the group consisting of:

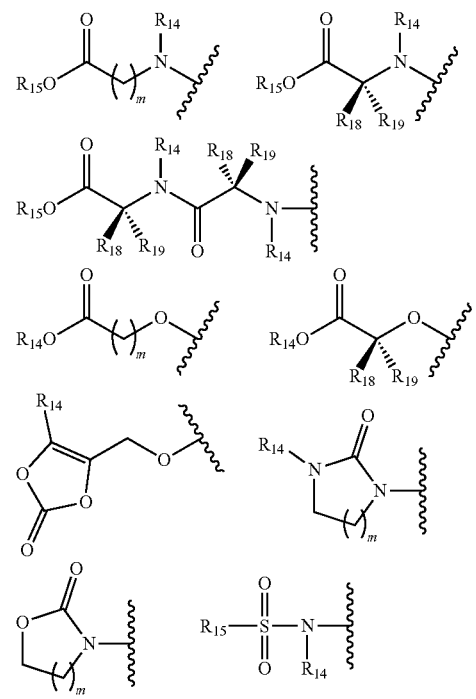

wherein,
m is 1, 2, 3, or 4;
$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;
$R_{14}$ and $R_{15}$ taken together with the atoms to which they attach optionally form a 5- to 7-membered ring optionally incorporating one or two ring heteroatoms chosen from N, O and S, which is unsubstituted or substituted with 1, 2, or 3 substituents independently selected from the group consisting of halo, methyl, and methoxy;
$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —$CONH_2$, aryl, and heteroaryl, wherein the aryl or heteroaryl is unsubstituted or substituted from the list consisting of alkyl, halo, haloalkyl, hydroxy, alkoxy, and haloalkoxy;
$R_{14}$ and $R_{18}$ taken together with the atoms to which they attach optionally form a 5- to 7-membered ring;
$R_{14}$ and $R_{19}$ taken together with the atoms to which they attach optionally form a 5- to 7-membered ring;
$R_{15}$ and $R_{18}$ taken together with the atoms to which they attach optionally form a 5- to 7-membered ring;
$R_{15}$ and $R_{19}$ taken together with the atoms to which they attach optionally form a 5- to 7-membered ring;

wherein Formula III includes enantiomers, pharmaceutically acceptable salts, solvates and polymorphs of the compounds of Formula III.

In one embodiment, $L_2$ is selected from the group consisting of:

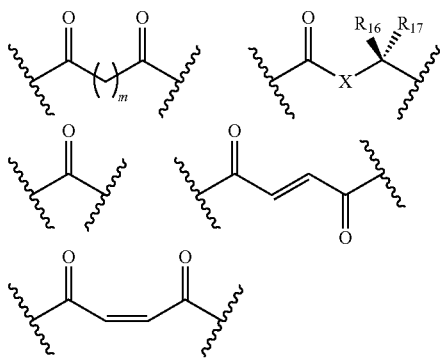

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ is deuterium, or they are all hydrogen.

One particular sub-embodiment of Formula III includes a compound represented by Formula IIIA:

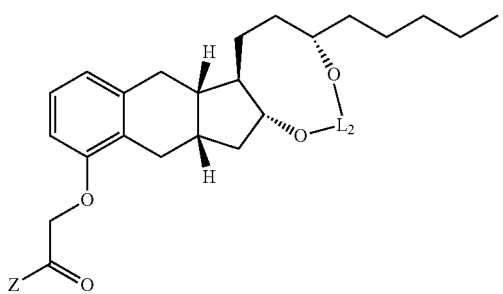

wherein Z and $L_2$ are defined as in Formula III.

Examples of Compounds of Formula III

The following compounds represent specific examples of Formula III compounds:

Compound 59

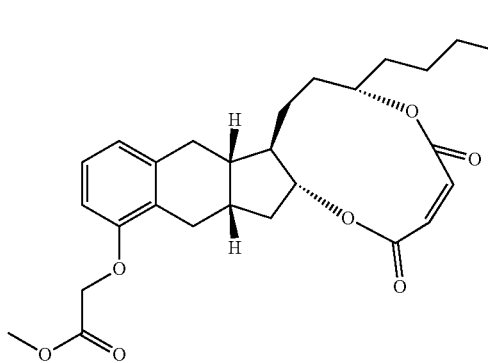

[2-Hydroxy-1-(3-hydroxy-octyl)-2,3,3a,4,9,9a-hexahydro-1H-cyclopenta[b]naphthalen-5-yloxy]-acetic acid methyl ester 2,3-maleate (all Possible Stereoisomers, Including Compound 59)

Core Structure Formula IV

Another embodiment is a compound represented by Formula IV, wherein unlike in Formula II, the $L_1$ group links to $R_2$ rather than $R_1$:

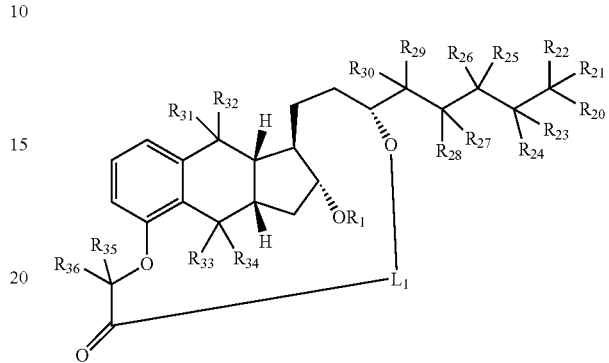

wherein $R_1$ is selected from the group consisting of H and $P_2$;
$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ are independently selected from the group consisting of H and deuterium;
$L_1$ is a selected from the group consisting of —O-alkylene-C(O)—, —O-alkylene-OC(O)—, and a bond; wherein
$P_2$ is selected from the group consisting of:

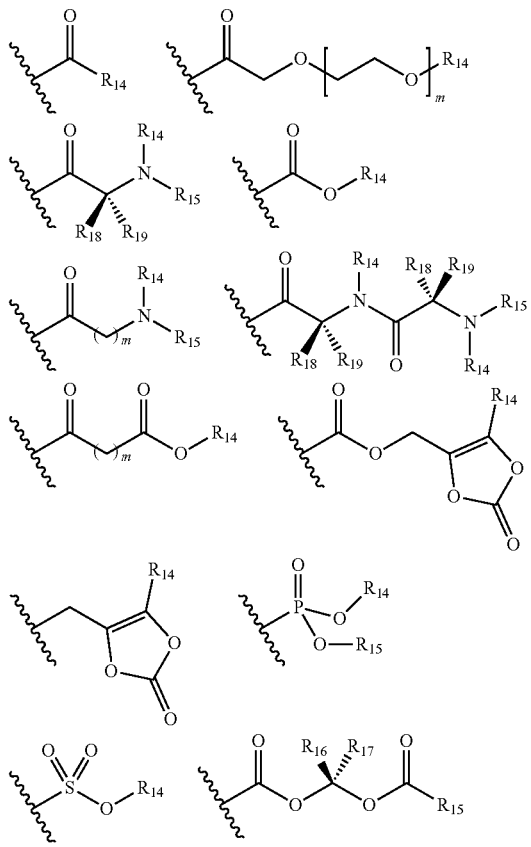

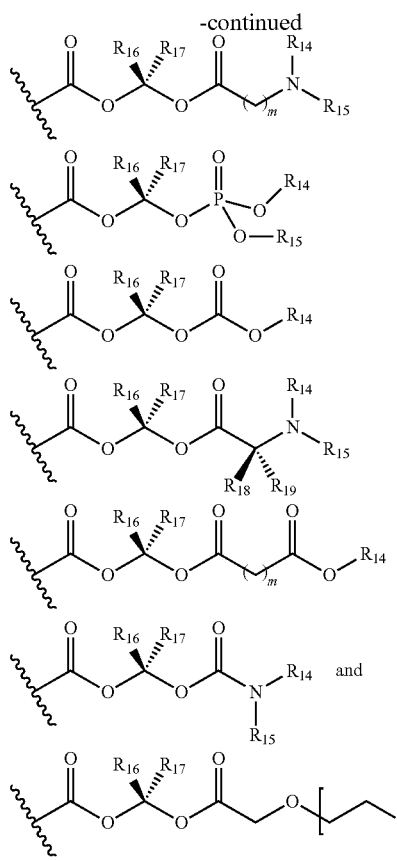

wherein, m is 1, 2, 3, or 4;

$R_{14}$ and $R_{15}$ are independently in each occurrence selected from the group consisting of H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl;

$R_{14}$ and $R_{15}$ taken together with the atoms to which they attach optionally form a 5- to 7-membered ring optionally incorporating one or two ring heteroatoms chosen from N, O and S, which is unsubstituted or substituted with 1, 2, or 3 substituents independently selected from the group consisting of halo, methyl, and methoxy;

$R_{16}$ and $R_{17}$ are independently in each occurrence H or alkyl;

$R_{16}$ and $R_{17}$ taken together with the atoms to which they attach optionally form a 3- to 6-membered ring;

$R_{18}$ and $R_{19}$ are independently in each occurrence selected from the group consisting of hydrogen and alkyl, wherein the alkyl is unsubstituted or substituted with 1 substituent selected from the list consisting of halo, hydroxy, alkoxy, amino, thio, methylthio, —C(O)OH, —C(O)O-(alkyl), —CONH$_2$, aryl, and heteroaryl, wherein the aryl or heteroaryl is unsubstituted or substituted from the list consisting of alkyl, halo, haloalkyl, hydroxy, alkoxy, and haloalkoxy;

$R_{14}$ and $R_{18}$ taken together with the atoms to which they attach optionally form a 5- to 7-membered ring;

$R_{14}$ and $R_{19}$ taken together with the atoms to which they attach optionally form a 5- to 7-membered ring;

wherein Formula IV includes enantiomers, pharmaceutically acceptable salts, solvates and polymorphs of the compounds of Formula IV.

In one embodiment, at least one of $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, and $R_{36}$ is deuterium, or they are all hydrogen.

In a particular embodiment of Formula IV, a compound is represented by Formula IVA:

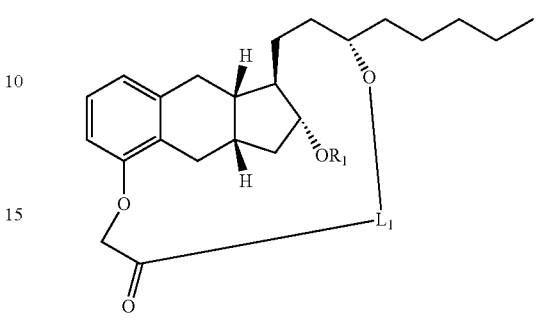

wherein $L_1$ and $R_1$ are defined as in Formula IV.

Similar approaches can be used to make and use Formula IV compounds as for Formula II compounds.

Embodiments from Priority Provisional 61/751,608

One embodiment from the priority provisional is a compound according to Formula (IAA).

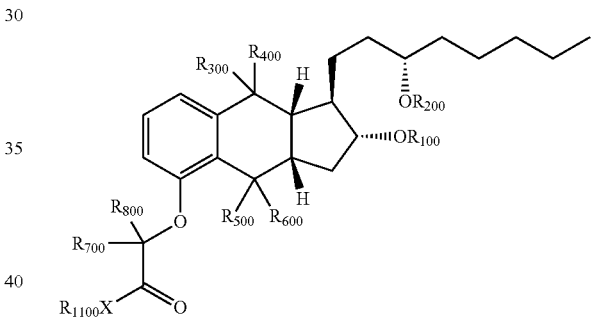

wherein, $R_{100}$ and $R_{200}$ are independently selected from the group consisting of H, —CONR$_{900}$R$_{1000}$, —CR$_{900}$R$_{1000}$OCOP$_3$R$_{900}$(R$_{1000}$), wherein $R_{900}$ and $R_{1000}$ are independently selected from H, alkyl, and cycloalkyl;

$R_{300}$, $R_{400}$, $R_{500}$, $R_{600}$, $R_{700}$ and $R_{800}$ are independently selected from the group consisting of H and deuterium;

X is O, —NHR$_{1200}$, or S;

$P_3$ is N or O;

$R_{1100}$ is haloalkyl, heteroalkyl, cycloheteroalkyl, alkylcycloalkyl, alkylcycloheteroalkyl, aryl, or heteroaryl;

$R_{1200}$ is haloalkyl, heteroalkyl, cycloheteroalkyl, alkylcycloalkyl, alkylcycloheteroalkyl, aryl, heteroaryl.

In one embodiment, $R_{100}$ and $R_{200}$ are H. In one embodiment, $R_{300}$, $R_{400}$, $R_{500}$, $R_{600}$, $R_{700}$ and $R_{800}$ are H. In one embodiment, X is O. In one embodiment, $R_{1100}$ is selected from the group consisting of:

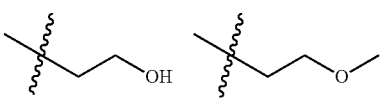

-continued

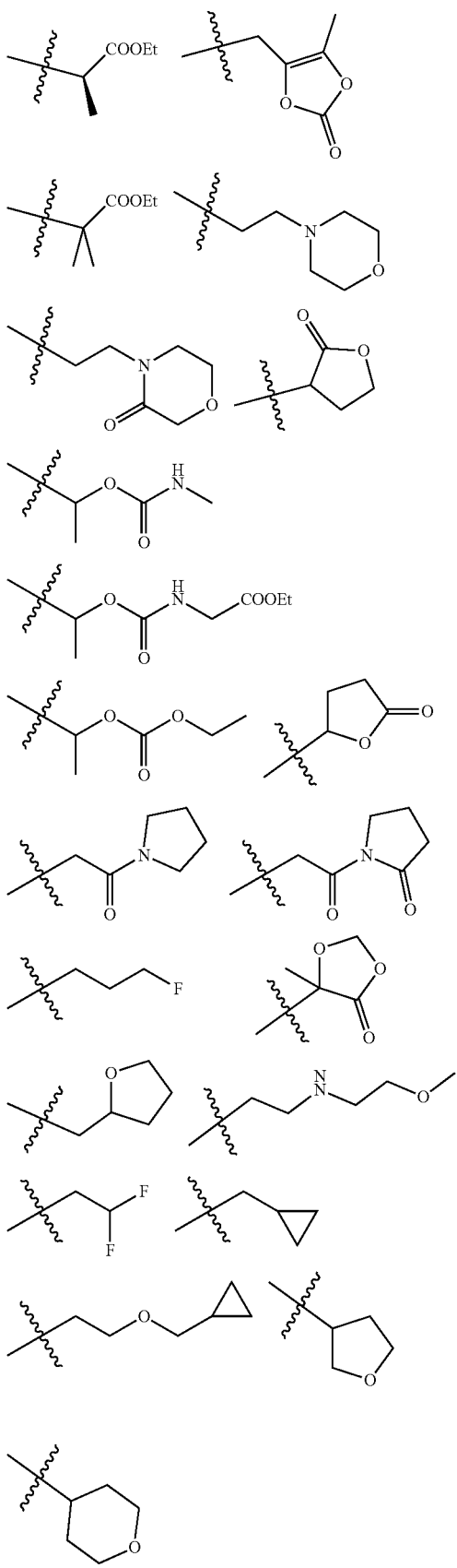

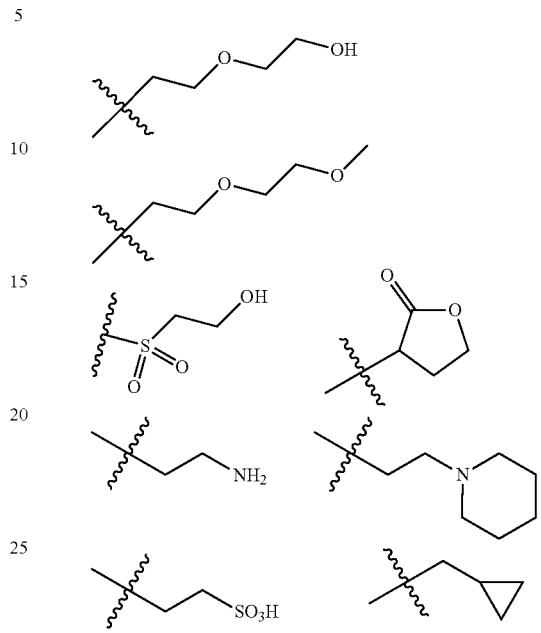

In one embodiment, X is —NHR$_{1200}$.

In one embodiment, R$_{1100}$ is chosen from the group consisting of:

In one embodiment, X is O. In one embodiment, R$_{300}$, R$_{400}$, R$_{500}$, R$_{600}$, R$_{700}$ and R$_{800}$ are H. In one embodiment, R$_{1100}$ is alkyl.

Another embodiment from the priority provisional is a compound of Formula II(AA):

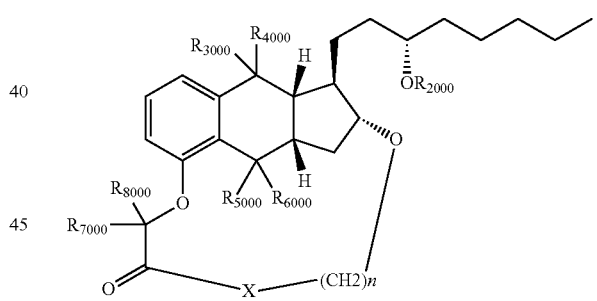

wherein,

R$_{2000}$ is independently selected from the group consisting of H, —CONR$_{9000}$R$_{10000}$, —CR$_{9000}$R$_{10000}$OCOP$_4$R$_{9000}$ (R$_{10000}$), wherein R$_{9000}$ and R$_{10000}$ are independently selected from H, alkyl, and cycloalkyl;

R$_{3000}$, R$_{4000}$, R$_{5000}$, R$_{6000}$, R$_{7000}$ and R$_{8000}$ are independently selected from the group consisting of H and deuterium;

X is O, —NR$_{12000}$ or S;

P$_4$ is N or O;

R$_{12000}$ is haloalkyl, heteroalkyl, cycloheteroalkyl, alkylcycloalkyl, alkylcycloheteroalkyl, aryl, or heteroaryl;

n is an integer between 1 and 7;

wherein compounds of Formula II(AA) include enantiomers, pharmaceutically acceptable salts, solvates and polymorphs of the compounds of Formula II(AA).

Another embodiment from the priority provisional is a compound having Formula III(AA):

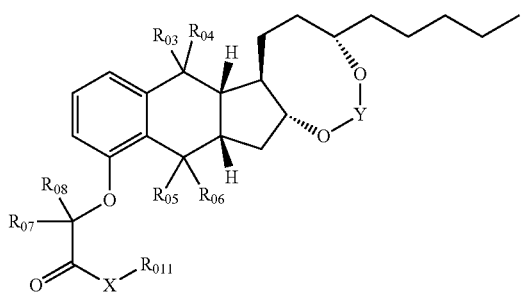

wherein, $R_{11}$ is haloalkyl, heteroalkyl, cycloheteroalkyl, alkylcycloalkyl, alkylcycloheteroalkyl, aryl, or heteroaryl;

$R_{03}$, $R_{04}$, $R_{05}$, $R_{06}$, $R_{07}$ and $R_{08}$ are independently selected from the group consisting of H and deuterium;

X is O, —$NR_{012}$ or S;

$R_{012}$ is haloalkyl, heteroalkyl, cycloheteroalkyl, alkylcycloalkyl, alkylcycloheteroalkyl, aryl, or heteroaryl;

Y is C=O, —$CH_2$—, —CHMe-, or —$C(Me)_2$-;

and compounds of Formula III(AA) include enantiomers, pharmaceutically acceptable salts, solvates and polymorphs of the compounds of Formula III(AA).

Methods of Making Compounds of Formula I

The compounds of formula I where $R_1$ and $R_2$ are H can be synthesized according to Scheme 1 by starting with the compound of Formula I where Z is OH and $R_1$ is H and $R_2$ is PG which represents a protective group as described in *Protective Groups in Organic Synthesis* by Greene and Wuts. The carboxylic acid is activated using coupling conditions which involve the use of an activating agent, including but not limited to EDC, DCC, DIC, BOP, HATU, HBTU, CDI, thionyl chloride, or oxalyl chloride. Coupling conditions may also include or not include an additive, including but not limited to DMF, HOSu, HOBT, or HOAT, and may or may not include one or more nucleophilic or non-nucleophilic bases or additives including, but not limited to, DMAP, TEA, DIPEA, N-methylmorpholine, pyridine, and/or imidazole. Coupling conditions also may be run in a suitable solvent or solvent mixture including, but not limited to, DCM, THF, DMF, dioxane, ethyl acetate, and/or acetonitrile. The activated acid can be isolated and purified or can be treated directly with the reagent ZH. Alternately, ZH can be present during the coupling conditions. Representative examples of coupling conditions and definitions of the activating agents, additives and bases can be found in in *Handbook of Reagents for Organic Synthesis: Activating Agents and Protecting Groups*, John Wiley and Sons. The resulting compound of Formula I where Z is not OH, $R_1$ is H and $R_2$ is PG is deprotected using deprotection conditions suitable to the type of protective group represented by PG to give the compound of Formula I. Examples of suitable deprotection conditions can be found in Protective Groups in Organic Synthesis by Greene and Wuts.

Scheme 1

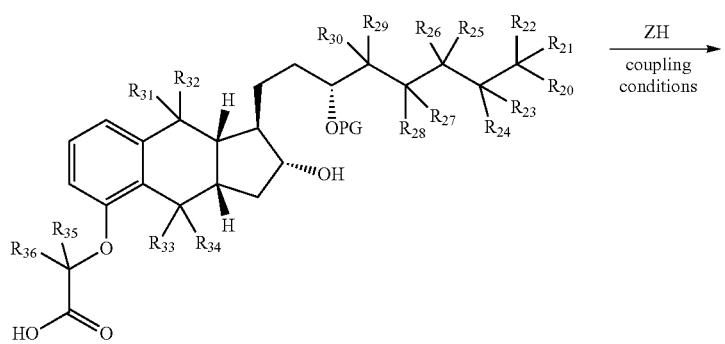

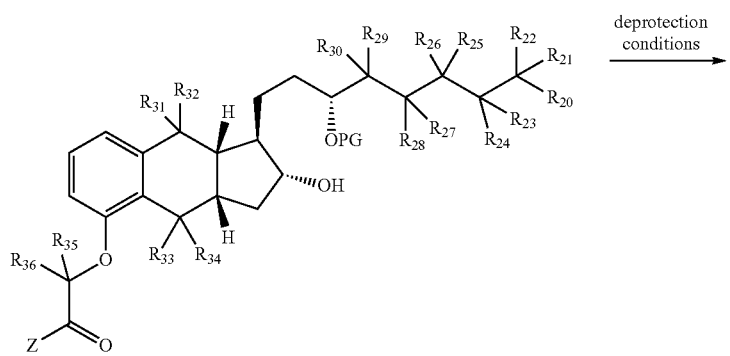

-continued

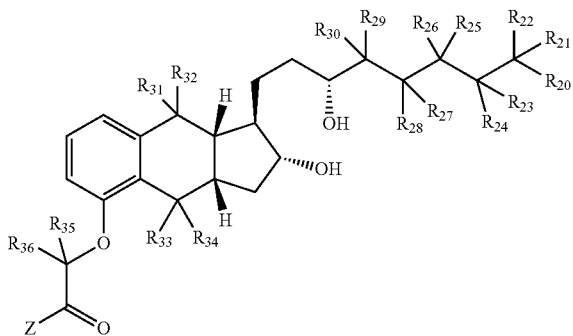

The compound of Formula I where $R_1=R_2$ or where $R_1$ is H can be synthesized according to Scheme 2 starting from the compound of Formula I where $R_1$ and $R_2$ are H by employing acylation conditions and the reactive molecule ROH or RY, where Y is a leaving group including, but not limited to, halogen, sulfonyl, phosphoryl, or acyl. In the case where the reactive molecule ROH is used, acylation conditions are similar to coupling conditions as described above.

In the case where the reactive molecule RY is used, the acylation conditions may or may not include one or more nucleophilic or non-nucleophilic bases or additives including but not limited to DMAP, TEA, DIPEA, N-methylmorpholine, pyridine, and/or imidazole and may be run in a suitable solvent or solvent mixture including, but not limited to DCM, THF, DMF, dioxane, ethyl acetate, and/or acetonitrile.

Scheme 2

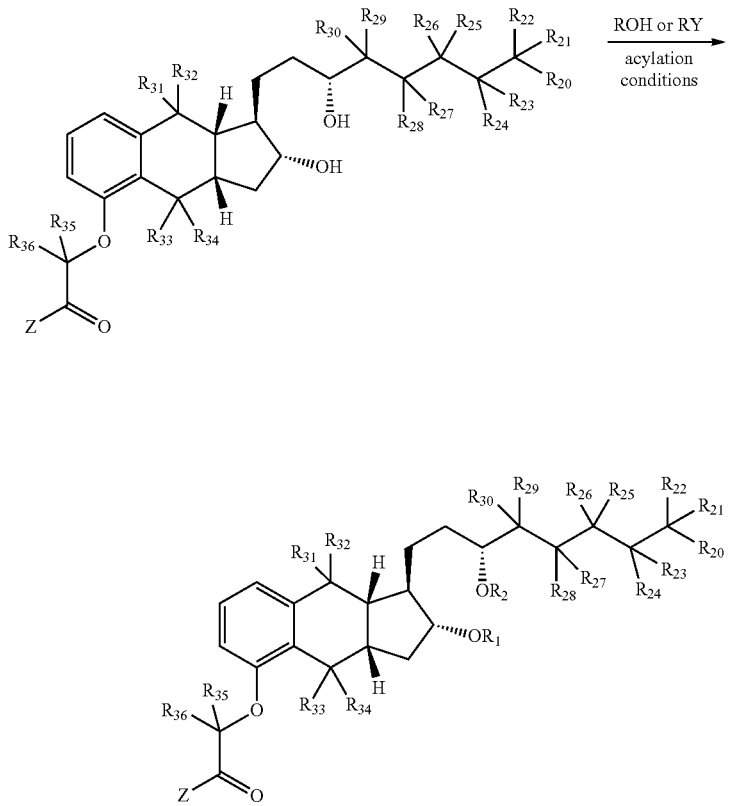

The compounds of Formula I where $R_2$ is H can be synthesized according to Scheme 3 starting from the compound of Formula I where $R_1$ is H and $R_2$ is PG as described above, by employing acylation conditions using ROH or RY as described above followed by deprotection conditions as described above.

tion conditions can be found in *Chemical Reviews* (2007), 107, 239 and *Beilstein Journal of Organic Chemistry* (2012), 8, 1344, and include but are not limited to 2,4,6-trichlorobenzoic anhydride, TEA and DMAP; 4-nitrobenzoic anhydride, TEA, and DMAP; 2-chloro-1-methylpyridinium iodide and tributyl amine; 2,2'-dipyridyl disulfide and triph- Scheme 3

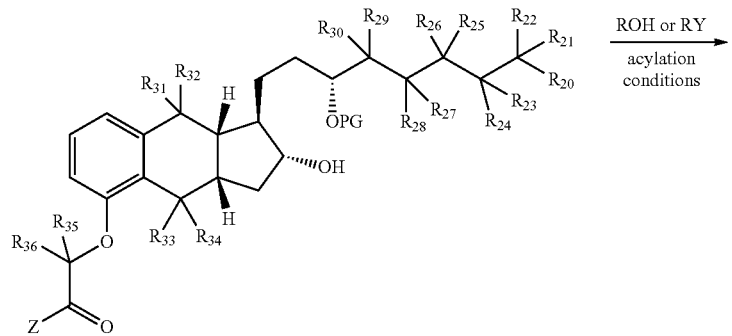

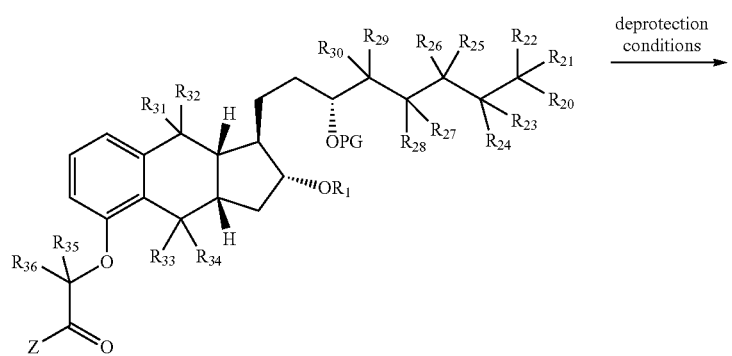

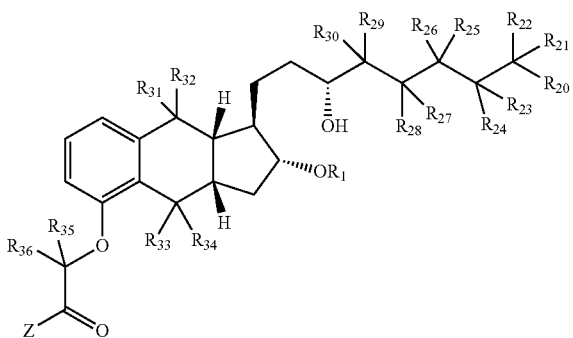

Methods of Making Compounds of Formula II

The compounds of Formula II can be synthesized according to Scheme 4 starting from the compound of Formula I where Z is OH and $R_2$ is PG as described above, by employing lactonization conditions. Examples of lactonization conditions enylphosphine; and all the reactions in the coupling conditions and acylation conditions described above. The lactonization reactions may be run in a suitable solvent or solvent mixture including, but not limited to DCM, THF, DMF, dioxane, ethyl acetate, acetonitrile and/or toluene.

Scheme 4

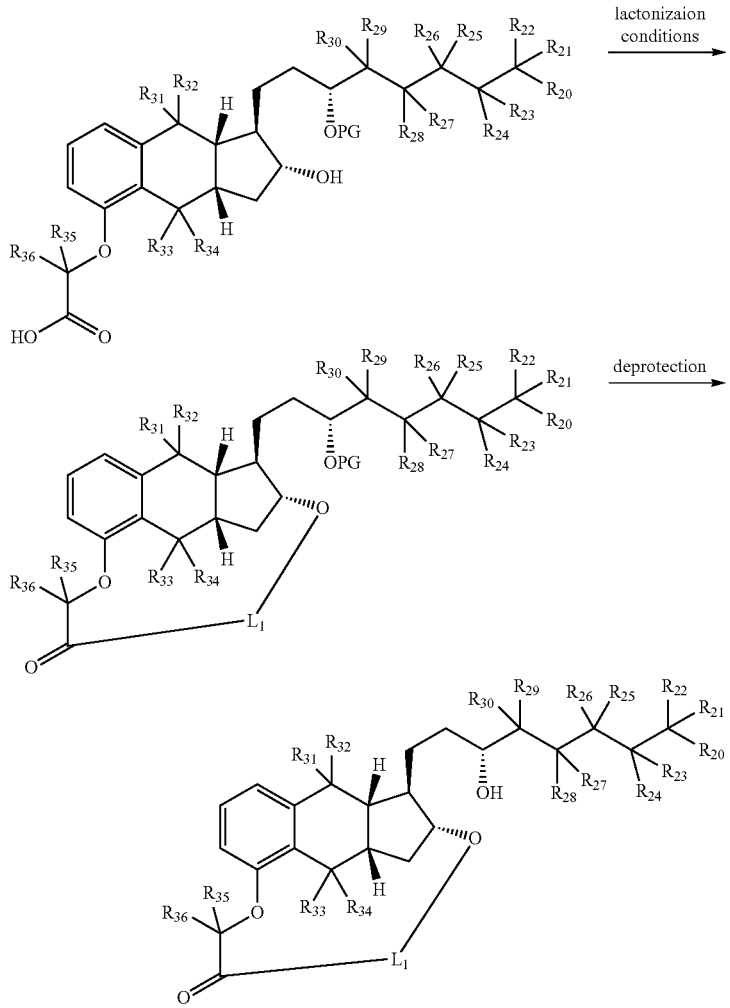

Methods of Making Compounds of Formula III

The compounds of Formula III can be synthesized according to Scheme 5 starting with the compound of Formula I where $R_1$ and $R_2$ are H, by reacting with an activated carbonyl equivalent including but not limited to phosgene, carbonyl diimidazole, or 4-nitrophenyl chloroformate, in the presence or absence of one or more nucleophilic or non-nucleophilic bases or additives including but not limited to DMAP, TEA, DIPEA, N-methylmorpholine, pyridine, and/or imidazole and may be run in a suitable solvent or solvent mixture including but not limited to DCM, THF, DMF, dioxane, ethyl acetate, acetonitrile, and/or toluene.

Scheme 5

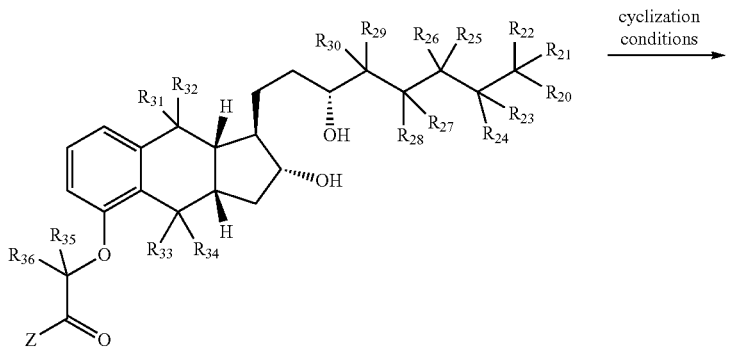

-continued

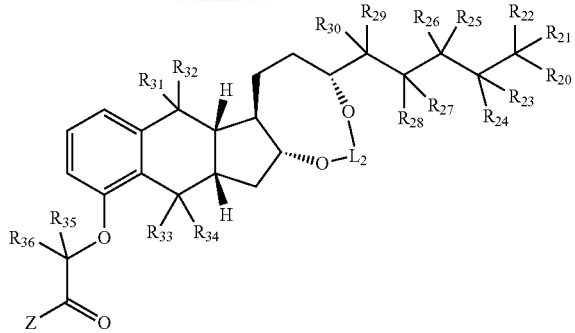

Pharmaceutical Compositions

The compounds described herein can be used alone or in combination with other components as known in the art. In particular, formulations of multiple ingredients can be prepared that are adapted for use in prophylactic and therapeutic treatments. The composition can be in the form of, for example, a solid, liquid, semi-solid, solution, suspension, or emulsion formulation. Water can be used as a formulation agent. It can be in pure form or combined with one or more excipients.

In one embodiment, the compound is formulated in matrix form, comprising a matrix material in which drug is contained or dispersed. The matrix material further controls release of the drug by controlling dissolution and/or diffusion of the drug from the reservoir, and may enhance stability of the drug molecule while stored in the reservoir. In one embodiment, the drug is formulated with an excipient material that is useful for accelerating release, e.g., a water-swellable material that can aid in pushing the drug out of the reservoir and through any tissue capsule over the reservoir. Examples include hydrogels and osmotic pressure generating agents known in the art. In another embodiment, the drug is formulated with a penetration enhancer(s). The penetration enhancer further controls release of the drug by facilitating transport of the drug across the skin into the local administration site or systemic delivery.

More particularly, the drug can be dispersed in a matrix material, to further control the rate of release of drug. This matrix material can be a "release system," as described in U.S. Pat. No. 5,797,898, the degradation, dissolution, or diffusion properties of which can provide a method for controlling the release rate of the chemical molecules.

The release system may provide a temporally modulated release profile (e.g., pulsatile release) when time variation in plasma levels is desired or a more continuous or consistent release profile when a constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e., pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release). The active release systems described herein can be used alone or on combination with passive release systems, for example, as described in U.S. Pat. No. 5,797,898.

The pharmaceutical agent can be formulated with one or more pharmaceutically acceptable excipients. Representative examples include bulking agents, wetting agents, stabilizers, crystal growth inhibitors, antioxidants, antimicrobials, preservatives, buffering agents (e.g., acids, bases), surfactants, desiccants, dispersants, osmotic agents, binders (e.g., starch, gelatin), disintegrants (e.g., celluloses), glidants (e.g., talc), diluents (e.g., lactose, dicalcium phosphate), color agents, lubricants (e.g., magnesium stearate, hydrogenated vegetable oils) and combinations thereof. In some embodiments, the excipient is a wax or a polymer. In one embodiment, the polymer comprises polyethylene glycol (PEG), e.g., typically one having a molecular weight between about 100 and 10,000 Daltons (e.g., PEG 200, PEG 1450). In another embodiment, the polymer comprises poly lactic acid (PLA), poly glycolic acid (PGA), copolymers thereof (PLGA), or ethyl-vinyl acetate (EVA) polymers. In yet another embodiment, the excipient material comprises a pharmaceutically acceptable oil (e.g., sesame oil).

In one embodiment, the excipient material includes a saturated drug solution. That is, the excipient material comprises a liquid solution formed of the drug dissolved in a solvent for the drug. The solution is saturated so that the solvent does not dissolve the solid matrix form of the drug. The saturated solution acts as a non-solvent excipient material, substantially filling pores and voids in the solid matrix.

In another embodiment, the excipient material comprises a pharmaceutically acceptable perhalohydrocarbon or unsubstituted saturated hydrocarbon. See, for example, U.S. Pat. No. 6,264,990 to Knepp et al, which describes anhydrous, aprotic, hydrophobic, non-polar liquids, such as biocompatible perhalohydrocarbons or unsubstituted saturated hydrocarbons, such as perfluorodecalin, perflurobutylamine, perfluorotripropylamine, perfluoro-N-methyldecahydroquindine, perfluoro-octohydro quinolidine, perfluoro-N-cyclohexylpyrilidine, perfluoro-N,N-dimethylcyclohexyl methylamine, perfluoro-dimethyl-adamantane, perfluorotrimethylbicyclo (3.3.1) nonane, bis(perfluorohexyl) ethene, bis(perfluorobutyl) ethene, perfluoro-1-butyl-2-hexyl ethene, tetradecane, methoxyflurane and mineral oil.

In one embodiment, the pharmaceutically acceptable excipient material comprises dimethyl sulfoxide (DMSO), glycerol, or ethanol.

Mixtures of compounds according to Formulae I, H, III, and IV can be used.

As noted above, a pharmaceutical composition can comprise a treprostinil derivative or a pharmaceutically acceptable salt, solvate, clathrate or polymorph thereof, and one or more pharmaceutically acceptable carriers or excipients. The composition can optionally contain an additional therapeutic agent.

Pharmaceutically acceptable carriers and excipients include pharmaceutically acceptable materials, vehicles and substances. Non-limiting examples of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, sweetening agents, flavoring agents, coloring agents, stabilizers, preservatives, antioxidants, antimicrobial agents, antibacterial agents, antifungal agents, adjuvants, encapsulating materials and coating materials. The use of such excipients in pharmaceutical formulations is known in the art. Except insofar as any conventional carrier or excipient is incompatible with the active ingredient, the disclosure encompasses the use of conventional carriers and excipients in formulations containing treprostinil derivatives. See, e.g., Remington: The Science and Practice of Pharmacy, 21st Ed., Lippincott Williams & Wilkins (Philadelphia, Pa. [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla. [2004]).

Proper formulation can depend on various factors, such as the route of administration chosen. Potential routes of administration of pharmaceutical compositions comprising treprostinil derivatives include without limitation oral, parenteral (including intramuscular, subcutaneous, intradermal, intravascular, intravenous, intraarterial, intramedullary and intrathecal), intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal).

As an example, formulations of treprostinil derivatives suitable for oral administration can be presented as, e.g., capsules (including push-fit capsules and soft capsules), cachets or tablets; as powders or granules; or as boluses, electuaries or pastes. For example, push-fit capsules can contain a treprostinil derivative in admixture with, e.g., a filler (e.g., lactose), a binder (e.g., a starch) and a lubricant (e.g., talc or magnesium stearate), and optionally a stabilizer. For soft capsules, a treprostinil derivative can be dissolved or suspended in a suitable liquid (e.g., a fatty oil, liquid paraffin or liquid polyethylene glycol), and a stabilizer can be added.

Compositions for oral administration can also be formulated as solutions or suspensions in an aqueous liquid and/or a non-aqueous liquid, or as oil-in-water liquid emulsions or water-in-oil liquid emulsions. Dispersible powder or granules of a treprostinil derivative can be mixed with any suitable combination of an aqueous liquid, an organic solvent and/or an oil and any suitable excipients (e.g., any combination of a dispersing agent, a wetting agent, a suspending agent, an emulsifying agent and/or a preservative) to form a solution, suspension or emulsion.

Treprostinil derivatives can also be formulated for parenteral administration by injection or infusion. Formulations for injection or infusion can be in the form of, e.g., solutions, suspensions or emulsions in oily or aqueous vehicles, and can contain excipients such as suspending agents, dispersing agents and/or stabilizing agents. For example, aqueous or non-aqueous (e.g., oily) sterile injection solutions can contain a treprostinil derivative along with excipients such as an antioxidant, a buffer, a bacteriostat and solutes that render the formulation isotonic with the blood of the subject. Aqueous or non-aqueous sterile suspensions can contain a treprostinil derivative along with excipients such as a suspending agent and a thickening agent, and optionally a stabilizer and an agent that increases the solubility of the treprostinil derivative to allow for the preparation of a more concentrated solution or suspension. As another example, a sterile aqueous solution for injection or infusion (e.g., subcutaneously or intravenously) can contain a treprostinil derivative, sodium chloride, a buffering agent (e.g., sodium citrate), a preservative (e.g., meta-cresol), and optionally a base (e.g., NaOH) and/or an acid (e.g., HCl) to adjust pH.

For a delayed or sustained release of a treprostinil derivative, a composition can be formulated as a depot that can be implanted in or injected into a subject, e.g., intramuscularly or subcutaneously. A depot formulation can be designed to deliver the treprostinil derivative over a longer period of time, e.g., over at least about 1 week, 2 weeks, 3 weeks, 1 month, 1.5 months, 2 months or longer. For example, a treprostinil derivative can be formulated with a polymeric material, a hydrophobic material (e.g., as an emulsion in an oil) and/or an ion-exchange resin, or as a sparingly soluble derivative (e.g., a sparingly soluble salt).

In some embodiments, a topical dosage form of a treprostinil derivative is formulated as a buccal or sublingual tablet or pill. Advantages of a buccal or sublingual tablet or pill include avoidance of first-pass metabolism and circumvention of gastrointestinal absorption. A buccal or sublingual tablet or pill can also be designed to provide faster release of the treprostinil derivative for more rapid uptake of it into systemic circulation. In addition to a therapeutically effective amount of a treprostinil derivative, the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

In addition, treprostinil derivatives can be formulated for intranasal administration. Intranasal administration avoids first-pass metabolism and can introduce a significant concentration of a treprostinil derivative to the central nervous system, which can reduce side-effects. An intranasal formulation can comprise a treprostinil derivative along with excipients such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) and/or a penetration enhancer.

Furthermore, treprostinil derivatives can be formulated for administration by oral inhalation. Advantages of administration by inhalation include selective deposition of the therapeutic agent in the lungs with less systemic side effects. In certain embodiments, a sterile aqueous solution for oral inhalation contains a treprostinil derivative, sodium chloride, a buffering agent (e.g., sodium citrate), optionally a preservative (e.g., meta-cresol), and optionally a base (e.g., NaOH) and/or an acid (e.g., HCl) to adjust pH.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

The compositions can be presented in unit dosage form as a single dose wherein all active and inactive ingredients are combined in a suitable system, and components do not need to be mixed to form the composition to be administered. The unit dosage form can contain an effective dose, or an appropriate fraction thereof, of a treprostinil derivative. A representative example of a unit dosage form is a tablet, capsule, or pill for oral uptake. For purposes of the content of a pharmaceutical composition, the term "active ingredient" encompasses a prodrug.

Alternatively, the compositions can be presented as a kit, wherein the active ingredient, excipients and carriers (e.g., solvents) are provided in two or more separate containers (e.g., ampules, vials, tubes, bottles or syringes) and need to be combined to form the composition to be administered. The kit can contain instructions for preparing and administering the composition (e.g., a solution to be injected intravenously).

Topical Compositions

Topical formulations for application to the skin or mucosa can be useful for transdermal or transmucosal administration of a therapeutic agent into the blood for systemic distribution. Advantages of topical administration can include avoidance of first-pass metabolism, circumvention of gastrointestinal absorption, delivery of a therapeutic agent with a relatively short biological half-life, more controlled release of the therapeutic agent, administration of a more uniform plasma dosing of the therapeutic agent, and improvement in user compliance.

In general and in addition to the disclosure on topical formulations described elsewhere herein, compositions suitable for topical administration include without limitation liquid or semi-liquid preparations such as sprays, gels, liniments, lotions, oil-in-water or water-in-oil emulsions such as creams, foams, ointments and pastes, and solutions or suspensions such as drops (e.g., eye drops, nose drops and ear drops). In some embodiments, a topical composition comprises a therapeutic agent dissolved, dispersed or suspended in a carrier. The carrier can be in the form of, e.g., a solution, a suspension, an emulsion, an ointment or a gel base, and can contain, e.g., petrolatum, lanolin, a wax (e.g., bee wax), mineral oil, a long-chain alcohol, polyethylene glycol or polypropylene glycol, a diluent (e.g., water and/or an alcohol [e.g., ethanol or propylene glycol]), an emulsifier, a stabilizer or a thickening agent, or a combination thereof. A topical composition can include, or a topical formulation can be administered by means of, e.g., a transdermal patch, a microneedle patch or an iontophoresis device. A transdermal patch can contain, e.g., a microporous membrane made of a suitable material (e.g., cellulose nitrate or acetate, propylene or a polycarbonate), a skin adhesive and backing material. A topical composition can deliver the therapeutic agent transdermally (including percutaneously and transmucosally) via a concentration gradient or an active mechanism (e.g., ionospheres).

Representative kinds of topical compositions are described below for purposes of illustration.

Topical Compositions Comprising a Permeation Enhancer

In some embodiments, a topical composition comprises a treprostinil derivative and a permeation enhancer. The composition can optionally contain an additional therapeutic agent.

The permeation enhancer increases the permeability of the skin or mucosa to the therapeutic agent(s). In certain embodiments, the permeation enhancer is N-lauroyl sarcosine, sodium octyl sulfate, methyl laurate, isopropyl myristate, oleic acid, glyceryl oleate or sodium lauryl sulfoacetate, or a combination thereof. In certain embodiments, the composition contains on a weight/volume (w/v) basis the permeation enhancer in an amount of about 1-20%, 1-15%, 1-10% or 1-5%. To enhance further the ability of the therapeutic agent(s) to penetrate the skin or mucosa, the composition can also contain a surfactant, an azone-like compound, an alcohol, a fatty acid or ester, or an aliphatic thiol.

The composition can further contain one or more additional excipients. Suitable excipients include without limitation solubilizers (e.g., $C_2$-$C_8$ alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

The topical composition can have any suitable dosage form, such as a solution (e.g., eye drop, nose drop or ear drop), a suspension, an emulsion, a cream, a lotion, a gel, an ointment, a paste, a jelly, a foam, or a spray. In some embodiments, the composition is applied to the skin or mucosa covering a surface area of about 10-800 cm$^2$, 10-400 cm$^2$ or 10-200 cm$^2$. The composition can be formulated for transdermal or transmucosal administration of the therapeutic agent(s) to the systemic circulation, e.g., as a transdermal patch or a microneedle patch.

Topical Compositions Comprising a Permeation Enhancer and a Volatile Liquid

In further embodiments, a topical composition comprises a treprostinil derivative, a permeation enhancer and a volatile liquid. The composition can optionally contain an additional therapeutic agent.

The permeation enhancer increases the permeability of the skin or mucosa to the therapeutic agent(s). In some embodiments, the permeation enhancer is selected from the group consisting of $C_8$-$C_{18}$ alkyl aminobenzoates (e.g., $C_8$-$C_{18}$ alkyl p-aminobenzoates), $C_8$-$C_{18}$ alkyl dimethylaminobenzoates (e.g., $C_8$-$C_{18}$ alkyl p-dimethylaminobenzoates), $C_8$-$C_{18}$ alkyl cinnamates, $C_8$-$C_{18}$ alkyl methoxycinnamates (e.g., $C_8$-$C_{18}$ alkyl p-methoxycinnamates), and $C_8$-$C_{18}$ alkyl salicylates. In certain embodiments, the permeation enhancer is octyl salicylate, octyl p-dimethylaminobenzoate or octyl p-methoxycinnamate, or a combination thereof.

The volatile liquid can be any volatile, skin- or mucosa-tolerant solvent. In certain embodiments, the volatile liquid is a $C_2$-$C_5$ alcohol or an aqueous solution thereof, such as ethanol or isopropanol or an aqueous solution thereof. An aerosol propellant (e.g., dimethyl ether) can be considered as a volatile liquid. In some embodiments, the volatile liquid functions as a carrier or vehicle of the composition.

The composition can optionally contain a thickening agent. Non-limiting examples of thickening agents include cellulosic thickening agents (e.g., ethyl cellulose, hydroxypropyl cellulose and hydroxypropyl methylcellulose), povidone, polyacrylic acids/polyacrylates (e.g., Carbopol® polymers), Sepigel® (polyacrylamide/isoparaffin/laureth-7), and the Gantrez® series of polymethyl vinyl ether/maleic anhydride copolymers (e.g., butyl ester of PMV/MA copolymer Gantrez® A-425).

In some embodiments, the composition contains on a weight basis about 0.1-5%, 0.5-5% or 1-5% of a treprostinil derivative, about 1-20%, 1-15% or 1-10% of the permeation enhancer, and about 40-98%, 45-95%, 50-90% or 60-80% of the volatile liquid. In further embodiments, the composition optionally contains on a weight basis about 1-40%, 1-30%, 1-20% or 5-20% water and/or about 0.1-15%, 0.5-10% or 1-5% of a thickening agent.

For purposes of illustration, in certain embodiments a topical spray composition contains about 0.1-5% w/v of a treprostinil derivative, about 2-10% w/v of octyl salicylate or octyl p-methyoxycinnamate, and about 95% aqueous ethanol as the carrier. In further embodiments, a topic gel composition comprises about 0.1-5% w/v of a treprostinil derivative, about 1-10% w/v of octyl salicylate or octyl p-methoxycinnamate, about 0.5-5% w/v of a Carbopol® polyacrylic acid, and about 70% aqueous ethanol as the carrier, and optionally about 1-10% w/v of a basic solution (e.g., 0.1 N NaOH). In additional embodiments, a topical lotion composition contains about 0.1-5% w/v of a treprostinil derivative, about 1-10% w/v of octyl salicylate or octyl p-methoxycinnamate, about 1-5% w/v of ethyl cellulose or hydroxypropyl cellulose, and about 90% aqueous ethanol as the carrier.

The composition can further comprise other excipients, such as a compounding agent (e.g., paraffin oil, silicone oil, a vegetable oil, or a fatty ester such as isopropyl myristate), a diluent, a co-solvent (e.g., acetone or a glycol ether such as diethylene glycol monoethyl ether), an emulsifier, a surfactant (e.g., an ethoxylated fatty alcohol, glycerol mono stearate or a phosphate ester), a stabiliser, an antioxidant or a preservative (e.g., a hydroxybenzoate ester), or a combination thereof. For example, a co-solvent and/or a surfactant can be used to maintain the therapeutic agent(s) in solution or suspension at the desired concentration.

The topical composition can have any suitable dosage form, such as a cream, a lotion, a gel, an ointment, a mousse, a spray or aerosol, or any transdermal device (e.g., a patch) that administers a drug by absorption through the skin or mucosa. In some embodiments, the topical composition is applied to the skin or mucosa covering a surface area of about 10-800 cm$^2$, 10-400 cm$^2$ or 10-200 cm$^2$.

Topical Compositions Including a Permeation Enhancer and Another Excipient

In yet further embodiments, a topical composition comprises a treprostinil derivative, a permeation enhancer, and at least one of a lipophilic solvent, a formulation base and a thickener. In some embodiments, the composition contains a lipophilic solvent and a formulation base, or the same substance can function as both a lipophilic solvent and a formulation base. In further embodiments, the composition contains a lipophilic solvent, a formulation base and a thickener. The composition can optionally comprise an additional therapeutic agent.

The permeation enhancer increases the permeability of the skin or mucosa to the therapeutic agent(s). Non-limiting examples of permeation enhancers include dimethyl sulfoxide (DMSO), decylmethylsulfoxide, laurocapram, pyrrolidones (e.g., 2-pyrrolidone and N-methyl-2-pyrrolidine), surfactants, alcohols (e.g., oleyl alcohol), polyethylene glycol (e.g., PEG 400), diethylene glycol monoethyl ether, oleic acid, and fatty acid esters (e.g., isopropyl myristate, methyl laurate, glycerol monooleate, and propylene glycol monooleate).

Non-limiting examples of liphophilic solvents include lipophilic alcohols (e.g., hexylene glycol, octyldodecanol, oleyl alcohol and stearyl alcohol), polyethylene glycol (e.g., PEG 100, PEG 300, PEG 400 and PEG 3350), diethylene glycol monoethyl ether, polysorbates (e.g., Tween® 20 to 80), Labrasol®, fatty acid esters (e.g., isopropyl myristate and diisopropyl adipate), diethyl sebacate, propylene glycol monocaprylate, propylene glycol laurate, mono- and di-glycerides (e.g., Capmul® MCM), medium-chain triglycerides, caprylic/capric triglyceride, glyceryl monocaprylate, glyceryl mono-oleate, glyceryl mono-linoleate, glycerol oleate/propylene glycol, mineral oil, and vegetable oils.

A lipophilic solvent may also function as a formulation base or carrier. For example, polyethylene glycol (e.g., from PEG 100 to PEG 3500, such as PEG 300, PEG 400 and PEG 3350) can function as a liphophilic solvent and a formulation base.

The composition can also contain a hydrophilic solvent, such as a $C_1$-$C_5$ alcohol (e.g., ethanol, isopropanol, glycerol, propylene glycol and 1,2-pentanediol) and/or water.

The composition can contain a thickener to increase the viscosity and/or the physical stability of the composition. Examples of thickeners include without limitation glycerol, stearyl alcohol, and polymers (e.g., polydimethylsiloxane [dimethicone] and Carbopol® polymers).

In some embodiments, the composition further contains an antioxidant. Non-limiting examples of antioxidants include butylated hydroxyanisole (BHA), butylated hydroxytoluene (BHT), tocopherols (e.g., Vitamin E and esters thereof), flavinoids, glutathione, ascorbic acid and esters thereof, DMSO, and chelating agents (e.g., EDTA and citric acid).

In certain embodiments, the topical composition comprises on a w/w basis about 0.1-5% or 0.5-5% of a treprostinil derivative, about 2-30% or 5-20% of a permeation enhancer, about 20-80% or 30-70% of a lipophilic solvent that may also function as a formulation base, about 0.1-10% or 1-7.5% of a thickener, and about 0.01-2% or 0.05-1% of an antioxidant. As a non-limiting example, a topical composition can contain a treprostinil derivative, PEG 400 and/or PEG 3350 as lipophilic solvent(s) and formulation base(s), diethylene glycol monoethyl ether, oleyl alcohol and/or isopropyl myristate as permeation enhancer(s), stearyl alcohol as a thickener, and BHT as an antioxidant.

The topical composition can have any suitable dosage form, such as a cream, a lotion, a gel, an ointment, a jelly, a paste, or any transdermal device (e.g., a patch) that administers a drug by absorption through the skin or mucosa.

Topical Compositions Comprising a Permeation Enhancer and an Adhesive

In additional embodiments, a topical composition comprises a treprostinil derivative, a permeation enhancer and an adhesive. The composition can optionally contain an additional therapeutic agent.

The permeation enhancer increases the permeability of the skin or mucosa to the therapeutic agent(s). The permeation enhancer can be, e.g., a fatty acid ester having a fatty acyl chain length of $C_8$-$C_{20}$ or $C_{12}$-$C_{18}$ and a $C_1$-$C_6$ or $C_2$-$C_4$ alcohol component (e.g., isopropanol). In certain embodiments, the permeation enhancer is isopropyl myristate or isopropyl palmitate. In some embodiments, the permeation enhancer is in an amount of about 0.1-20%, 0.5-15%, 1-15%, 2-12% or 4-10% by weight of the composition or the skin-contacting layer of a transdermal patch.

The adhesive maintains contact of the topical composition to the skin or mucosa. Non-limiting examples of adhesives include acrylics/acrylates (e.g., polyacrylates, including polyalkyl acrylates and Duro-Tak® polyacrylates), polyvinyl acetate, ethylenevinylacetate copolymers, polysiloxanes, polyurethanes, plasticized polyether block amide copolymers, natural and synthetic rubbers, plasticized styrene-butadiene rubber block copolymers (e.g., Duro-Tak® 87-6173), and mixtures thereof.

The topical composition can comprise one or more additional excipients. The additional excipient(s) can be, e.g., a diluent, an emollient, a plasticizer, or an agent that reduces irritation to the skin or mucosa, or a combination thereof.

In certain embodiments, the topical composition prior to application to the skin or mucosa is substantially free of water, tetraglycol (glycofurol) and/or a hydrophilic organic solvent (e.g., a $C_1$-$C_5$ alcohol).

The composition can administer the therapeutic agent(s) transdermally (including percutaneously and transmucosally) through a body surface or membrane such as intact unbroken skin or intact unbroken mucosal tissue into the systemic circulation.

In some embodiments, the topical composition is in the form of a transdermal patch for application to the skin or mucosa. The patch has a skin- or mucosa-contacting layer ("skin-contacting layer" for simplicity) laminated or otherwise attached to a support layer. The skin-contacting layer can be covered by a removable release liner before use to protect the skin-contacting surface and to keep it clean until it is applied to the skin or mucosa. The support layer of the patch acts as a support for the skin-contacting layer and as a barrier that prevents loss of the therapeutic agent(s) in the skin-contacting layer to the environment. The material of the support layer is compatible with the therapeutic agent(s), the permeation enhancer and the adhesive, and is minimally permeable to the components of the patch. The support layer can be opaque to protect the components of the patch from degradation via exposure to ultraviolet light. The support layer is also capable of binding to and supporting the adhesive layer, yet is sufficiently pliable to accommodate the movements of the subject using the patch. The material of the support layer can be, e.g., a metal foil, a metalized polyfoil, or a composite foil or film containing a polymer (e.g., a polyester [such as polyester terephthalate] or aluminized polyester, polyethylene, polypropylene, polytetrafluoroethylene, a polyethylene methyl methacrylate block copolymer, a polyether block amide copolymer, a polyurethane, polyvinylidene chloride, nylon, a silicone elastomer, rubber-based polyisobutylene, styrene, or a styrene-butadiene or styrene-isoprene copolymer). The release liner can be made of the same material as the support layer, or can be a film coated with an appropriate release surface.

Therapeutic Uses of Treprostinil Derivatives

In some embodiments, the compounds described herein are used to treat pulmonary hypertension. Accordingly, the disclosure provides a method of treating pulmonary hypertension, comprising administering to a subject in need of treatment a therapeutically effective amount of a treprostinil derivative, or a pharmaceutically acceptable salt, solvate, clathrate or polymorph thereof. Treprostinil derivatives include prodrugs of treprostinil. An additional therapeutic agent can optionally be administered to treat pulmonary hypertension.

Pulmonary hypertension is an increase of blood pressure in the lung vasculature, including the pulmonary artery, pulmonary vein and pulmonary capillaries. Thus, pulmonary hypertension encompasses pulmonary arterial hypertension (PAH) and pulmonary venous hypertension (PVH) (e.g., congestive heart failure). More broadly, pulmonary hypertension encompasses:

WHO Group I—pulmonary arterial hypertension, including idiopathic PAH, heritable PAH (e.g., BMPR2, ALK1 and endoglin [with or without hereditary hemorrhagic telangiectasia]), drug- and toxin-induced PAH, PAH associated with various conditions (e.g., connective tissue disease, HIV infection, portal hypertension, congenital heart disease, schistosomiasis, and chronic hemolytic anemia [e.g., sickle cell disease]), persistent pulmonary hypertension of the newborn, pulmonary veno-occlusive disease (PVOD), and pulmonary capillary hemangiomatosis (PCH);

WHO Group II—pulmonary hypertension owing to left heart disease, including systolic dysfunction, diastolic dysfunction and valvular heart disease;

WHO Group III—pulmonary hypertension owing to lung disease and/or hypoxia, including chronic obstructive pulmonary disease (COPD), interstitial lung disease, other pulmonary diseases with mixed restrictive and obstructive pattern, sleep-disordered breathing, alveolar hypoventilation disorders, chronic exposure to high altitude, and developmental abnormalities;

WHO Group IV—chronic thromboembolic pulmonary hypertension (CTEPH); and

WHO Group V—pulmonary hypertension with unclear multifactorial mechanisms, including hematologic diseases (e.g., myeloproliferative disease and splenectomy), systemic diseases (e.g., sarcoidosis, pulmonary Langerhans cell histiocytosis, lymphangioleiomyomatosis, neurofibromatosis and vasculitis), metabolic disorders (e.g., glycogen storage disease, Gaucher disease and thyroid diseases), and other causes (e.g., tumoral obstruction, fibrosing mediastinitis, and chronic renal failure on dialysis).

The therapeutically effective amount and frequency of administration of a treprostinil derivative to treat pulmonary hypertension may depend on various factors, including the type of pulmonary hypertension, the severity of the condition, the mode of administration, the age, body weight, general health, gender and diet of the subject, and the response of the subject to the treatment, and can be determined by the treating physician. In certain embodiments, the effective dose of a treprostinil derivative per day is about 0.1-100 mg, 0.1-50 mg, 0.5-50 mg, 0.5-25 mg, 0.5-10 mg, 1-10 mg or 1-5 mg, or as deemed appropriate by the treating physician, which can be administered in a single dose or in divided doses. In further embodiments, the effective dose of a treprostinil derivative per day is about 0.001-2 mg/kg, 0.005-1 mg/kg, 0.01-0.5 mg/kg or 0.01-0.1 mg/kg body weight, or as deemed appropriate by the treating physician.

In some embodiments, a treprostinil derivative is administered, in a single dose or in multiple doses, daily (including one, two, three or more times daily), every two days, every three days, twice weekly, thrice weekly, weekly, every 2 weeks, every 3 weeks, monthly, every 6 weeks, every 2 months or every 3 months, or as deemed appropriate by the treating physician. In further embodiments, a treprostinil derivative is administered under a chronic dosing regimen. In certain embodiments, a therapeutically effective amount of a treprostinil derivative is administered over a period of at least 2 weeks, 3 weeks, 1 month, 1.5 months, 2 months, 3 months, 4 months, 5 months, 6 months or longer.

A treprostinil derivative can be administered via any suitable route. Potential routes of administration of a treprostinil derivative include without limitation oral, parenteral (including intramuscular, subcutaneous, intradermal, intravascular, intravenous, intraarterial, intramedullary and intrathecal), intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). In certain embodiments, a treprostinil derivative is administered orally. In other, embodiments, a treprostinil derivative is administered topically (e.g. dermally, transdermally, mucosally, transmucosally, intranasally, pulmonarily [e.g., by inhalation], or sublingually). In further embodiments, a treprostinil derivative is administered parenterally (e.g., subcutaneously or intravenously, including by injection or infusion).

In some embodiments, a treprostinil derivative is used to treat PAH. In further embodiments, an additional therapeutic agent is administered in combination with the treprostinil derivative to treat PAH. The additional therapeutic agent can be administered concurrently with or sequentially to (before or after) administration of the treprostinil derivative. If administered concurrently with the treprostinil derivative, the additional therapeutic agent can be contained in the same composition as the treprostinil derivative or in separate compositions.

In certain embodiments, the additional therapeutic agent for the treatment of PAH is selected from the group consisting of:

vasoactive agents, including without limitation prostaglandins and prostanoids (e.g., prostacyclin [prostaglandin $I_2$] and beraprost), endothelin receptor (e.g., $ET_A$ and/or $ET_B$) antagonists (e.g., ambrisentan, bosentan, sitaxentan and Actelion-1), phosphodiesterase type 5 (PDE5) inhibitors (e.g., sildenafil and tadalafil), activators of soluble guanylate cyclase (e.g., cinaciguat and riociguat), and analogs and derivatives thereof;

diuretics, including without limitation thiazide diuretics (e.g., bendroflumethiazide, chlorothiazide, epitizide and hydrochlorothiazide), thiazide-like diuretics (e.g., chlorthalidone, indapamide and metolazone), and analogs and derivatives thereof;

anticoagulants, including without limitation vitamin K antagonists (e.g., acenocoumarol, atromentin, coumarin, phenindione, phenprocoumon and warfarin), direct thrombin inhibitors (e.g., argatroban, dabigatran, hirudin, lepirudin and bivalirudin), direct factor Xa inhibitors (e.g., apixaban, betrixaban, darexaban, edoxaban, eribaxaban, letaxaban and rivaroxaban), heparin and derivatives thereof (e.g., unfractionated heparin, low molecular weight heparin, fondaparinux and idraparinux), others (e.g., antithrombin, batroxobin and hementin), and analogs, derivatives and fragments thereof; and other kinds of therapeutic agents, including without limitation cardiac glycosides (e.g., digoxin, acetyldigoxin and digoxigenin) and oxygen therapy.

EXAMPLES

Additional embodiments are provided in the following, non-limiting examples.

Four assays on compounds were carried out by the following methods with the results shown in Table I.

(Test 1) Human liver microsomal stability assay was conducted by incubating 0.5 uM test compounds at 37° C. for up to 45 minutes in 50 mM of potassium phosphate buffer (pH 7.4) containing 0.5 mg of microsomal protein and 50 µL of NADPH generating system (7.8 mg of glucose 6-phosphate, 1.7 mg of NADPH and 6 U of glucose 6-phosphate dehydrogenase per mL in 2% w/v of sodium bicarbonate). At 0, 5, 15, 30 and 45 min., an aliquot was taken, quenched with internal standard containing stop solution. No co-factor controls at 45 minutes were also prepared. After incubation, the samples were analyzed by LC-MS/MS. Peak area ratios of analyte to internal standard were used to calculate the intrinsic clearance. The intrinsic clearance ($CL_{int}$) was determined from the first order elimination constant by non-linear regression. Formation of the active drug Compound A over the time course was also monitored by LC-MS/MS analysis.

(Test 2) Human plasma stability assay was conducted by incubating 0.5 uM test compounds at 37° C. for up to 120 minutes in heparinated human plasma. At 0, 5, 15, 30, 60 and 120 and 240 min., an aliquot was taken, quenched with internal standard containing stop solution. After incubation, the samples were analyzed by LC-MS/MS. Peak area ratios of analyte to internal standard were used to calculate the half-life. Formation of the active drug Compound A over the time course was also monitored by LC-MS/MS analysis.

(Test 3) Human skin homogenate stability assay was conducted in a similar way as the human liver microsomal stability assay, by incubating 0.5 uM test compounds at 37° C. for up to 45 minutes in 50 mM of potassium phosphate buffer (pH 7.4) containing 0.5 mg of human skin homogenate protein and 50 µL of NADPH generating system (7.8 mg of glucose 6-phosphate, 1.7 mg of NADPH and 6 U of glucose 6-phosphate dehydrogenase per mL in 2% w/v of sodium bicarbonate). At 0, 5, 15, 30 and 45 min., an aliquot was taken, quenched with internal standard containing stop solution. No co-factor controls at 45 minutes were also prepared. After incubation, the samples were analyzed by LC-MS/MS. Peak area ratios of analyte to internal standard were used to calculate the intrinsic clearance. The intrinsic clearance ($CL_{int}$) was determined from the first order elimination constant by non-linear regression. Formation of the active drug Compound A over the time course was also monitored by LC-MS/MS analysis.

(Test 4) Human hepatocyte stability assay was conducted by incubating 0.5 uM test compound at 37° C. for up to 240 minutes. Cryopreserved human hepatocytes were obtained from Celsis IVT (Baltimore, Md.). Cells were thawed according to vendor's instructions and were suspended in William's Medium E to 0.5 million cells/mL. Test compounds were spiked into the cell suspension to initiate the reactions. At 0, 10, 30, 60, 120 and 240 min., an aliquot was taken, quenched with internal standard containing stop solution. After incubation, the samples were analyzed by LC-MS/MS. Peak area ratios of analyte to internal standard were used to calculate the intrinsic clearance. The intrinsic clearance ($CL_{int}$) was determined from the first order elimination constant by non-linear regression. Formation of the active drug Compound A over the time course was also monitored by LC-MS/MS analysis.

Assay results (half life) are shown in Table I. In Table I, the code for the results of the assay testing is:

A=<15 min

B=15-30 min

C=31-60 min

D=>60 min

TABLE I
| Compd No. | MW (g/mol) | m/z [M + Na]+ | Test 1 $T_{1/2}$ | Test 2 $T_{1/2}$ | Test 3 $T_{1/2}$ | Test 4 $T_{1/2}$ |
| --- | --- | --- | --- | --- | --- | --- |
| A | 390 | 413 | | | | |
| 1 | 444.62 | 467.62 | A | A | | |
| 2 | 443.63 | 466.63 | A | D | | C |
| 3 | 503.68 | 526.68 | | | | |
| 4 | 450.6 | 473.6 | A | A | | |
| 5 | 460.62 | 483.62 | A | A | | |
| 6 | 476.62 | 499.62 | A | A | | |
| 7 | 433.59 | 456.59 | B | D | | B |
| 8 | 432.61 | 455.61 | C | | | |
| 9 | 434 | 457 | A | | | |
| 10 | 448 | 471 | A | | | |
| 11 | 447 | 470 | A | D | | |
| 12 | 461 | 484 | A | D | | |
| 13 | 475 | 498 | A | D | | A |
| 14 | 471 | 494 | A | D | D | A |
| 15 | 404 | 427 | A | A | A | |
| 16 | 460 | 483 | A | B | B | |
| 17 | 460 | 483 | A | C | B | |
| 18 | 474 | 497 | A | D | D | |
| 19 | 484 | 507 | A | C | B | |
| 20 | 432 | 455 | A | C | A | |
| 21 | 521 | 544 | A | D | | |
| 22 | 488 | 511 | A | D | D | |
| 23 | 488 | 511 | A | D | | |
| 24 | 472 | 495 | A | D | | |
| 25 | 476 | 499 | A | D | C | |
| 26 | 446 | 489 | A | B | B | |
| 27 | 532 | 555 | A | D | | |
| 28 | 446 | 469 | A | B | | |
| 57 | 372 | 395 | D | D | | D |
| 60 | 446 | | A | C | C | |
| 61 | 446 | | A | B | C | |
| 62 | 460 | | A | C | D | |
| 63 | 460 | | A | C | C | |
| 64 | 502 | | A | D | D | |
Compounds 60 to 64 have the structure shown below:
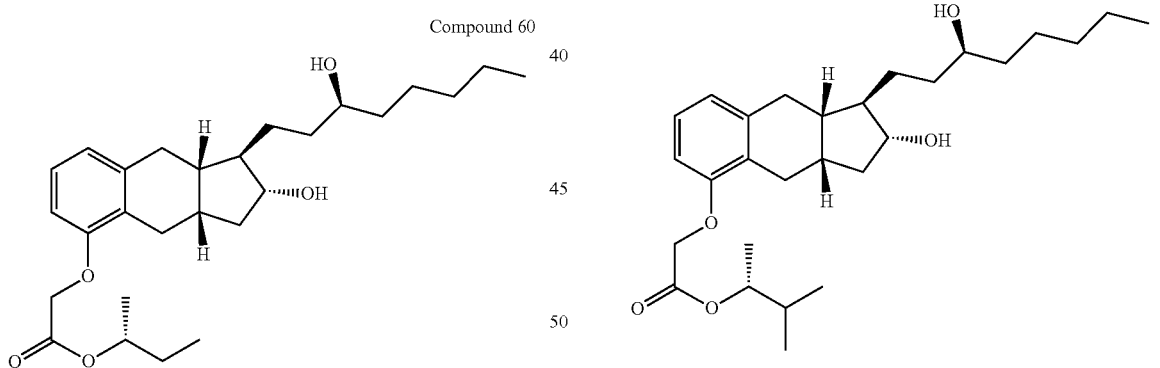
Compound 60
Compound 61
-continued
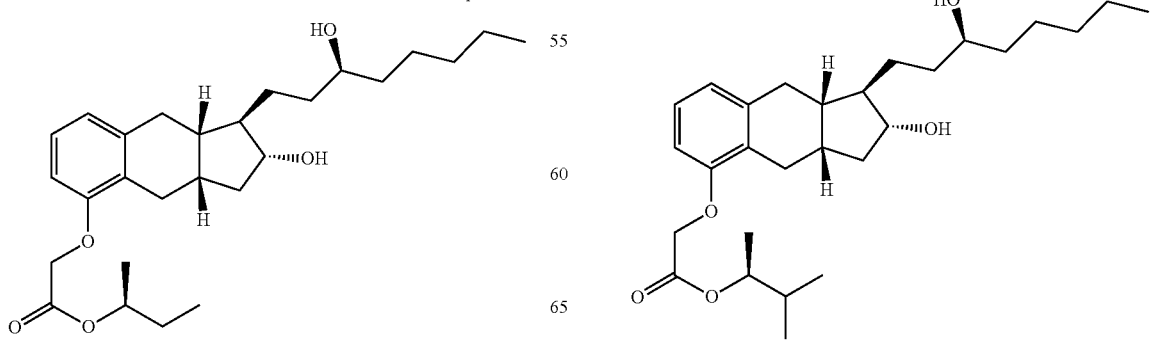
Compound 62
Compound 63

-continued

Compound 64

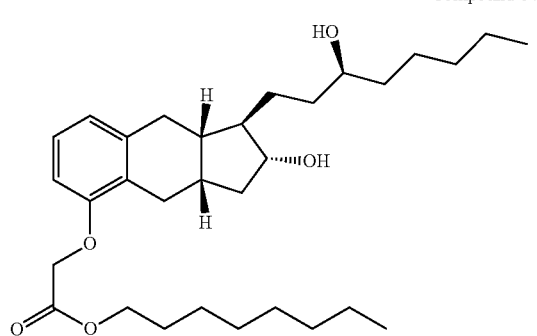

Examples of Synthesis of Treprostinil Derivatives

The following representative syntheses are shown for compounds according to Formulae I, II, and III.

Example 1. Synthesis of: 2-[2-Hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (94 mg, 0.2 mmol), trifluoroethylamine (54 mg, 0.6 mmol) and DIPEA (104 μl, 0.6 mmol) in DMF (2 ml) was treated with HATU and stirred 24 hr at RT. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH (4 ml), treated with Amberlite IR120H and stirred 24 hr. The reaction mixture was filtered and concentrated to yield 2-[2-hydroxy-1-(3-hydroxy-octyl)-2,3,3a,4,9,9a-hexahydro-1H-cyclopenta[b]naphthalen-5-yloxy]-N-(2,2,2-trifluoro-ethyl)-acetamide (46 mg) as an oil. $^1$HNMR (400 MHz, CDCl$_3$) δ 7.06 (d, 1H, J=7.6); 6.80 (d, 1H, J=7.2); 6.63 (d, 1H, J=8.0); 4.86 (quint., 1H, J=6.4); 4.60 (s, 2H); 3.7-3.8 (m, 1H); 3.55-3.65 (m, 1H); 2.85-2.95 (ddd, 1H); 2.70-2.80 (dd, 1H); 2.50-2.60 (ddd, 1H); 2.40-2.50 (dd, 1H); 2.15-2.3 (m, 2H); 1.75-1.95 (m, 2H); 1.24-1.70 (m, 17H); 1.20 (d, 3H, J=6.4); 0.85-0.95 (m, 8H); MS: m/z 494 [M+Na]$^+$ Example 2: Synthesis of: [2-Hydroxy-1-(3-hydroxy-octyl)-2,3,3a,4,9,9a-hexahydro-1H-cyclopenta[b]naphthalen-5-yloxy]-acetic acid 1,2-dimethyl-propyl ester

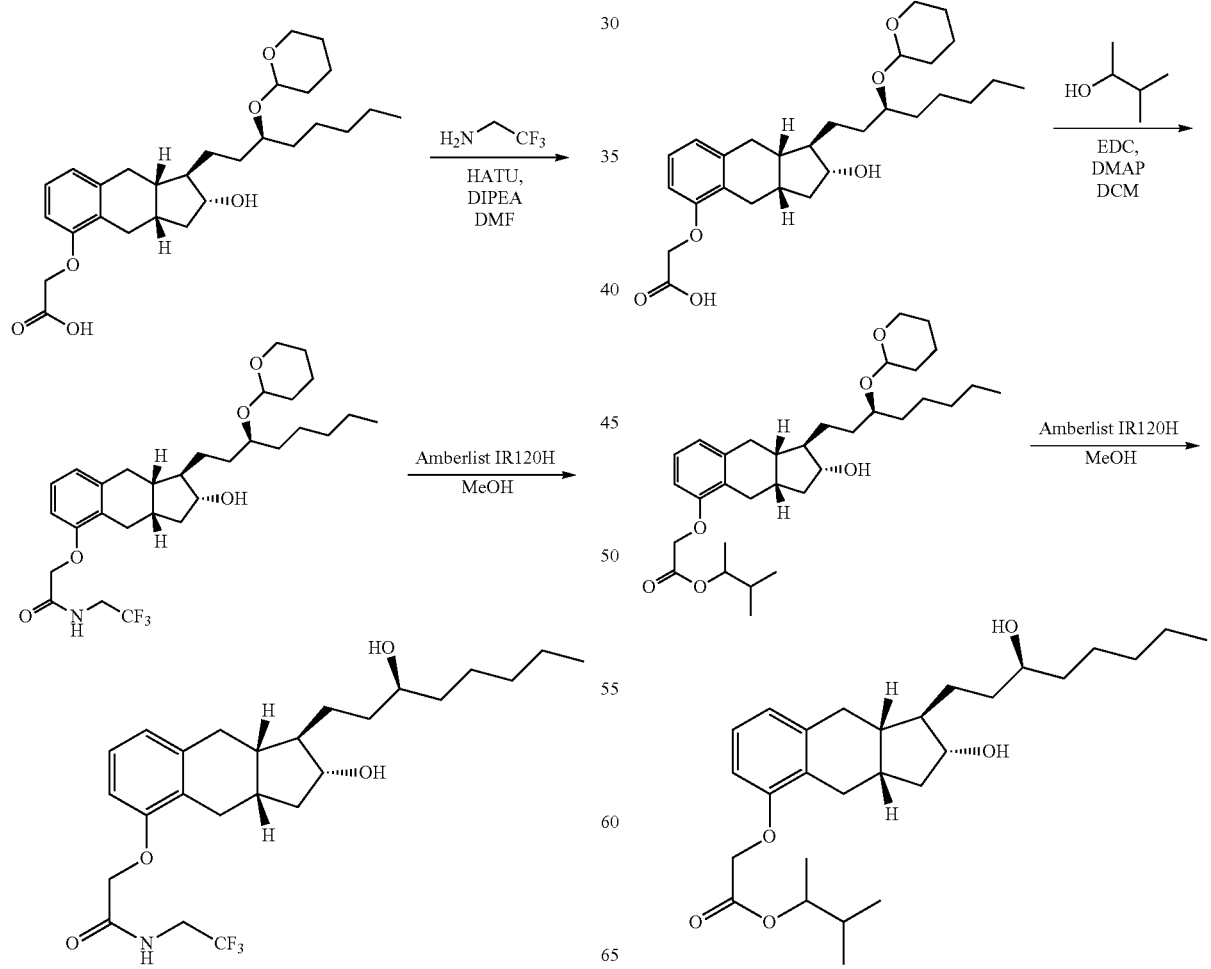

A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (47 mg, 0.1 mmol), 3-methyl-2-butanol (26 mg, 0.3 mmol) and DMAP (12 mg, 0.1 mmol) in DCM (1 ml) was treated with EDC (26 mg, 0.14 mmol) and stirred 24 hr at RT. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield [2-hydroxy-1-(3-hydroxy-octyl)-2,3,3a,4,9,9a-hexahydro-1H-cyclopenta[b]naphthalen-5-yloxy]-acetic acid 1,2-dimethyl-propyl ester (16 mg) as an oil. $^1$HNMR (400 MHz, CDCl$_3$) δ 7.06 (d, 1H, J=7.6); 6.80 (d, 1H, J=7.2); 6.63 (d, 1H, J=8.0); 4.86 (quint., 1H, J=5.6); 4.60 (s, 2H); 3.7-3.8 (m, 1H); 3.55-3.80 (m, 1H); 3.55-3.70 (m, 1H); 2.85-2.95 (dd, 1H); 2.50-2.80 (dd, 1H); 2.50-2.60 (dd, 1H); 2.40-2.60 (dd, 1H); 2.15-2.30 (m, 2H); 1.75-1.95 (m, 2H); 1.35-1.80 (m, 17H); 1.19 (d, 3H, J=6.4); 0.85-0.95 (m, 8H); MS: m/z 483 [M+Na]$^+$ Example 3: Synthesis of: treprostinil 2-hydroxy lactone

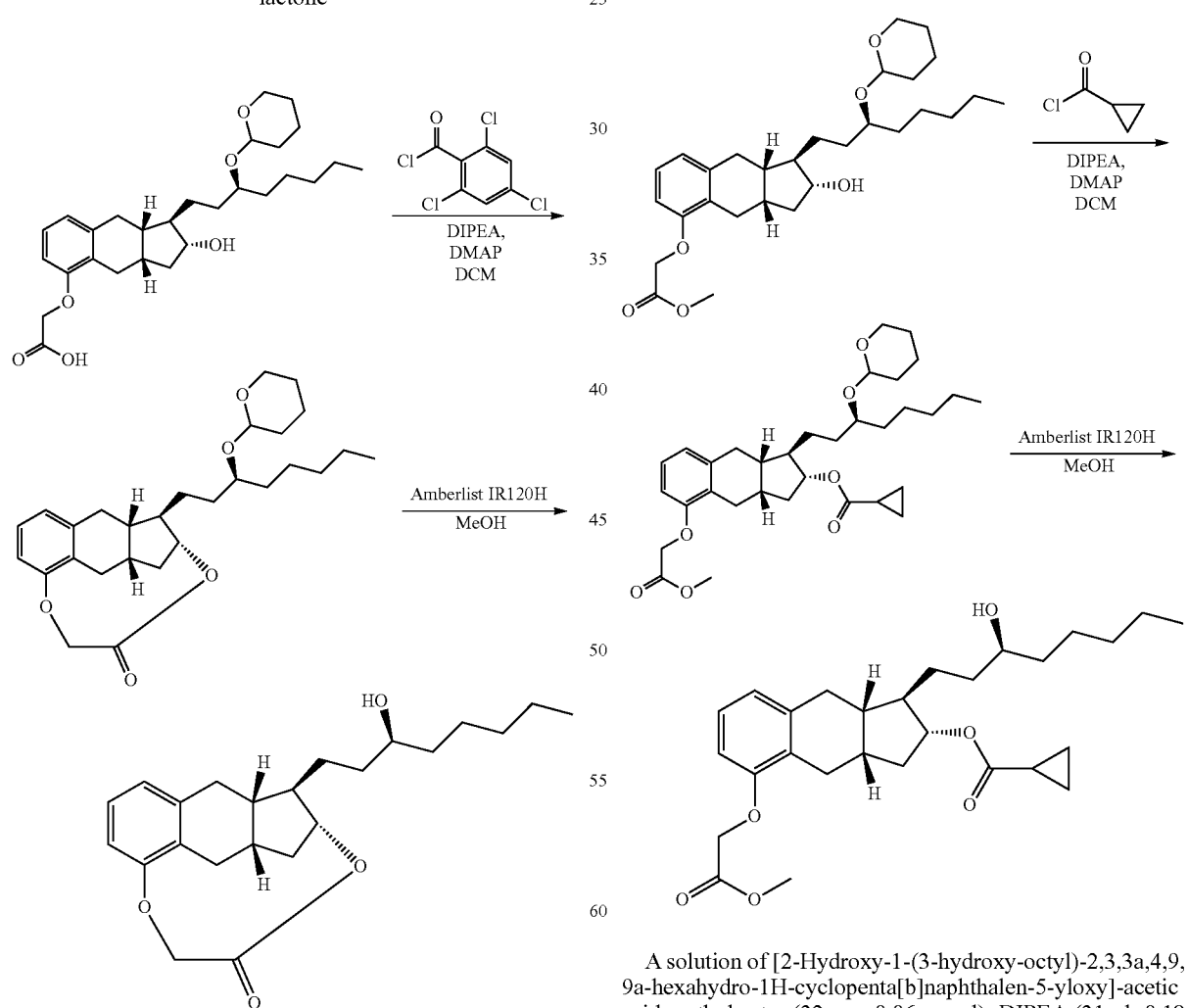

A solution of {2-Hydroxy-1-[3-(tetrahydro-pyran-2-yloxy)-octyl]-2,3,3a,4,9,9a-hexahydro-1H-cyclopenta[b]naphthalen-5-yloxy}-acetic acid (47 mg, 0.1 mmol) and DMAP (26 mg, 0.2 mmol) in DCM (1 ml) was treated with 2,4,6-trichlorobenzoyl chloride (27 mg, 0.11 mmol) and stirred 24 hr at RT. The reaction mixture was diluted with ethyl acetate and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield treprostinil 2-hydroxy lactone (8 mg) as an oil. $^1$HNMR (400 MHz, CDCl$_3$) δ 7.03 (dd, 1H, J=8.4 Hz, J=7.6 Hz); 6.74 (d, 1H, J=7.6 Hz); 6.55 (d, 1H, J=8.4 Hz) 4.53 (m, 1H); 4.46 (d, 1H, J=15.2 Hz); 4.31 (d, 1H, J=15.2 Hz); 3.53 (m, 1H); 2.5 (m, 1H); 2.8 (dd, 1H); 2.6 (dd, 1H); 2.2-2.55 (m, 4H); 1.53 (m, 4H); 1.35-1.47 (m, 4H); 1.3 (m, 6H); 0.89 (m, 3H); MS: m/z 395 [M+Na]$^+$ Example 4: Synthesis of: Cyclopropanecarboxylic acid 1-(3-hydroxy-octyl)-5-methoxycarbonyl-methoxy-2,3,3a,4,9,9a-hexahydro-1H-cyclopenta[b]naphthalen-2-yl ester A solution of [2-Hydroxy-1-(3-hydroxy-octyl)-2,3,3a,4,9,9a-hexahydro-1H-cyclopenta[b]naphthalen-5-yloxy]-acetic acid methyl ester (32 mg, 0.06 mmol), DIPEA (31 µl, 0.18 mmol) and DMAP (1 crystal) in DCM (2 ml) was treated with cyclopropanecarbonyl chloride (8 µl, 0.08 mmol) and stirred for 24 hr at RT under nitrogen. The reaction mixture was diluted with MTBE and washed with saturated sodium bicarbonate solution and brine, dried over sodium sulfate and concentrated under vacuum. The residue was purified by silica gel chromatography. This resulting material was dissolved in MeOH/THF (4 ml), treated with Amberlite IR120H and stirred 24 hr. The reaction mixture was filtered and concentrated to yield cyclopropanecarboxylic acid 1-(3-hydroxy-octyl)-5-methoxycarbonylmethoxy-2,3,3a,4,9,9a-hexahydro-1H-cyclopenta[b]naphthalen-2-yl ester (32 mg) as an oil. $^1$HNMR: (400 MHz, DMSO-d$_6$) δ 7.06 (d, 1H, J=7.6); 6.80 (d, 1H, J=7.2); 6.63 (d, 1H, J=8.8); 4.78 (s, 2H); 4.1-4.2 (m, 1H); 4.05-4.50 (m, 1H); 3.68 (s, 3H); 2.6-2.8 (m, 2H); 2.4-2.5 (m, 2H); 2.20-2.35 (m, 1H); 2.10-2.20 (m, 1H); 1.8-1.95 (m, 1H); 1.10-1.16 (m, 15H); 0.95-1.10 (m, 1H); 0.70-0.90 (m, 7H); MS: m/z 495 [M+Na]$^+$ Example 5: Synthesis of Formula III Compound A solution of acrylic acid 1-[2-(2-acryloyloxy-5-methoxycarbonylmethoxy-2,3,3a,4,9,9a-hexahydro-1H-cyclopenta[b]naphthalen-1-yl)-ethyl]-hexyl ester (51 mg, 0.1 mmol) in chloroform (20 ml) is treated with a solution of (PCy3)2Cl2Ru=CHPh (19 mg, 0.023 mmol) in chloroform (3 ml) and stirred 24 hr at RT. TEA (1 ml) is added and the solution is concentrated under vacuum. The residue is purified by silica gel chromatography to yield the title compound.

Additional synthetic schemes are shown below:

Example 6 (Formula I Compound)

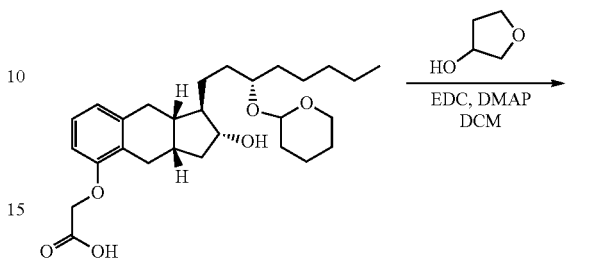

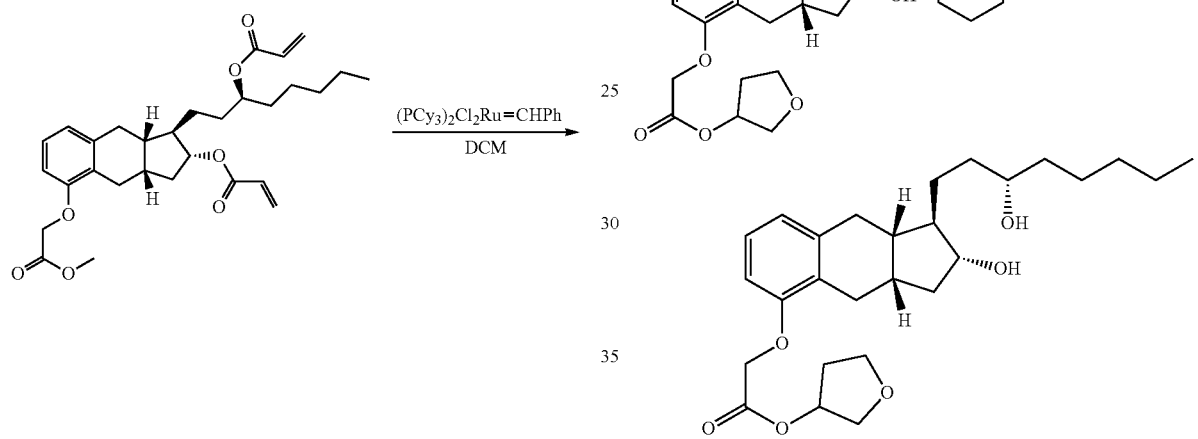

Example 7 (Formula I Compound)

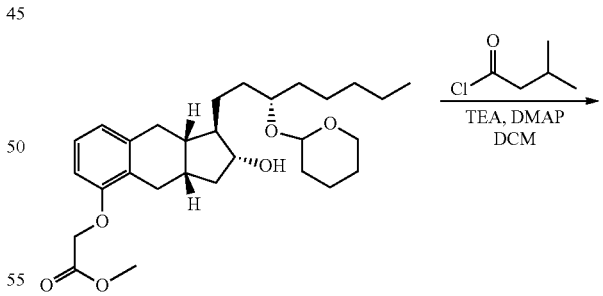

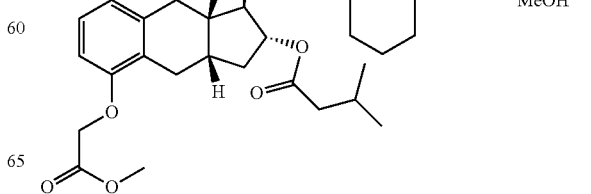

-continued

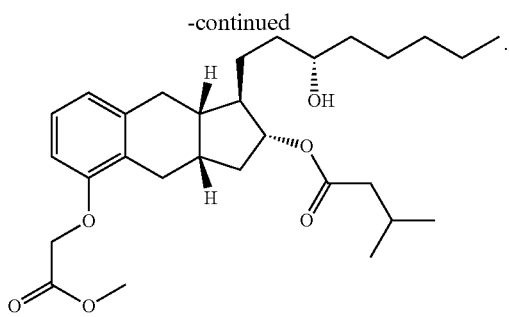

What is claimed is:

1. A transdermal patch comprising a topical composition comprising a compound of Formula (I) or a pharmaceutically acceptable salt, polymorph or stereoisomer thereof:

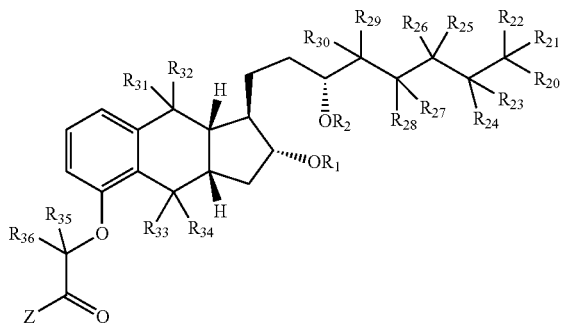

(I)

wherein:

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$ and $R_{36}$ are independently H or deuterium;

Z is —OH, —$OR_{11}$, —$N(R_{11})R_{12}$, —$SR_{11}$ or $P_1$;

$R_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, substituted alkylcycloheteroalkyl, aryl, substituted aryl, alkylaryl, substituted alkylaryl, heteroaryl, substituted heteroaryl, alkylheteroaryl, or substituted alkylheteroaryl;

$R_{12}$ is H, haloalkyl, heteroalkyl, cycloheteroalkyl, alkylcycloalkyl, alkylcycloheteroalkyl, aryl, or heteroaryl;

$P_1$ is selected from:

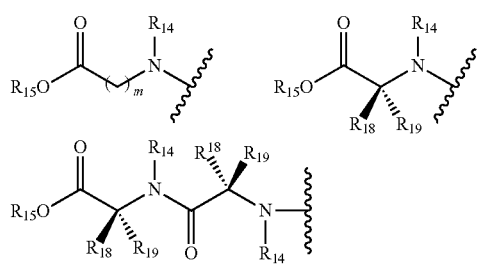

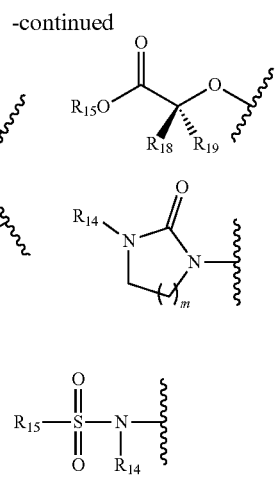

wherein:

m is 1, 2, 3 or 4;

$R_{14}$ and $R_{15}$ are independently in each occurrence selected from H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl, or $R_{14}$ and $R_{15}$ together with the atoms to which they are attached optionally form a 5- to 7-membered ring incorporating two ring heteroatoms chosen from N, O and S which is unsubstituted or substituted with 1, 2 or 3 substituents independently selected from halo, methyl and methoxy;

$R_{18}$ and $R_{19}$ are independently in each occurrence hydrogen or alkyl, wherein the alkyl is unsubstituted or substituted with 1 substituent selected from halo, hydroxy, alkoxy, amino, thio, methylthio, —C(O)OH, —C(O)O-(alkyl), —$CONH_2$, aryl and heteroaryl, wherein the aryl or heteroaryl is unsubstituted or substituted with a substituent selected from alkyl, halo, haloalkyl, hydroxy, alkoxy, and haloalkoxy;

$R_{14}$ and $R_{18}$ together with the atoms to which they are attached optionally form a 5- to 7-membered ring;

$R_{14}$ and $R_{19}$ together with the atoms to which they are attached optionally form a 5- to 7-membered ring;

$R_{15}$ and $R_{18}$ together with the atoms to which they are attached optionally form a 5- to 7-membered ring; and $R_{15}$ and $R_{19}$ together with the atoms to which they are attached optionally form a 5- to 7-membered ring; and $R_1$ and $R_2$ are independently H or $P_2$, wherein at least one of $R_1$ and $R_2$ is $P_2$, and wherein $P_2$ is selected from:

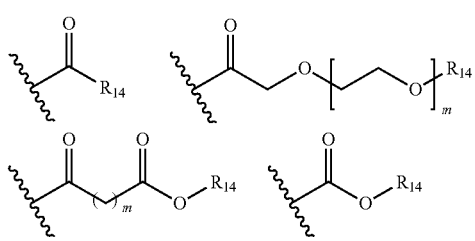

-continued

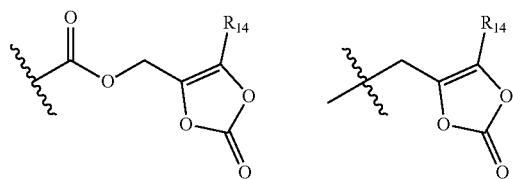

wherein:

m is 1, 2, 3 or 4; and

R$_{14}$ is independently in each occurrence selected from H, alkyl, cycloalkyl, alkylcycloalkyl, haloalkyl, heteroalkyl, substituted alkyl, aryl, heteroaryl, arylalkyl, heteroarylalkyl, substituted aryl, substituted heteroaryl, substituted arylalkyl, and substituted heteroarylalkyl.

2. The transdermal patch of claim 1, wherein for the compound of Formula (I):

(a) R$_1$ is P$_2$ and R$_2$ is H; or (b) R$_1$ is H and R$_2$ is P$_2$; or (c) R$_1$ is P$_2$ and R$_2$ is P$_2$.

3. The transdermal patch of claim 1, wherein for the compound of Formula (I):

(a) P$_2$ is or

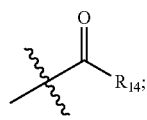

(b) P$_2$ is

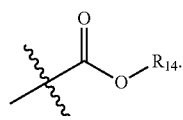

4. The transdermal patch of claim 1, wherein for the compound of Formula (I):

(a) each of R$_{20}$ through R$_{36}$ is H; or (b) at least one of R$_{20}$ through R$_{36}$ is deuterium.

5. The transdermal patch of claim 1, wherein for the compound of Formula (I):

(a) Z is —OH; or (b) Z is —OR$_{11}$; or (c) Z is —N(R$_{11}$)R$_{12}$; or (d) Z is P$_1$.

6. The transdermal patch of claim 1, wherein the compound of Formula (I) is a compound of Formula (IA) or a pharmaceutically acceptable salt, polymorph or stereoisomer thereof:

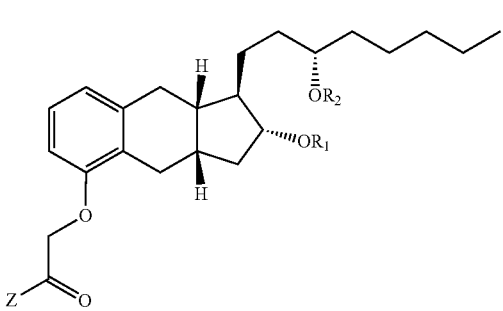

(IA)

wherein:

Z is —OH, —OR$_{11}$ or P$_1$;

R$_{11}$ is alkyl, substituted alkyl, cycloalkyl, substituted cycloalkyl, haloalkyl, heteroalkyl, substituted heteroalkyl, cycloheteroalkyl, substituted cycloheteroalkyl, alkylcycloalkyl, substituted alkylcycloalkyl, alkylcycloheteroalkyl, or substituted alkylcycloheteroalkyl;

P$_1$ is selected from:

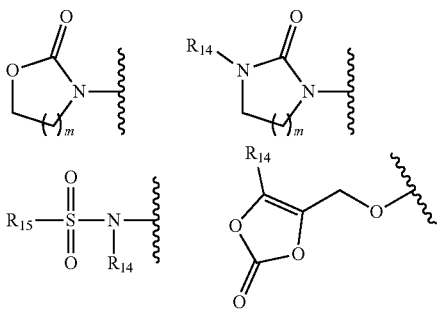

wherein:

m is 1, 2, 3 or 4; and

R$_{14}$ and R$_{15}$ are independently selected from H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl, or R$_{14}$ and R$_{15}$ together with the atoms to which they are attached optionally form a 5- to 7-membered ring; and R$_1$ and R$_2$ are independently H or P$_2$, wherein at least one of R$_1$ and R$_2$ is P$_2$, and wherein P$_2$ is selected from:

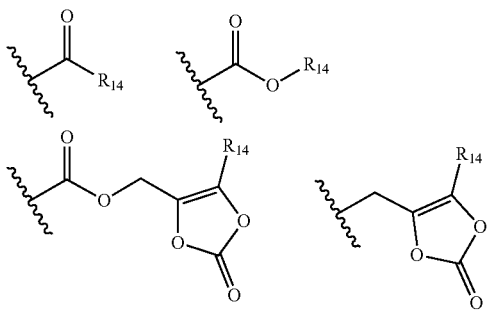

wherein $R_{14}$ is selected from H, alkyl, cycloalkyl, alkylcycloalkyl, haloalkyl, aryl, heteroaryl, arylalkyl, heteroarylalkyl, substituted aryl, substituted heteroaryl, substituted arylalkyl, and substituted heteroarylalkyl.

7. The transdermal patch of claim 1, wherein the topical composition further comprises a permeation enhancer, and optionally one or more additional excipients selected from solubilizers, lipophilic solvents, and thickeners.

8. The transdermal patch of claim 7, wherein the permeation enhancer is selected from dimethyl sulfoxide (DMSO), decylmethylsulfoxide, laurocapram, pyrrolidones, surfactants, alcohols, polyethylene glycol, diethylene glycol monoethyl ether, oleic acid, N-lauroyl sarcosine, sodium octyl sulfate, sodium lauryl sulfoacetate, and fatty acid esters.

9. The transdermal patch of claim 8, wherein:
the pyrrolidones are selected from 2-pyrrolidone and N-methyl-2-pyrrolidine;
the surfactants are selected from sodium laureth sulfate and sorbitan monolaurate;
the alcohols are oleyl alcohol;
the polyethylene glycol is PEG 400; and
the fatty acid esters are selected from isopropyl myristate, methyl laurate, glyceryl oleate, glycerol mono-oleate, and propylene glycol mono-oleate.

10. The transdermal patch of claim 7, wherein the solubilizers are selected from $C_2$-$C_8$ alcohols.

11. The transdermal patch of claim 7, wherein the lipophilic solvents are selected from lipophilic alcohols, polyethylene glycol, diethylene glycol monoethyl ether, polysorbates, Labrasol, fatty acid esters, diethyl sebacate, propylene glycol monocaprylate, propylene glycol laurate, mono- and di-glycerides, medium-chain triglycerides, caprylic/capric triglyceride, glyceryl monocaprylate, glyceryl mono-oleate, glyceryl mono-linoleate, glycerol oleate/propylene glycol, mineral oil, and vegetable oils.

12. The transdermal patch of claim 11, wherein:
the lipophilic alcohols are selected from hexylene glycol, octyldodecanol, oleyl alcohol and stearyl alcohol;
the polyethylene glycol is selected from PEG 100, PEG 300, PEG 400 and PEG 3350;
the polysorbates are selected from Tween 20 to 80;
the fatty acid esters are selected from isopropyl myristate and di-isopropyl adipate; and
the mono- and di-glycerides are Capmul MCM.

13. The transdermal patch of claim 7, wherein the thickeners are selected from glycerol, stearyl alcohol, and polymers.

14. The transdermal patch of claim 13, wherein the polymers are selected from polydimethylsiloxane (dimethicone), Carbopol polymers, acrylic polymers, polyvinyl alcohol, polyvinylpyrrolidone, methyl cellulose, ethyl cellulose, hydroxymethyl cellulose, and hydroxypropyl cellulose.

15. The transdermal patch of claim 1, wherein the topical composition further comprises a hydrophilic solvent.

16. The transdermal patch of claim 15, wherein the hydrophilic solvent is a $C_1$-$C_5$ alcohol or/and water.

17. The transdermal patch of claim 16, wherein the $C_1$-$C_5$ alcohol is ethanol, isopropanol, glycerol, propylene glycol or 1,2-pentanediol.

18. The transdermal patch of claim 1, which further comprises a microporous membrane, a skin adhesive and a backing material.

19. A method of treating pulmonary hypertension, comprising applying to a subject in need of treatment the transdermal patch of claim 1.

20. The method of claim 19, wherein the pulmonary hypertension is pulmonary arterial hypertension.

* * * * *